(12) United States Patent
Ethell

(10) Patent No.: US 9,943,578 B2
(45) Date of Patent: Apr. 17, 2018

(54) STANDARDIZED EX VIVO PLATFORMS FOR THE ANTIGEN-SPECIFIC EXPANSION OF CD4+ T CELL POPULATIONS

(71) Applicant: WESTERN UNIVERSITY OF HEALTH SCIENCES, Pomona, CA (US)

(72) Inventor: Douglas Wayne Ethell, Riverside, CA (US)

(73) Assignee: Western University of Health Sciences, Pomona, CA (US)

( * ) Notice: Subject to any disclaimer, the term of this patent is extended or adjusted under 35 U.S.C. 154(b) by 0 days.

(21) Appl. No.: 14/398,496

(22) PCT Filed: May 8, 2013

(86) PCT No.: PCT/US2013/040172
§ 371 (c)(1),
(2) Date: Nov. 3, 2014

(87) PCT Pub. No.: WO2013/169922
PCT Pub. Date: Nov. 14, 2013

(65) Prior Publication Data
US 2015/0337262 A1    Nov. 26, 2015

Related U.S. Application Data

(60) Provisional application No. 61/644,265, filed on May 8, 2012.

(51) Int. Cl.
| | | |
|---|---|---|
| A61K 48/00 | (2006.01) | |
| A61K 39/00 | (2006.01) | |
| A61K 39/385 | (2006.01) | |
| C12N 5/0783 | (2010.01) | |
| C12N 5/0784 | (2010.01) | |

(52) U.S. Cl.
CPC ........ *A61K 39/0007* (2013.01); *C12N 5/0636* (2013.01); *C12N 5/0639* (2013.01); *A61K 2039/5158* (2013.01); *A61K 2039/57* (2013.01); *C07K 2319/00* (2013.01); *C07K 2319/03* (2013.01); *C12N 2500/44* (2013.01); *C12N 2501/052* (2013.01); *C12N 2501/22* (2013.01); *C12N 2501/2304* (2013.01); *C12N 2501/25* (2013.01); *C12N 2501/50* (2013.01); *C12N 2501/998* (2013.01); *C12N 2502/1121* (2013.01); *C12N 2502/1394* (2013.01); *C12N 2506/02* (2013.01); *C12N 2510/00* (2013.01)

(58) Field of Classification Search
CPC ............ C12N 2510/00; C07K 2319/00; C07K 2319/03
USPC ............................... 424/93.21, 192.1, 193.1
See application file for complete search history.

(56) References Cited

U.S. PATENT DOCUMENTS

| | | |
|---|---|---|
| 2002/0034513 A1* | 3/2002 | Rhode et al. |
| 2002/0137108 A1 | 9/2002 | Mullan et al. |
| 2005/0003431 A1* | 1/2005 | Wucherpfennig et al. |
| 2008/0063654 A1* | 3/2008 | McNeel et al. |
| 2009/0123486 A1 | 5/2009 | Fritz et al. |
| 2009/0246869 A1 | 10/2009 | Tseng et al. |
| 2010/0285108 A1 | 11/2010 | Pfeifer et al. |

FOREIGN PATENT DOCUMENTS

| | | |
|---|---|---|
| CN | 102091327 A | 6/2011 |
| CN | 102428101 A | 4/2012 |
| WO | WO-02/32451 A1 | 4/2002 |
| WO | WO-02/32451 A8 | 4/2002 |
| WO | WO-2006/077152 A2 | 7/2006 |
| WO | WO-2006/077152 A3 | 7/2006 |
| WO | WO-2009/015841 A1 | 2/2009 |
| WO | WO-2009/111396 A1 | 9/2009 |
| WO | WO-2009/112831 A1 | 9/2009 |
| WO | 2009/120891 A2 | 10/2009 |
| WO | WO-2009/120891 A2 | 10/2009 |
| WO | WO-2009/120891 A3 | 10/2009 |
| WO | WO-2010/106127 A2 | 9/2010 |
| WO | WO-2010/106127 A3 | 9/2010 |

OTHER PUBLICATIONS

Office Action english translation of corresponding Chinese Application No. 201380033983.2, dated Jan. 4, 2016.
English Abstract of CN102091327.
International Search Report and Written Opinion for PCT Application No. PCT/US2013/040172 dated Sep. 19, 2013.
International Preliminary Report on Patentability for PCT Application No. PCT/US2013/040172 dated Nov. 20, 2014.
Sporri et al.: "Inflammatory Mediators are Insufficient for Full Dendritic Cell Activation and Promote Expansion of CD4+ T Cell Populations Lacking Helper Function," Nature Immonology, vol. 6, No. 2, pp. 163-170, Feb. 2005.
Supplementary European Search Report for EP Application No. 13788471.4, dated Dec. 11, 2015.
Tseng, Su-Yi et al., "Generation of immunogenic dendritic cells from human embryonic stem cells without serum and feeder cells", Regenerative Medicine, Future Medicine Ltd., GB, vol. 4, No. 4, Jul. 1, 2009, pp. 513-526.
Spörri, R. et al. (Feb. 2005, e-published Jan. 16, 2005). "Inflammatory mediators are insufficient for full dendritic cell activation and promote expansion of CD4+ T cell populations lacking helper function" *Nature Immunol* 6(2):163-170.

\* cited by examiner

*Primary Examiner* — Shin Lin Chen
(74) *Attorney, Agent, or Firm* — Mintz Levin Cohn Ferris Glovsky and Popeo, P.C.

(57) ABSTRACT

The invention relates to methods, peptides, nucleic acids and cells for use in isolating and expanding human T cell populations in an antigen-specific manner for immunodiagnostic or therapeutic purposes. The invention also relates to professional antigen presenting cells derived from pluripotent human stem cells, and to customizable antigen presentation by the antigen presenting cells.

1 Claim, 45 Drawing Sheets

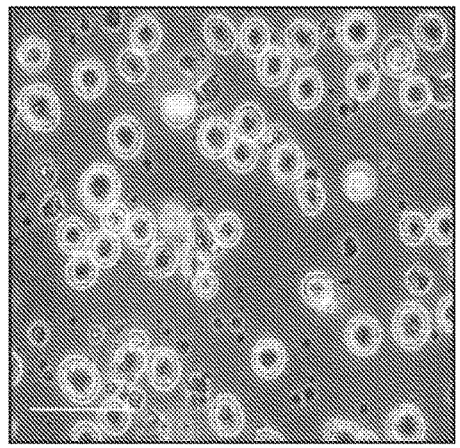
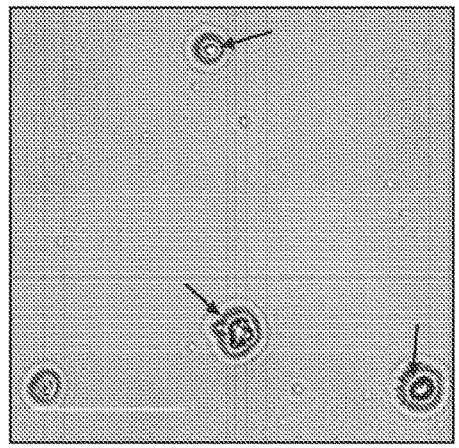
*FIG. 3A*  *FIG. 3B*
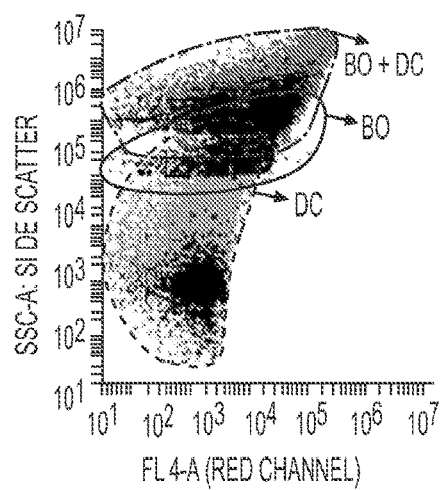
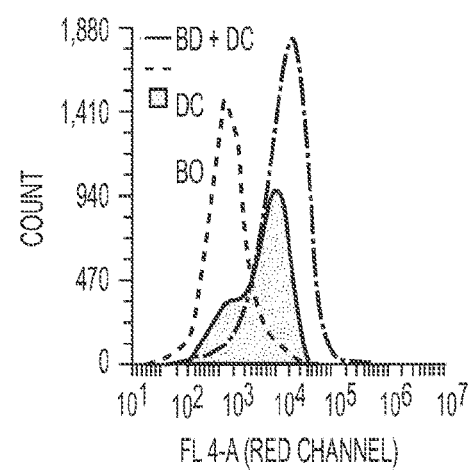
*FIG. 3C*  *FIG. 3D*

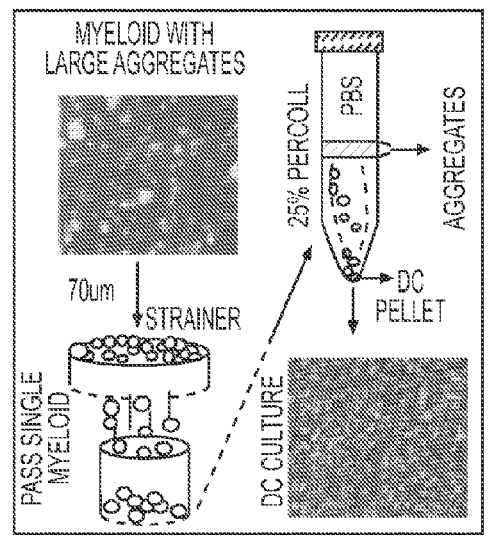
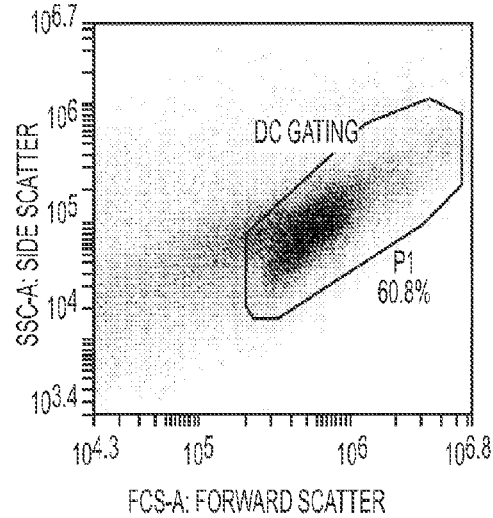
*FIG. 5A*  *FIG. 5B*
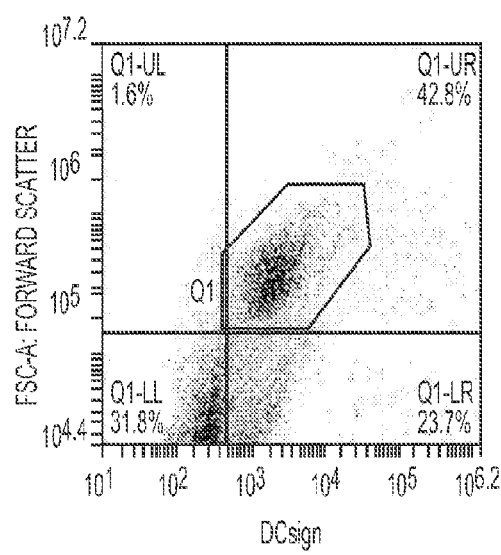
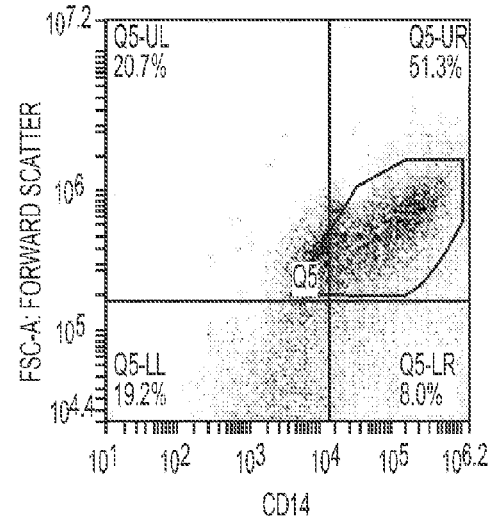
*FIG. 5C*  *FIG. 5D*

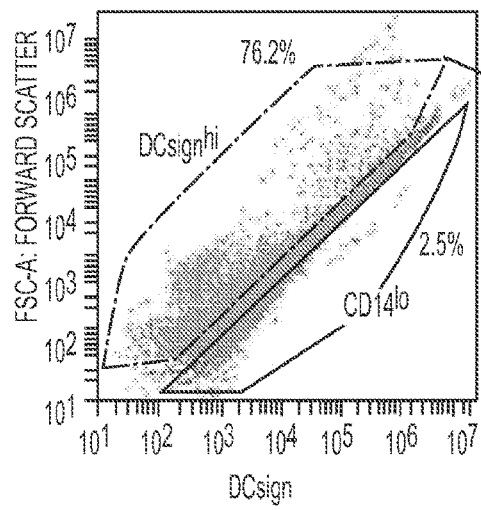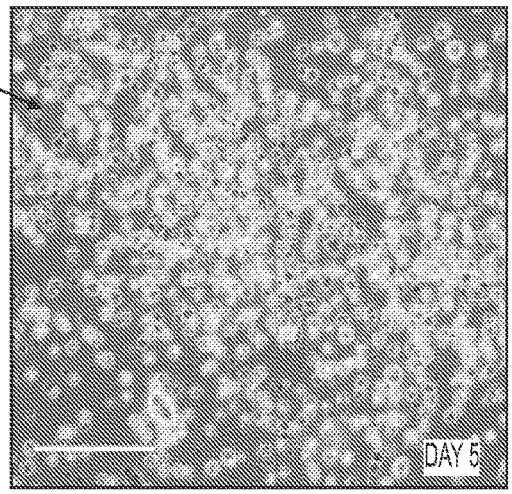
*FIG. 5I*  *FIG. 5J*
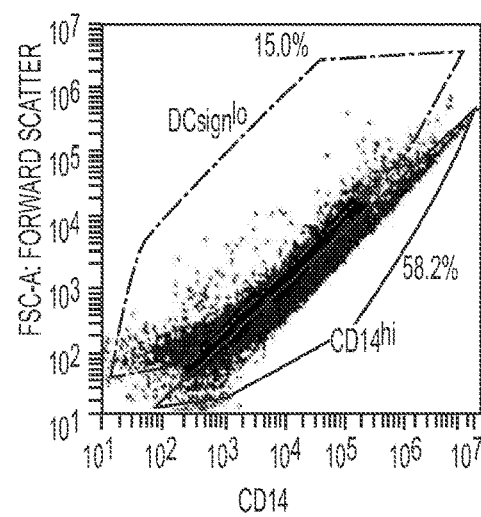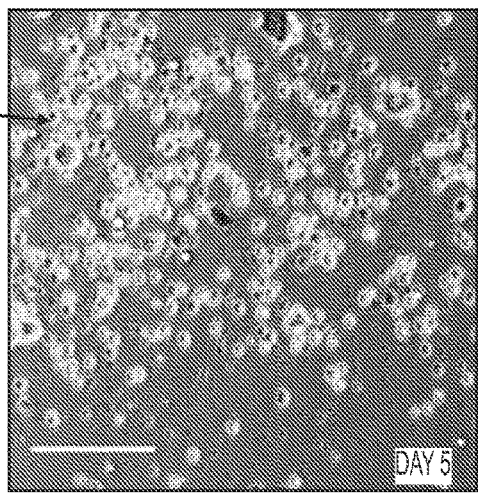
*FIG. 5K*  *FIG. 5L*

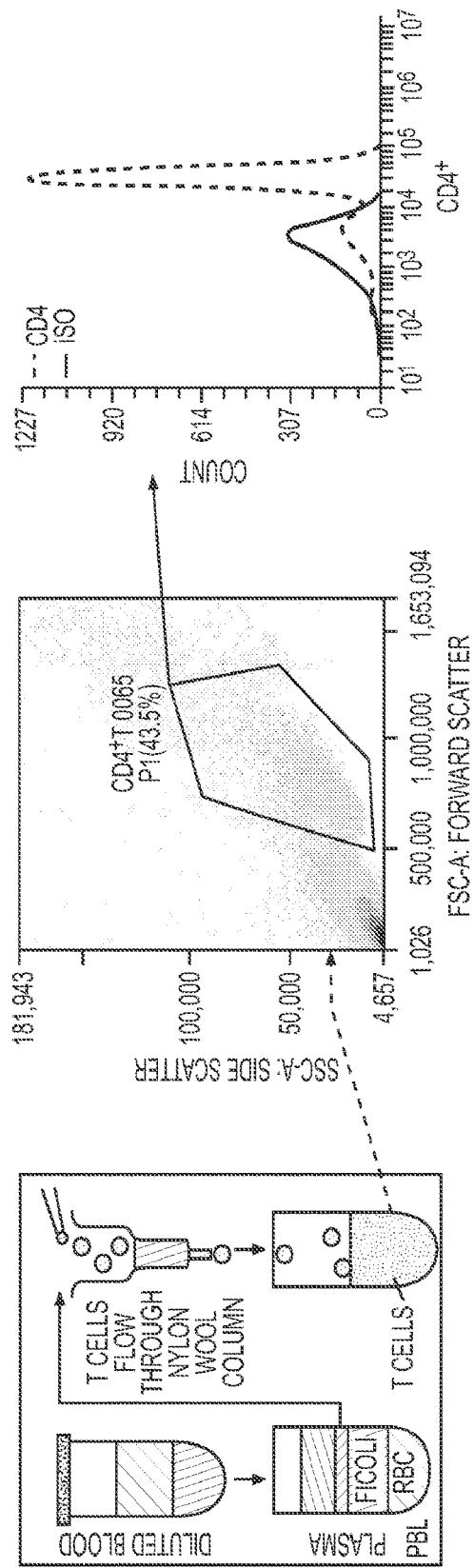

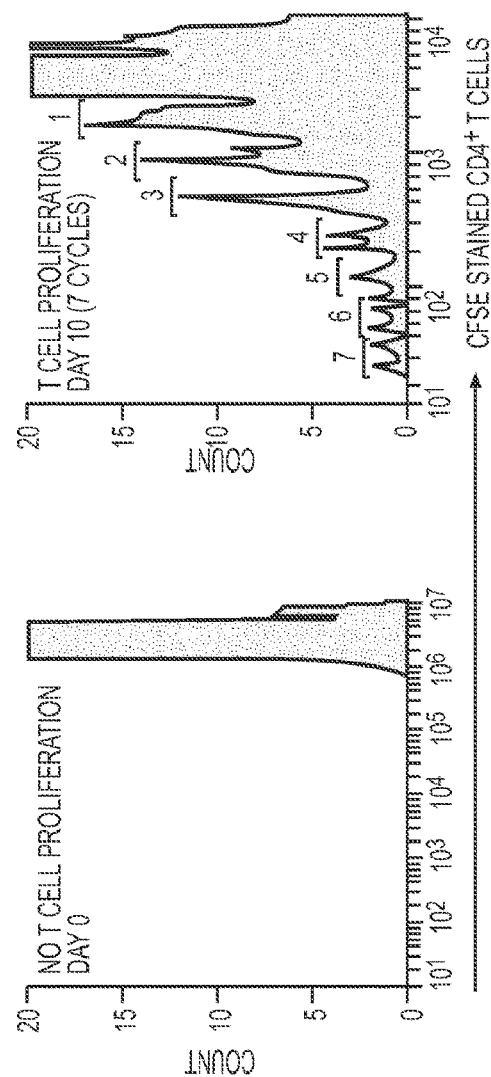
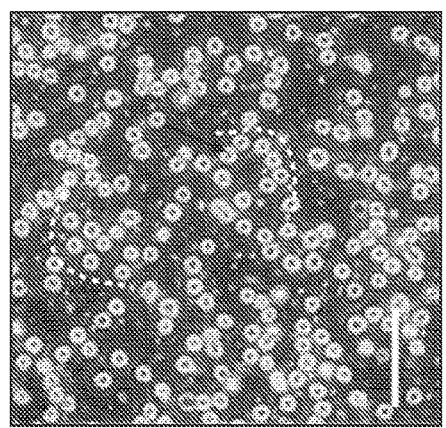
FIG. 6F
FIG. 6E
FIG. 6D

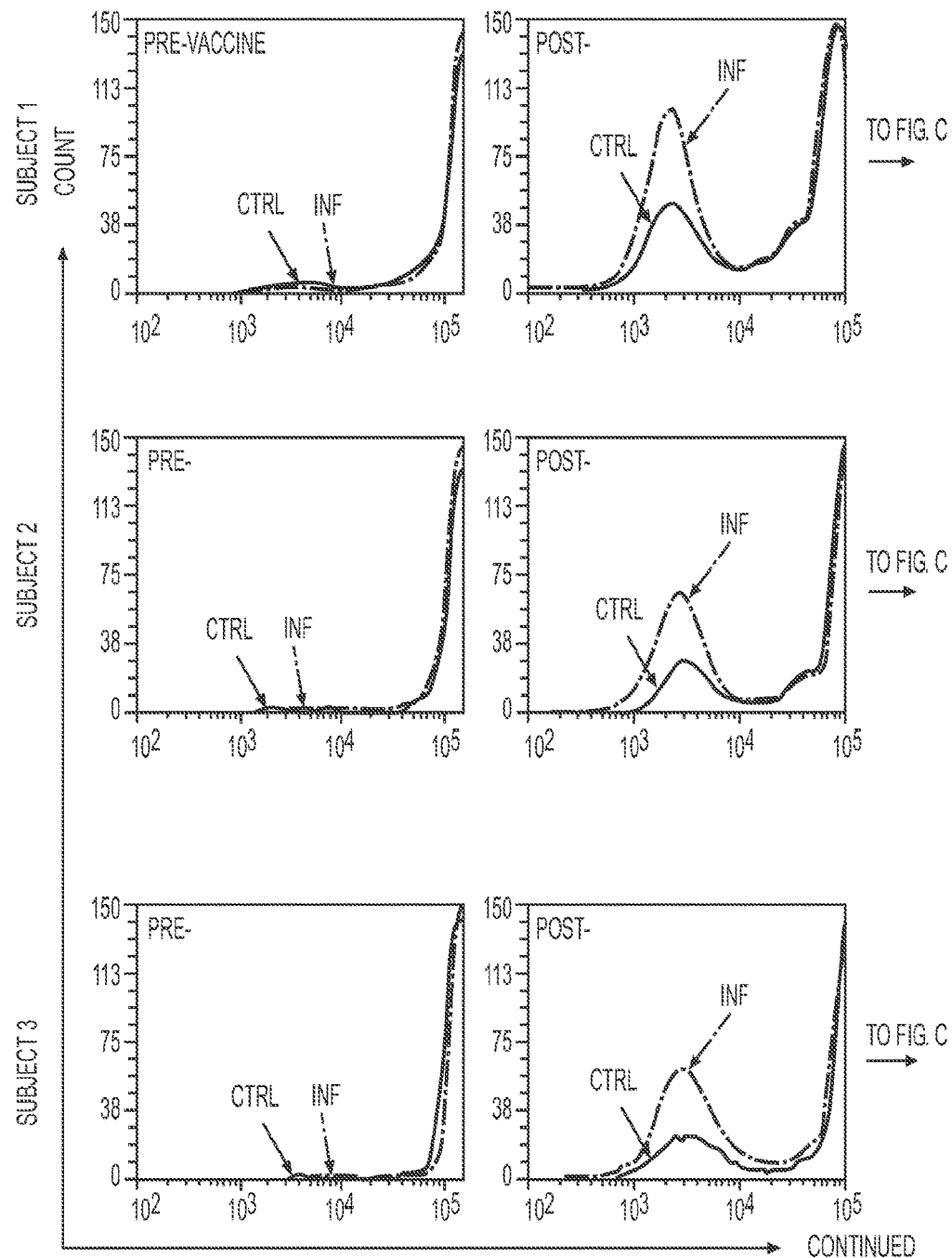
*FIG. 7A*  *FIG. 7B*

```
IIQAEFYLNPDQSGEFMFDFDGDEIFHVDMAKKETVWRLE
EFGRFASFEAQGALANIAVDKANLEIMTKRSNYTPITNVP
PEVTVLTNSPVELREPNVLICFIDKFTPPVVNVTWLRNGK
PVTTGVSETVFLPREDHLFRKFHYLPFLPSTEDVYDCRVE
HWGLDEPLLKHWEFDAPSPLPGTTENVVCALGLTVGLVGI
IIGTIFIIKGLRLSNAAERRGPL-stop
```

*FIG. 9*

```
  1 maisgvpvlg ffiiavlmsa qeswaikeeh viiqaefyln pdqsqefmfd fdgdeifhvd
 61 makketvwrl eefgrfasfe aqgalaniav dkanleimtk rsnytpitnd kftppvvnvt
121 wlrngkpvtt gvsetvflpr edhlfrkfhy lpflpstedv ydcrvehwgl deplkhwef
181 dapsplett envvcalglt vglvgiiigt ifiikgvrks naaerrgpl
```

FIG. 10

| 1 | 2 | 3 | 4 | 5 |

MSAQESWAIKEEHV DAEFRHDSGYEVH IGGGSGGGGSGGGGS IQAEFYL
NPDQSGEFMFDFDGDEIFHVDMAKKETVWRLEEFGRFASFEAQGALANTAVDK
ANLEIMTKRSNYTPITNVPPEVTVLTNSPVELREPNVLICFIDKFTPPVVNVT
WLPNGKPVTTGVSETVFLPREDHLFRKFHYLPFLPSTEDVYDCRVEHWGLDEP
LLKHWEFDAPSPLPGTTENVVCALGLTVGLVGIIIGTIFIIKGLRLSNAAERR
GPL-stop

FIG. 11

| 1 | | 2 | 3 | | 4 | 5 |
|---|---|---|---|---|---|---|

MSAQESWAIKEEHV DSGYEVH IGGGSGGGGSGGGGS IIQAEFYL
NPDQSGEFMFDFDGDEIFHVDMAKKETVWRLEEFGRFASFEAQGALANIAVDK
ANLEIMTKRSNYTPITNVPPEVTVLTNSPVELREPNVLICFIDKFTPPVVNVT
WLRNGKPVTTGVSETVFLPREDHLFRKFHYLPFLPSTEDVYDCRVEHWGLDEP
LLKHWEFDAPSPLPGTTENVVCALGLTVGLVGIIIGTIFIIKGLRLSNAAERR
GPL-stop

FIG. 12

|   1   |   2   |   3   |   4   |
|-------|-------|-------|-------|

| MSAQESWAIKEEHV | KLVFFAEDVGSNKGA | IGGGSGGGGSGGGGS | IIQAEFYL
NPDQSGEFMFDFDGDEIFHVDMAKKETVWRLEEFGRFASFEAQGALANIAVDK
ANLEIMTKRSNYTPITNVPPEVTVLTNSPVELREPNVLICFIDKFTPPVVNVT
WLRNGKPVTTGVSETVFLPREDHLFRKFHYLPFLPSTEDVYDCRVEHWGLDEP
LLKHWEFDAPSPLPGTTENVVCALGLTVGLVGIIIGTIFIIKGLRLSNAAERR
GPL-stop |

FIG. 13

```
        1           2            3                 4                    5
┌──────────────┬─────────────┬──────────────────┬─────────────────────────┐
│MSAQESWAIKEEHV│VGSNKGAIIGLM │IGGGSGGGGSGGGGS   │          IIQAEFYL       │
│NPDQSGEFMFDFDGDEIFHVDMAKKETVWRLEEFGRFASFEAQGALANIAVDK                    │
│ANLEIMTKRSNYTPITNVPPEVTVLTNSPVELREPNVLICFIDKFTPPVVNVT                    │
│WLRNGKPVTTGVSETVFLPREDHLFRKFHYLPFLPSTEDVYDCRVEHWGLDEP                    │
│LLKHWEFDAPSPLPGTTENVVCALGLTVGLVGIIIGTIFIIKGLRLSNAAERR                    │
│GPL-stop                                                                │
└────────────────────────────────────────────────────────────────────────┘
```

FIG. 14

```
     1            2           3               4                    5
| MSAQESWAIKEEHV | IIGLMVGGVVIA | IGGGSGGGGSGGGGS | IIQAEFYL
NPDQSGEFMFDFDGDEIFHVDMAKKETVWRLEEFGRFASFEAQGALANIAVDK
ANLEIMTKRSNYTPITNVPPEVTVLTNSPVELREPNVLICFIDKFTPPVVNVT
WLRNGKPVTTGVSETVFLPREDHLFRKFHYLPFLPSTEDVYDCRVEHWGLDEP
LLKHWEFDAPSPLPGTTENVVCALGLTVGLVGIIIGTIFIIKGLRLSNAAERR
GPL-stop
```

FIG. 15

```
          1              2              3                  4                    5
| MSAQESWAIKEEHV | DSGYEVHHQKLVFFAED | GGGSGGGGSGGGGS | IIQAEFYL
NPDQSGEFMFDFDGDEIFHVDMAKKETVWRLEEFGRFASFEAQGALANIAVDK
ANLEIMTKRSNYTPITNVPPEVTVLTNSPVELREPNVLICFIDKFTPPVVNVT
WLRNGKPVTTGVSETVFLPREDHLFRKFHYLPFLPSTEDVYDCRVEHWGLDEP
LLKHWEFDAPSPLPGTTENVVCALGLTVGLVGIIGTIFIIKGLRLSNAAERR
GPL-stop
```

FIG. 16

```
tatgatttatttgactgatagtgacctgtttcgttgcaacaaattggatgagcaatgc
 Y  D  F  I  L  T  D  S  D  L  F  R  C  N  K  L  D  E  Q  C
ttttatataatgccaactttgtacaaaaagcaggctccgaattcgccctttattcttg
 F  F  I  M  P  T  L  Y  K  K  A  G  S  E  F  A  L  L  F  L
tctgttctgcctcactcccgagctctactgactcccaacagagcgcccaagaagaaatg
 S  V  L  P  H  S  R  A  L  L  T  P  N  R  A  P  K  K  K  M
gccataagtggagtccctgtgctaggattttcatcatagctgtgctgatgagcgctcag
 A  I  S  G  V  P  V  L  G  F  F  I  I  A  V  L  M  S  A  Q
gaatcatgggctatcaagaagaacatgtggatgcagagttccgacacgattccggatac
 E  S  W  A  I  K  E  E  H  V  D  A  E  F  R  H  D  S  G  Y
gaggtgcacataggaggaggaagtggcggcggcggcagcggtggtggtggtagtatcatc
 E  V  H  I  G  G  G  S  G  G  G  G  S  G  G  G  G  S  I  I
caggccgagttctatctgaatcctgaccaatcaggcgagtttatgtttgactttgatggt
 Q  A  E  F  Y  L  N  P  D  Q  S  G  E  F  M  F  D  F  D  G
gatgagattttccatgtggatatggcaaagaaggagacggtctggcggcttgaagaattt
 D  E  I  F  H  V  D  M  A  K  K  E  T  V  W  R  L  E  E  F
ggacgattgccagctttgaggctcaaggtgcattggccaacatagctgtggacaaagcc
 G  R  F  A  S  F  E  A  Q  G  A  L  A  N  I  A  V  D  K  A
aacctggaaatcatgacaaagcgctccaactatactccgatcaccaatgtacctccagag
 N  L  E  I  M  T  K  R  S  N  Y  T  P  I  T  N  V  P  P  E
gtaactgtgctcacgaacagccctgtggaactgagagagcccaacgtcctcatctgtttc
 V  T  V  L  T  N  S  P  V  E  L  R  E  P  N  V  L  I  C  F
atagacaagttcaccccaccagtggtcaatgtcacgtggcttcgaaatggaaaacctgtc
 I  D  K  F  T  P  P  V  V  N  V  T  W  L  R  N  G  K  P  V
accacaggagtgtcagagacagtcttcctgcccagggaagaccaccttttccgcaagttc
 T  T  G  V  S  E  T  V  F  L  P  R  E  D  H  L  F  R  K  F
cactatctcccttcctgccctcaactgaggacgtttacgactgcagggtggagcactgg
 H  Y  L  P  F  L  P  S  T  E  D  V  Y  D  C  R  V  E  H  W
ggcttggatgagcctcttctcaagcactgggagtttgatgctccaagcccctctcccaga
 G  L  D  E  P  L  L  K  N  W  E  F  D  A  P  S  P  S  P  R
gactacagagaaacgtgggtgtgtgccctgggcctgactgtggggtctggtggggcatca
 D  Y  R  E  T  W  V  C  A  L  G  L  T  V  G  S  G  G  A  S
ttattgggaaccattcttcatcatcaaggattgcgcaaaagcaatgcac
 L  L  G  X  I  L  H  H  Q  X  I  A  Q  K  Q  C
```

*FIG. 17*

```
gattttattttgactgatagtgacctgtttcgttgcaacaaattgatgagcaatgcttttt
 F Y F D - - - P V S L Q Q I D E Q C F F
ataatgccaactttgtacaaaaaagcaggctccgaattcgccctttattcttgtctgtt
 I M P T L Y K K A G S E F A L L F L S V
ctgcctcactcccgagctctactgactcccaacagagcgcccaagaagaaaatggccata
 L P H S R A L L T P N R A P K K K M A I
agtggagtccctgtgctaggattttcatcatagctgtgctgatgagcgctcaggaatca
 S C V P V L G F F I I A V L M S A Q E S
tgggctatcaaagaagaacatgtggattccggatacgaggtgcaccagaagataggagga
 W A I K E E H V D S G Y E V H Q K I G G
ggaagtggcggcggcggcagcggtggtggtggtagtatcatccaggccgagttctatctg
 G S G G G G S G G G G S I I Q A E F Y L
aatcctgaccaatcaggcgagtttatgtttgactttgatggtgatgagattttccatgtg
 N P D Q S G E F M F D F D G D E I F H V
gatatggcaaagaaggagacggtctggcggcttgaagaatttggacgatttgccagcttt
 D M A K K E T V W R L E E F G R F A S F
gaggctcaaggtgcattggccaacatagctgtggacaaagccaacctggaaatcatgaca
 E A Q G A L A N I A V D K A N L E I M T
aagcgctccaactatactccgatcaccaatgtacctccagaggtaactgtgctcacgaac
 K R S N Y T P I T N V P P E V T V L T N
agccctgtggaactgagagagcccaacgtcctcatctgtttcatagacaagttcacccca
 S P V E L R E P N V L I C F I D K F T P
ccagtggtcaatgtcacgtggcttcgaaatggaaaacctgtcaccacaggagtgtcagag
 P V V N V T W L R N G K P V T T G V S E
acagtcttcctgcccagggaagaccacctttccgcaagttccactatctccccttcctg
 T V F L P R E D H L F R K F H Y L P F L
ccctcaactgaggacgtttacgactgcagggtggagcactggggcttggatgagcctctt
 P S T E D V Y D C R V E H W G L D E P L
ctcaagcactgggagtttgatgctccaagcccctctcccagagactacanataaacgtgg
 L K H W E F D A P S P S P R D Y X X T W
tgtgtgccctgggcctgactgtggggtctggtgggcatcatnattggggaccatcttcat
 C V P W A - L W G L V G I X I G D H L H
catca
 H
```

*FIG. 18*

| K | L | V | F | F | A | E | D | V | G | S | N | G | A |
|---|---|---|---|---|---|---|---|---|---|---|---|---|---|
| AAG | CTC | GTG | TTC | TTC | GCA | GAG | GAT | GTA | GGA | TCC | AAC | GGT | GCA |

FIG. 19

```
atgatttattttgactgatagtgacctgttcgttgcaacaaattgatgagcaatgctttt
 D  L  F  -  L  I  V  T  C  S  L  Q  Q  I  D  E  Q  C  F
ataatgccaactttgtacaaaaagcaggctccgaattcgccttttattcttgtctgtt
 I  M  P  T  L  Y  K  K  A  G  S  E  F  A  L  L  F  L  S  V
ctgcctcactcccgagctctactgactcccaacagagcgcccaagaagaaaatggccata
 L  P  H  S  R  A  L  L  T  P  N  R  A  P  K  K  K  M  A  I
agtggagtccctgtgctaggatttttcatcatagctgtgctgatgagcgctcaggaatca
 S  G  V  P  V  L  G  F  F  I  I  A  V  L  M  S  A  Q  E  S
tgggctatcaaagaagaacatgtggtaggatccaacaagggtgcaatcataggtctcatg
 W  A  I  K  E  E  H  V  V  G  S  N  K  G  A  I  I  G  L  M
ataggaggaggaagtggcggcggcggcagcggtggtggtggtagtatcatccaggccgag
 I  G  G  G  S  G  G  G  G  S  G  G  G  G  S  I  I  Q  A  E
ttctatctgaatcctgaccaatcaggcgagtttatgtttgactttgatggtgatgagatt
 F  Y  L  N  P  D  Q  S  G  E  F  M  F  D  F  D  G  D  E  I
ttccatgtggatatggcaaagaaggagacggtctggcggcttgaagaatttggacgattt
 F  H  V  D  M  A  K  K  E  T  V  W  R  L  E  E  F  G  R  F
gccagctttgaggctcaaggtgcattggccaacatagctgtggacaaagccaacctggaa
 A  S  F  E  A  Q  G  A  L  A  N  I  A  V  D  K  A  N  L  E
atcatgacaaagcgctccaactatactccgatcaccaatgtacctccagaggtaactgtg
 I  M  T  K  R  S  N  Y  T  P  I  T  N  V  P  P  E  V  T  V
ctcacgaacagccctgtggaactgagagagcccaacgtcctcatctgtttcatagacaag
 L  T  N  S  P  V  E  L  R  E  P  N  V  L  I  C  F  I  D  K
ttcaccccaccagtggtcaatgtcacgtggcttcgaaatggaaaacctgtcaccacagga
 F  T  P  P  V  V  N  V  T  W  L  R  N  G  K  P  V  T  T  G
gtgtcagagacagtcttcctgcccagggaagaccaccttttccgcaagttccactatctc
 V  S  E  T  V  F  L  P  R  E  D  H  L  F  R  K  F  H  Y  L
ccttcctgccctcaactgaggacgtttacgactgcagggtggagcactggggctggat
 P  F  L  P  S  T  E  D  V  Y  D  C  R  V  E  H  W  G  L  D
gagcctcttctcaagcactgggagtttgatgctccaagcc
 E  P  L  L  K  H  W  E  F  D  A  P  S
```

FIG. 20

| I | I | G | L | M | V | G | G | V | V | I | A |
|---|---|---|---|---|---|---|---|---|---|---|---|
| ATC | ATA | GGT | CTC | ATG | GTA | GGT | GGT | GTA | GTC | ATC | GCA |

FIG. 21

```
atatgatttattttgactgatagtgacctgtttcgttgcaacaaattgatgagcaatgcttt
  M  I  Y  F  D  -  -  -  P  V  S  L  Q  Q  I  D  E  Q  C  F
tttataatgccaactttgtacaaaaaagcaggctccgaattcgcccttttattcttgtct
  F  I  M  P  T  L  Y  K  K  A  G  S  E  F  A  L  L  F  L  S
gttctgcctcactcccgagctctactgactcccaacagagcgcccaagaagaaaatggcc
  V  L  P  H  S  R  A  L  L  T  P  N  R  A  P  K  K  K  M  A
ataagtggagtccctgtgctaggattttcatcatagctgtgctgatgagcgctcaggaa
  I  S  G  V  P  V  L  G  F  F  I  I  A  V  L  M  S  A  Q  E
tcatgggctatcaaagaagaacatgtggattccggatacgaggtgcaccaccagaagctc
  S  W  A  I  K  E  E  H  V  D  S  G  Y  E  V  H  H  Q  K  L
gtgttcttcgcagaggatataggaggaggaagtggcggcggcggcagcggtggtggtggt
  V  F  F  A  E  D  I  G  G  S  G  G  G  G  S  G  G  G  G
agtatcatccaggccgagttctatctgaatcctgaccaatcaggcgagtttatgtttgac
  S  I  I  Q  A  E  F  Y  L  N  P  D  Q  S  G  E  F  M  F  D
tttgatggtgatgagattttccatgtggatatggcaaagaaggagacggtctggcggctt
  F  D  G  D  E  I  F  H  V  D  M  A  K  K  E  T  V  W  R  L
gaagaatttggacgatttgccagctttgaggctcaaggtgcattggccaacatagctgtg
  E  E  F  G  R  F  A  S  F  E  A  Q  G  A  L  A  N  I  A  V
gacaaagccaacctggaaatcatgacaaagcgctccaactatactccgatcaccaatgta
  D  K  A  N  L  E  I  M  T  K  R  S  N  Y  T  P  I  T  N  V
cctccagaggtaactgtgctcacgaacagccctgtggaactgagagagcccaacgtcctc
  P  P  E  V  T  V  L  T  N  S  P  V  E  L  R  E  P  N  V  L
atctgtttcatagacaagttcaccccaccagtggtcaatgtcacgtggcttcgaaatgga
  I  C  F  I  D  K  F  T  P  P  V  V  N  V  T  W  L  R  N  G
aaacctgtcaccacaggagtgtcagagacagtcttcctgcccagggaagaccacttttc
  K  P  V  T  T  G  V  S  E  T  V  F  L  P  R  E  D  H  L  F
cgcaagttccactatctccccttcctgccctcaactgaggacgtttacgactgcagggtg
  R  K  F  H  Y  L  P  F  L  P  S  T  E  D  V  Y  D  C  R  V
gagcactggggcttggatgagcctcttctcaagcactgggagtttgatgctccaagccct
  E  H  W  G  L  D  E  P  L  L  K  H  W  E  F  D  A  P  S  P
ctcccanagactacanagaacgtggtgtgtgccctgggcctgactgtgggtctggtgggc
  L  P  X  T  T  X  N  V  V  C  A  L  G  L  T  V  G  L  V  G
atcattattgggaccatcttcatcatcanggg
```

FIG. 22

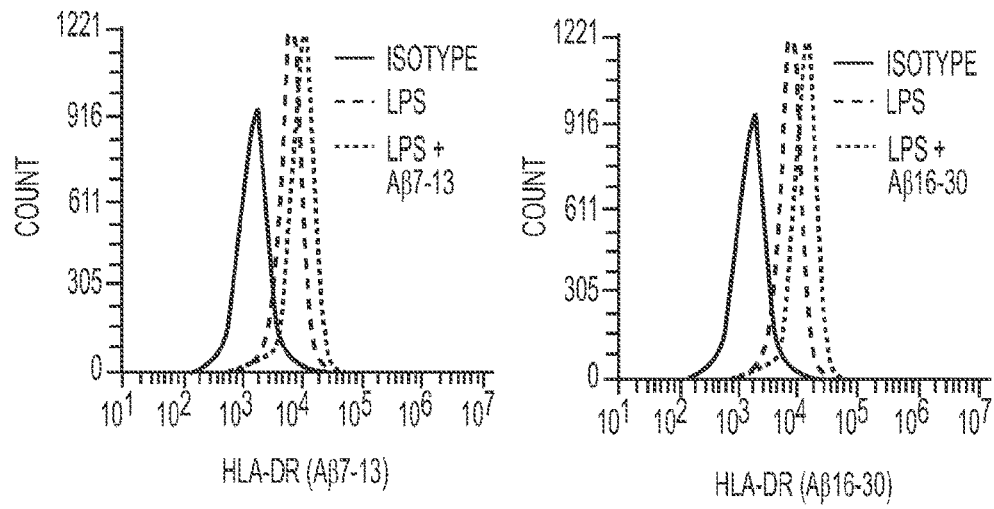
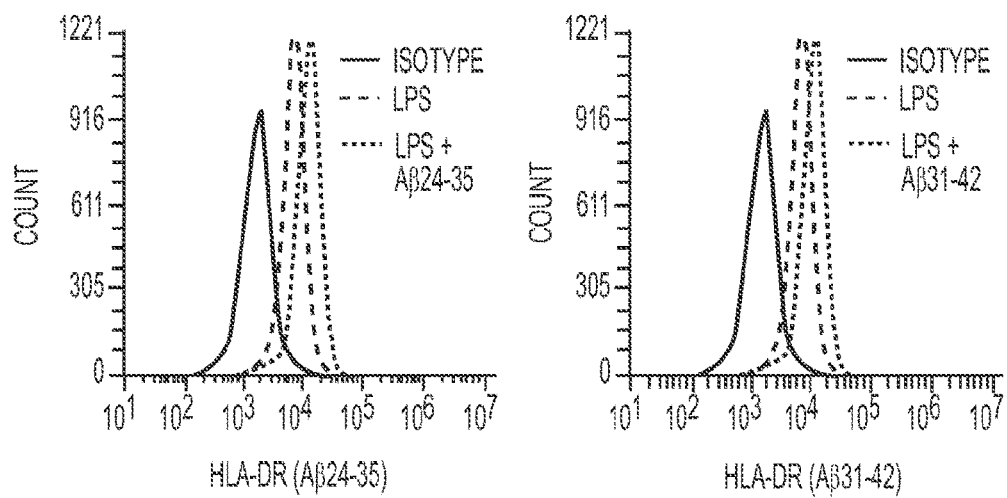
*FIG. 24*
CONTINUED

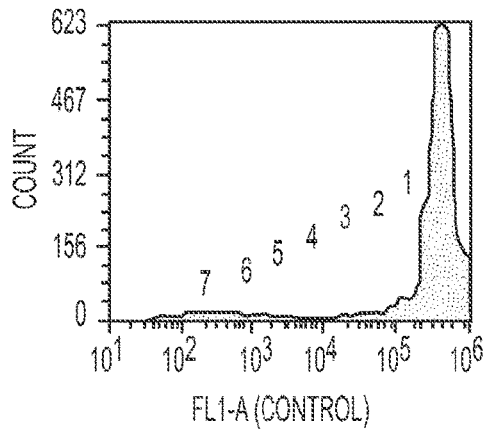
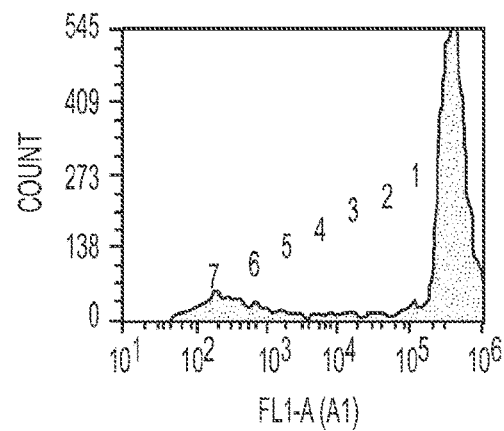
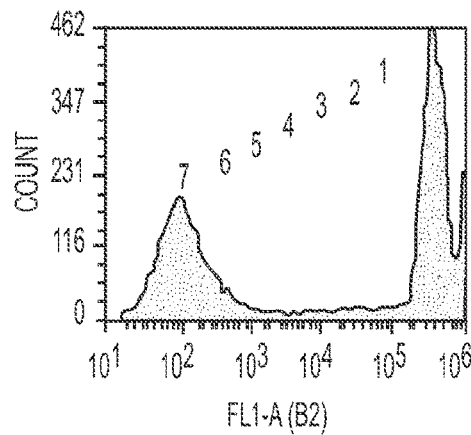
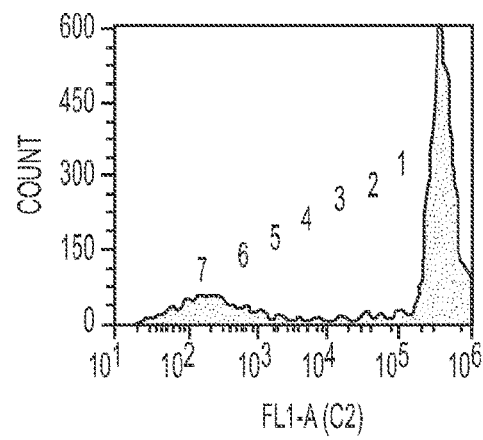
*FIG. 25E*

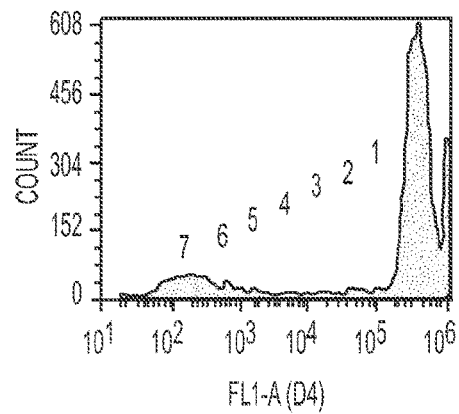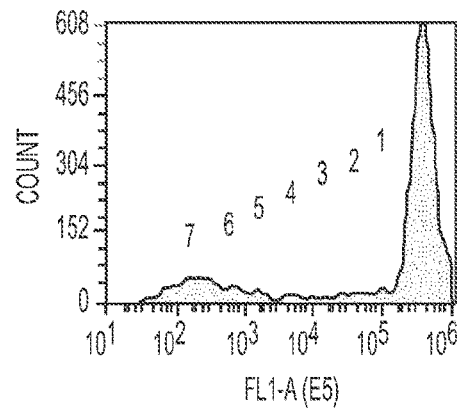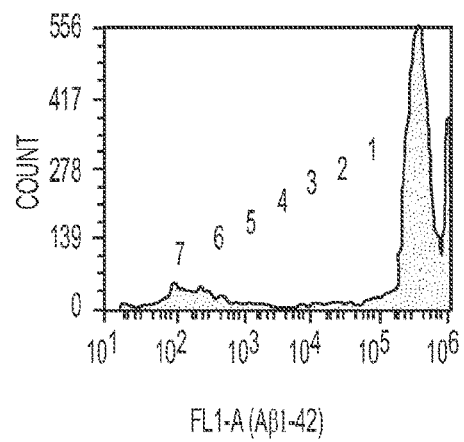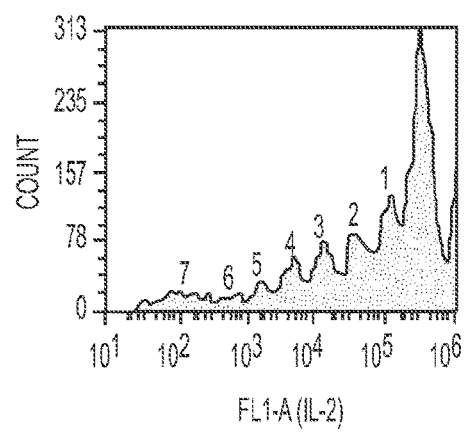
*FIG. 25E*
*CONTINUED*

STANDARDIZED EX VIVO PLATFORMS FOR THE ANTIGEN-SPECIFIC EXPANSION OF CD4+ T CELL POPULATIONS

CROSS-REFERENCE TO RELATED APPLICATIONS

This application is a national phase application of PCT/US13/40172, filed 8 May 2013, which claims priority to U.S. Application Ser. No. 61/644,265, filed 8 May 2012, and includes both disclosures herein by reference.

SEQUENCE LISTING

This application contains a Sequence Listing which has been submitted in ASCII format via EFS-Web and is hereby incorporated by reference in its entirety. Said ASCII copy, created on Aug. 10, 2015, is named 2015-08-10_Sequence_Listing.txt and is 54,169 bytes in size.

FIELD OF THE INVENTION

The invention relates to methods, peptides, nucleic acids and cells for use in isolating and expanding human T cell populations in an antigen-specific manner for immunodiagnostic or therapeutic purposes. The invention also relates to professional antigen presenting cells derived from pluripotent human stem cells, and to customizable antigen presentation by the antigen presenting cells.

BACKGROUND

CD4+ T cells play important roles in adaptive immunity as mediators of inflammation, tolerance, and as facilitators of B cell maturation (Pao et al., 1996; Klein et al, 2010). The human CD4+ T cell repertoire contains millions of different cells that vary in the T cell receptors (TCR) they express. Indeed, many human disorders involve discrete subsets of CD4+ T cells that proliferate in response to highly specific antigens, and the isolation of the small proportion of CD4+ cells that may be relevant to a specific condition is a daunting task. Consequently, the routine isolation or characterization of CD4+ T cells bearing TCRs that respond to a specific peptide have not been available in clinical or therapeutic settings.

The tremendous TCR repertoire represented by the T cell population, is the result of somatic recombination events of the alpha (α) and beta (β), or gamma (γ) and delta (δ) TCR genes of immature T cells residing in the thymus during thymic development. (Haas et al., 1993; Hayday et al., 1995) This recombination process generates a T cell repertoire with millions of different TCR combinations that collectively bind to every possible sequence of amino acids (Haas et al., 1993; Hayday et al., 1995). This repertoire circulates through vascular and lymphatic systems in a quiescent state until a T cell encounters professional APC, such as a dendritic cell (DC), with histocompatibility complexes (HLA class II) that present a peptide that binds to its TCR with appropriate affinity (Wen et al., 1998; Sakaguchi et al., 2000; Huang et al., 2012). An immunological synapse forms between the cells and the CD4+ T cell is stimulated to proliferate, generating dozens to thousands of clones. Newly produced T cells leave the secondary lymphoid organ, circulate through the body and accumulate at sites where the antigen is present. Activated CD4+ T cells release cytokines that act on nearby cells and coordinate adaptive immune responses. Days later, after the source of the antigen has been attenuated, most of the clones are eliminated by activation-induced cell death, except for a small number of that remain as memory cells, ready to trigger a rapid response should that antigen (pathogen) reappear (Wen et al., 1998; Villadangos et al., 2005).

Many CD4+ T cells isolated from fresh whole blood will divide for one or two divisions, but additional cycles of proliferation are required for the performance of clinically useful purposes. For example, the proportion of CD4+ T cells that divide relatively robustly (e.g., more than five times) in an assay period can be used an indicator of responsiveness to a query peptide. Panels that contain different fragment of a single protein or peptide can be used to create a proliferation profile that could correlate with CD4+ T cells responses to that antigen. Information derived from those results can then be used to determine the status and possible courses of action for a variety of human conditions. However, clinical characterizations of CD4+ T cells have been limited by the availability and variability in the preparation of appropriate APCs required for the successful expansion of antigen-specific CD4+ T cell populations.

Further complicating the development of diagnostic and therapeutic methods that isolate or characterize antigen-specific CD4+ T cell populations is the heterogeneity of human HLA-DR receptors in the human population. Briefly, class II HLA complexes contain a heterodimers of HLA-DRB and HLA-DRA receptors that form a binding pocket containing a peptide. The human population contains dozens, perhaps hundreds of different HLA-DRB alleles. Therefore, a large number of HLA class II alleles in the human population, combined with millions of possible TCR combinations, have made it technically difficult to isolate antigen-specific CD4+ T cells in autoimmune disorders driven by pathogenic T cells (Villdangos et al., 2005; Huang et al., 2012), such as type I diabetes (Haskins et al., 2011; Gojanovich et al., 2012; Delong et al., 2012), rheumatoid arthritis (Nikken et al., 2011; Albani et al., 2011), and multiple sclerosis (McFarland et al., 2007; Codarri et al., 2012; Sallusto et al., 2012). Put simply, TCRs that bind to a given peptide in one person may not bind an identical peptide in another because the individuals express different HLA-DRB alleles, thereby making the development of universal probes complicated and somewhat irreproducible. However, there are only two HLA-DRA alleles, one of which is found in 98% of the population. As such, methods of assessing specific CD4+ T cell responses that utilize the widely-expressed HLA-DRA allele will be applicable to the vast majority of the human population.

Accordingly, in view of the foregoing discussion, compositions and methods are described herein for providing platforms for standardizing analyses of CD4+ T cell responses. These methods and compositions include a differentiation protocol that efficiently produces myeloid dendritic cells (DC)s from human embryonic stem cells (hESC)s that can be used to stimulate antigen-specific CD4+ T cells isolated from whole blood. In sum, clinical characterizations of CD4+ T cells have been limited by variability in the preparation of primary dendritic cells (DC), but the use of stem cell-derived DCs circumvents this problem by providing a well-characterized and functionally-modifiable population of APCs for the analysis of T cell responses to any given antigen.

SUMMARY OF THE INVENTION

The invention provides compositions and methods for using human embryonic stem cell (hESC)-derived dendritic cells for the ex vivo stimulation of the proliferation of CD4+ T cell populations in an antigen-specific manner. The dendritic cells of the invention are customizable in that any peptide antigen that could conceivably drive an antigen-specific CD4+ T cell response can be presented on the surfaces of the dendritic cells and used to characterize a specific CD4+ T cell response. As such, the invention accommodates any a standardized approach for comparing immune responses to a particular antigen among multiple subject individuals, or in the same subject at different times. Similarly, the invention provides methods for expanding antigen-specific CD4+ T cell populations for various other purposes, like for use as a cellular vaccine or as an activated CD4+ T cell population that can be re-introduced into a patient for the treatment of a disease that can be alleviated by enhancing the immune response to specified peptide targets. For example, in situations where a certain antigen-specific CD4+ T cell population is thought to be beneficial but there are insufficient numbers, those cells can be expanded in vitro and returned to the subject. Moreover, in situations such as autoimmunity, where the highly proliferative CD4+ T cells are thought to be harmful, those cells can be expanded in vitro and reprogrammed into regulatory T cells (Tregs) that will suppress those specific T cell responses when returned to the subject.

The advantages of the present invention include, without limitation, the ability to identify and isolate of subsets of human CD4+ T cells from any person using a relatively small amount of blood. Uses of this invention could include, but are not limited to, characterizing responses to vaccines, as well as the diagnosis and/or treatment of human disorders that involve changes in CD4+ T cell responses and/or repertoires. For example, the invention provides methods and compositions for the diagnosis and treatment of Alzheimer's disease, Multiple sclerosis, Lupus, Psoriasis, Acquired immunodeficiency syndrome (AIDS), Severe combined immunodeficiency syndrome (SCID), Myasthenia gravis, Rheumatoid arthritis, Diabetes mellitus type I, Grave's disease, Hashimoto's thyroiditis, Hashimoto's encephalitis, Polymyositis, Sjögren's syndrome, Crohn's disease, Transverse myelitis, Vasculitis, Wegener's granulomatosis, Parkinson's disease, Muscular dystrophy, Vitiligo, Autoimmune cardiopathy, Celiac disease, Guillain-Barré syndrome, Narcolepsy, autoimmune disorders of unknown etiology, Autism, and allergies.

BRIEF DESCRIPTION OF THE FIGURES

FIG. 9 shows the full length amino acid sequence of HLA-DRA (SEQ ID NO: 5).

FIG. 10 shows the amino acid sequence of HLA-DRA, including the signal peptide [Genbank Ac. No. CAI18477.1] (SEQ ID NO: 6).

FIG. 11 shows the amino acid sequence of the HLA-DRA/Aβ1-13 fusion protein (SEQ ID NO: 7), including the signal peptide (No. 1), signal peptide cut site (No. 2), Aβ1-13 (No. 3), linker (No. 4), and HLA-DRA (No. 5).

FIG. 12 shows the amino acid sequence of the HLA-DRA/Aβ7-13 fusion protein (SEQ ID NO: 8), including the signal peptide (No. 1), signal peptide cut site (No. 2), Aβ7-13 (No. 3), linker (No. 4), and HLA-DRA (No. 5).

FIG. 13 shows the amino acid sequence of the HLA-DRA/Aβ16-30 fusion protein (SEQ ID NO: 9), including the signal peptide (No. 1), signal peptide cut site (No. 2), Aβ16-30 (No. 3), linker (No. 4), and HLA-DRA (No. 5).

FIG. 14 shows the amino acid sequence of the HLA-DRA/Aβ24-35 fusion protein (SEQ ID NO: 10), including the signal peptide (No. 1), signal peptide cut site (No. 2), Aβ24-35 (No. 3), linker (No. 4), and HLA-DRA (No. 5).

FIG. 15 shows the amino acid sequence of the HLA-DRA/Aβ31-42 fusion protein (SEQ ID NO: 11), including the signal peptide (No. 1), signal peptide cut site (No. 2), Aβ31-42 (No. 3), linker (No. 4), and HLA-DRA (No. 5). The Aβ31-42 contains a T41I substitution.

FIG. 16 shows the amino acid sequence of the HLA-DRA/Aβ7-23 fusion protein (SEQ ID NO: 12), including the signal peptide (No. 1), signal peptide cut site (No. 2), Aβ7-23 (No. 3), linker (No. 4), and HLA-DRA (No. 5).

FIG. 17 shows the DNA and amino acid sequences of a HLA-DRA/Aβ 1-13 fusion construct (SEQ ID NOS: 13-14, respectively).

FIG. 18 shows the DNA and amino acid sequences of a HLA-DRA/Aβ 7-13 fusion construct (SEQ ID NOS: 15-18, respectively, in order of appearance).

FIG. 19 shows the DNA and amino acid sequences of a HLA-DRA/Aβ 16-30 fusion construct (SEQ ID NOS: 19-20, respectively).

FIG. 20 shows the DNA and amino acid sequences of a HLA-DRA/ Aβ 24-35 fusion construct (SEQ ID NOS: 21-22, respectively).

FIG. 21 shows the DNA and amino acid sequences of a HLA-DRA/Aβ 31-42 fusion construct (SEQ ID NOS: 23-24, respectively).

FIG. 22 shows the DNA and amino acid sequences of a HLA-DRA/Aβ 7-23 fusion construct (SEQ ID NOS: 25-27, respectively, in order of appearance).

DETAILED DESCRIPTION

Figure 1A:
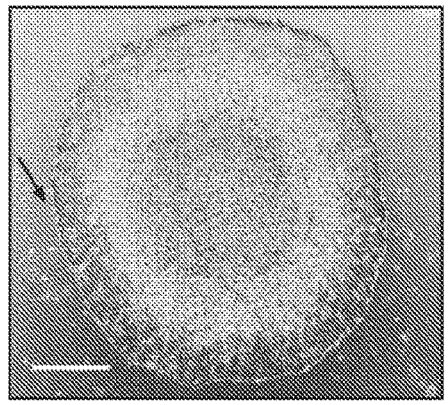
FIG. 1 exemplifies the differentiation of hESCs into common myeloid progenitors, including: (A) Photomicrograph of a pluripotent hESC (H9) colony showing smooth margin; (B) Flow cytometry histogram of SSEA4 immunostaining indicating pluripotency of H9 cells; (C) Small clumps of 30-50 hESC cells attached to OP9 cells soon after plating; (D) Differentiating colony after 4 days of hESC/OP9 co-culture; (E) Large differentiating colony shown after 8 days of co-culture; (F) Flow cytometry histogram showing CD34+ cells (red) isolated from colonies after 8 days of co-culture, isotype control is black; (G) Single cell suspension reformed into aggregates 1 day after plating in pHEMA-coated flask; (H) Inset of (G) showing large aggregates of myeloid cells with pumpkin shaped agranular morphologies, and that OP9 cells did not attach to the coated flasks and underwent apoptosis; (I) After three days in GM-CSF-containing medium, most myeloid cells began dissociating from aggregates, with single CMPs appearing in the culture; (J-L) Flow cytometry dot plots showing relative CD34 and CD45 expression, including (J) The CD34$^{lo}$/CD45$^{hi}$ population increased from 2-4% on day one, to (K) 20-30% by day 3, and (L) 60-70% by day 12; (M) Isotype control for J-L; (N) Histogram of CD45+ staining after twelve days; and (O) Histogram of CD43+ immunostaining after 12 days of CMP differentiation and expansion. Scale bars=10 μm.

The methods and compositions of the invention disclosed herein relate to assessing the immune response of a human subject to various peptide antigens. Stated in another way, the invention is directed to a standardized approach for comparing immune responses to a particular antigen among multiple subject individuals, or in the same subject at different times. The invention accommodates an analysis of an immune response to any peptide antigen that can be presented by an antigen presenting cell (APC) in the context of human leukocyte (HLA) class II. The invention is also particularly directed to assessing the CD4+ T cell component of an immune response.

In various embodiments, methods of the invention differentiate human embryonic stem cells (hESC)s into mature professional APCs. For example, a method of the invention can induce the differentiation of the hESCs into common myeloid progenitor cells, which, in turn, can be differentiated into immature dendritic cells, and then further differentiated into mature dendritic cells. In various embodiments the invention differentiates H9 hESC; however, one of skill in the art can choose to use any human pluripotent stem cell known in the art. For example, embryonic stem cells may be chosen from embryonic stem cell lines or may be obtained directly from primary embryonic tissue. A number of embryonic stem cell lines have been established including, but not limited to, H1, H7, H9, H13 and H14 (Thompson et al.); hESBGN-01, hESBGN-02, hESBGN-03 (BresaGen, Inc., Athens, Ga.); HES-1, HES-2, HES-3, HES-4, HES-5, HES-6 (ES Cell International, Inc., Singapore); HSF-1, HSF-6 (University of California at San Francisco); 13, 14, 16 (Technion-Israel Institute of Technology, Haifa, Israel); UCSF-1 and UCSF-2 (Genbacev et al., Fertil. Steril. 83(5): 1517-29, 2005); lines HUES 1-17 (Cowan et al., NEJM 350(13):1353-56, 2004); and line ACT-14 (Klimanskaya et al., Lancet, 365(9471):1636-41, 2005).

As stated above, hESC-derived mature dendritic cells of the invention primarily present fragments of a single peptide antigen in the context of their HLA class II molecules. Peptides that are presented on the APCs of the invention can be any peptide selected by one of skill in the art for the purpose of assessing a CD4+ T cell response specific to an antigen that comprises that peptide. In various embodiments, the antigen comprising the peptide is a component of a vaccine composition. For example, in various embodiments, the antigenic peptide comprises amino acids 126-138, (i.e., NH$_2$-HNTNGVTAACSHE-OH) (SEQ ID NO: 1), of Influenza HA, and can be used in methods of the invention to assess the CD4+ T cell responses in subjects that have been administered FLULAVAL®, an influenza virus vaccine marketed by GlaxoSmithKline, PLC.

However, because the methods of the invention relate to a standard platform that can be used to evaluate immune responses to any peptide that can produce a CD4+ T cell response, one of skill in the art can use the methods of the invention to evaluate CD4+ T cell responses to any vaccine that is capable of causing such a response in a subject. Accordingly, examples of vaccines known in the art that can be accommodated by invention also include AVA (Bio-Thrax) for anthrax; VAR (Varivax) and MMRV (ProQuad) for chickenpox; DTaP (Daptacel, Infanrix, Tripedia), Td (Decavaca, generic), DT (-generic-), Tdap (Boostrix, Adacel), DTaP-IPV (Kinrix), DTaP-HepB-IPV (Pediarix), DTaP-IPV/Hib (Pentacel), and DTaP/Hib (TriHIBit) for Diphtheria; HepA (Havrix, Vaqta) and HepA-HepB (Twinrix) for Hepatitis A; HepB (Engerix-B, Recombivax HB), Hib-HepB (Comvax), DTaP-HepB-IPV (Pediarix), and HepA-HepB (Twinrix) for Hepatitis B; Hib (ActHIB, PedvaxHIB, Hiberix), Hib-HepB (Comvax), DTaP/Hib (TriHIBit), and DTaP-IPV/Hib (Pentacel) for *Haemophilus influenzae* type b; HPV4 (Gardasil) and HPV2 (Cervarix) for Human Papillomavirus (HPV); TIV (Afluria, Agriflu, Fluarix, Fluvirin, Fluzone) and LAIV (FluMist) for Influenza; JE (Ixiaro and JE-Vax) for Japanese encephalitis (JE); MMR (M-M-R II) and MMRV (ProQuad) for Measles; MCV4 (Menactra), MPSV4 (Menomune), and MODC (Menveo) for Meningitis; MMR (M-M-R II) and MMRV (ProQuad) for Mumps; DTaP (Daptacel, Infanrix, Tripedia), Tdap (Adacel, Boostrix), DTaP-IPV (Kinrix), DTaP-HepB-IPV (Pediarix), DTaP-IPV/Hib (Pentacel), and DTaP/Hib (Tri-HIBit) for Pertussis; PCV7 (Prevnar), PCV13 (Prevnar13), and PPSV23 (Pneumovax 23) for Bacterial Pneumonia; Polio (Ipol), DTaP-IPV (Kinrix), DTaP-HepB-IPV (Pediarix), and DTaP-IPV/Hib (Pentacel) for Polio; Rabies (Imovax Rabies and RabAvert); RV1 (Rotarix) and RV5 (RotaTeq) for Rotavirus; MMR (M-M-R II) and MMRV (ProQuad) for Rubella; ZOS (Zostavax) for Shingles; Vaccinia (ACAM2000, Dryvax) for Smallpox and Monkeypox; DTaP (Daptacel, Infanrix, Tripedia), Td (Decavac, generic), DT (-generic-), TT (-generic-), Tdap (Boostrix, Adacel), DTaP-IPV (Kinrix), DTaP-HepB-IPV (Pediarix), DTaP-IPV/Hib (Pentacel), and DTaP/Hib (TriHIBit) for Tetanus; BCG (TICE BCG, Mycobax) for Tuberculosis (TB); Typhoid Oral (Vivotif) and Typhoid Polysaccharide (Typhim Vi) for Typhoid; and YF (YF-Vax) for Yellow Fever.

In addition to peptides that relate to vaccines, the method of the invention also diagnoses and tracks the progress of treatment of various autoimmune diseases based on $CD4^+$ T cell responses to a particular peptide associated with a specified autoimmune disease state. An "autoimmune disease," as understood herein, is a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), Caplan's Syndrome, Felty's Syndrome, psoriasis, dermatitis, Sjorgren's Syndrome, Still's Disease, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (MBA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

In various embodiments, the compositions and methods of the invention can be used to assess repertoires of $CD4^+$ T cell responses to the Alzheimer's peptideAmyloid-beta (Aβ). Briefly, Aβ is a polypeptide having 42 amino acids which is derived from the amyloid precursor protein (APP) by proteolytic processing. As understood herein, Aβ proteins also include mutants and allelic variants thereof derived from by amino acid exchange. In various embodiments, methods of the invention use, as an alternative to full length Aβ, peptides that may comprise Aβ1-13, Aβ7-13, Aβ16-30, Aβ24-35, Aβ31-42, and Aβ7-23.

In various embodiments, broad and strong responses to all Aβ peptides indicate ongoing immune responses to Aβ and all fragments of the Aβ. One of skill in the art could interpret such a response as being indicative of an ongoing response to accumulating Aβ pathology that eventually becomes less robust as energy sets in, eventually leading to a less robust $CD4^+$ response at a later stage of Alzheimer's disease. That is, an individual with a relatively robust $CD4^+$ response to Aβ, or certain Aβ fragments, would be considered pre Alzheimer's disease though no cognitive or behavioural changes may have been noticed.

Generally, any method of causing APCs to preferably present a particular single peptide fragment can be used in methods of the invention. For example, in various embodiments, methods of the invention load APCs by adding a peptide directly to the APCs in culture in a sufficient amount to cause the HLA class II molecules of the APCs to present the peptide, or fragments thereof. In various other methods of the invention, peptide antigens are presented on the surface of APCs in which nucleic acids encoding the peptide have been introduced. For example, the peptide may be encoded within a viral or plasmid vector.

In various embodiments of the invention, peptides that are presented by APCs are presented as a peptide component of a fusion protein that also comprises at least a portion of an HLA-II protein. For example, a fusion protein of the invention can comprise nucleic acid and amino acid sequences that are derived from Human Leukocyte Antigen (HLA) class II-DRA, a paralog of the HLA class II alpha chain. In various other embodiments, the fusion protein of the invention includes HLA-DRA fusion constructs that comprise fragments of Aβ. For example, as an alternative to full length Aβ, the fusion protein may comprise Aβ1-13, Aβ7-13, Aβ16-30, Aβ24-35, Aβ31-42, and Aβ7-23.

The HLA-DRA alpha chain is approximately 33-35 kDa and its gene contains five exons. Exon 1 encodes the leader peptide, exons 2 and 3 encode the two extracellular domains, and exon 4 encodes the transmembrane domain and the cytoplasmic tail. HLA-DRA does not have polymorphisms in the peptide binding part and acts as the sole alpha chain for the beta chains DRB1, DRB3, DRB4 and DRB5. HLA-DRA sequences are publicly available. For example, nucleotide and amino acid sequences can be found at: GenBank Accession Nos. CAI18477.1 (amino acid sequence), M60334.1 (DNA sequence), NP_061984.2 (amino acid sequence), AAA36275.1 (amino acid sequence), AAA59785.1 (amino acid sequence), AAA36302.1 (amino acid sequence), AAAH71659.1, CA118476.1 (amino acid sequence), and GI 3122 (gene sequence); as well as at EMBL accession Nos. AL935032.13 (DNA sequence), CAG33294.1 (amino acid sequence), CAQ08811.1 (DNA sequence), and EAX03629.1 (DNA sequence). One skilled in the art will appreciate that HLA-DRA nucleic acid and protein molecules can vary from those publicly available, such as polymorphisms resulting in one or more substitutions, deletions, insertions, or combinations thereof, while still retaining HLA-DRA biological activity. Accordingly, in various embodiments of the invention, the amino acid sequence of the HLA-DRA component of the fusion protein of the invention may be about 90%, about 91%, about 92%, about 93%, about 94%, about 95%, about 96%, about 97%, about 98%, about 99% identical to the HLA-DRA sequence exemplified in FIG. 2, or fragment thereof.

In various embodiments, fusion protein of the invention comprises a linker. Generally a linker is a flexible peptide linker element that is located between the HLA-DRA and the desired fused peptide components of the fusion protein. A linker element preferably has a length of 25 amino acids or less. In certain embodiments the linker element has a length of 3-30 amino acids, particularly a length of 3, 4, 5, 6, 7, 8, 9, 10, 11, 12-13, 14, 15, 16, 17, 18, 19 20, 21, 22, 23, 24, 25, 26, 27, 28 or 30 amino acids. In one embodiment the length of a linker element is 5-25 amino acids, 8-20 amino acids or 10-20 amino acids. More preferably, the length of the linker is 9-15 amino acids. Generally a linker element used herein may be composed of any known amino acids or of artificial amino acid derivatives. In certain embodiments the linker elements are built of small and hydrophilic non-charged amino acids. Generally the linker element according to the invention may comprise amino acids selected from G, S, A and T. A linker element is preferably a glycine/serine linker, i.e., a peptide linker substantially consisting of the amino acids glycine and serine, such as a polyglycine. In certain embodiments of the invention, the linker sequence is IGGGSGGGGSGGGGS (SEQ ID NO: 2).

As stated above, the invention also relates to methods of expanding a peptide antigen-restricted CD 4+ T cell population. In various embodiments, as indicated above, the method of the invention relates antigen-specific expansion of CD4+ T cell populations to immune responses to, for example, to vaccines, autoimmune diseases, and cognitive disorders associated with Aβ deposition.

Generally, the methods of the invention obtains human CD4+ T cells from whole blood that can be isolated using standard phlebotomy methods. An initial purification removes the majority of myeloid cells and B cells, enriching the T cell population. The T cells are then stained with carboxyfluorescein diacetate succinimidyl ester (CFSE) and then mixed with a panel of HLA-Aβ fusion protein expressing APCs and cocultured for 7-10 days. After this incubation period the cell mixture is stained with CD4-specific fluorescent antibody and run through a flow cytometer, such as a fluorescent activated cell scanner or sorter. CD4-positive (CD4+) fluorescence is used to identify CD4+ T cells, and CFSE intensity is used to determine how much proliferation those have undergone since the beginning of the test.

As stated above, the method of the invention expresses HLA-DRA fusion proteins in APCs. Therefore, the methods and compositions of the invention include DNA or RNA vectors that are capable of expressing the fusion constructs of the invention in an APC. Generally a vector comprises a promoter, a terminator downstream of the nucleotide sequence to be expressed. In various embodiments of the invention, the vector encodes for a recombinant virus. For example, in certain embodiments of the invention, the vector comprises sequences from a lentivirus genome, such as the FUW lentivirus vector (described in Science. 2002 Feb. 1. 295(5556):868-72. Epub 2002 Jan. 10.)

In some embodiments, the compositions and methods of the invention can be used as part of a direct immunization protocol. For example, viral vectors, liposomes, or other delivery methods could be used to deliver an HLA-DRA fusion protein construct directly into lymph nodes. This approach would allow for the rapid presentation of the query peptide in the HLA class II complexes of endogenous APCs. Thus, the invention provides a desirable alternative to traditional vaccine methods that introduce peptides as adjuvant complexes that must be processed by APCs and then carried to lymph nodes, a process that can take three to seven days. The direct delivery and immediate expression of query-bound HLA-DRA fusion proteins will be especially helpful in producing immune responses to pathogens that kill rapidly, such as Ebola virus.

EXAMPLES

Example 1

Figure 1B:
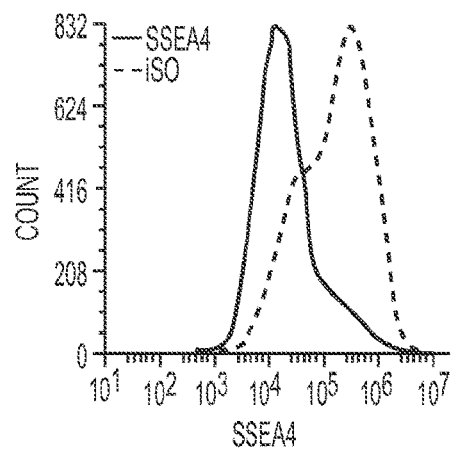

Method of Using hESC-Derived DCs Loaded with Influenza Antigens to Assess CD4+ T Cell Responses Hematopoietic stem cell (HSC) differentiation of hESC. H9 (NSCB code WA09, passage 23) hESC lines were maintained in mTeSR media with 5× supplement (Stem Cell Technologies), supplemented with additional bFGF (4 μg/ml, Life Technologies). Colonies of pluripotent H9 hESC (FIG. 1A) were maintained on matrigel using standard methods and tested for pluripotency every 5 passages with SSEA4 immunostaining, which was evaluated by microscopy and flow cytometry (FIG. 1B). Colonies were gently scraped into clumps of 30-60 cells and collected them into 15 ml tube followed by the centrifugation with 300×g for 5 min., and resuspended in HSC differentiation medium (HDM: α-MEM, 10% FBS, 100 μM monothioglycerol).

Prior to harvesting H9 cells for differentiation, flasks of approximately 70% confluent OP9 mouse stromal cells (ATCC) cells were rinsed and pre-incubated with HDM. The OP9 cells had been cultured in gelatinized (G1393, Sigma) T75 flasks in the OP9 growth medium (OP9M: α-MEM (Life Technologies) with 20% FBS (HyClone)). HDM containing hESC cell clumps were added directly to the flasks. On day four all HDM was replaced with fresh HDM, and on days six and eight, half of the HDM medium was replaced with fresh HDM.

Figure 1C:
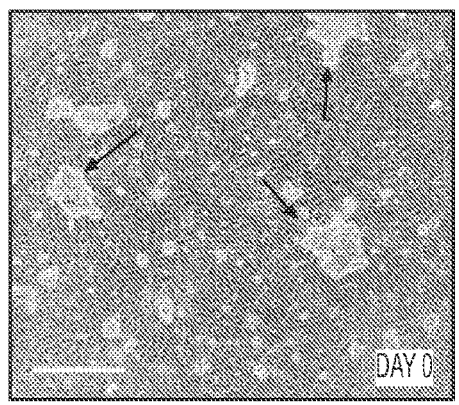
Figure 1D:
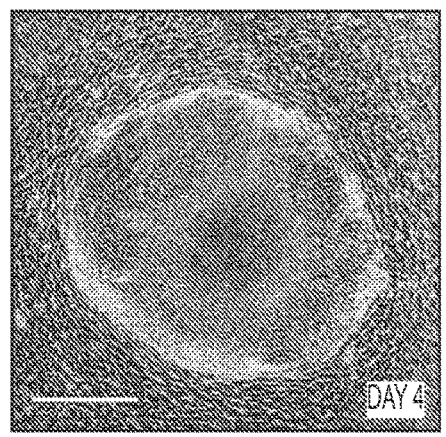

After two days of co-culture in HDM, initial hematopoietic differentiation of the HSC-containing clumps of H9 colonies attached to OP9 feeder layers and bega (FIG. 1C). Colony morphology after 4 days of co-culture was similar to hESC colonies, though cell sizes were more variable (FIG.

Figure 1E:
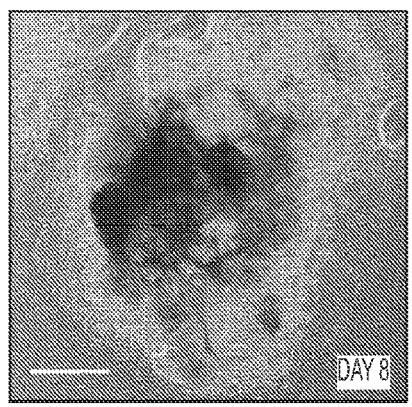
Figure 1F:
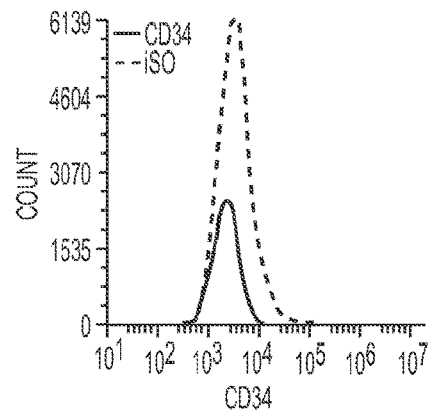

1D). After 8 days, the morphologies of colonies containing HSC were highly variable and distinctly different from the smooth margins and even appearance of pluripotent hESC colonies (FIG. 1E). Expression analysis of cells isolated from colonies after 8 days of co-culture showed CD34 immunostaining (FIG. 1F).

Figure 1G:
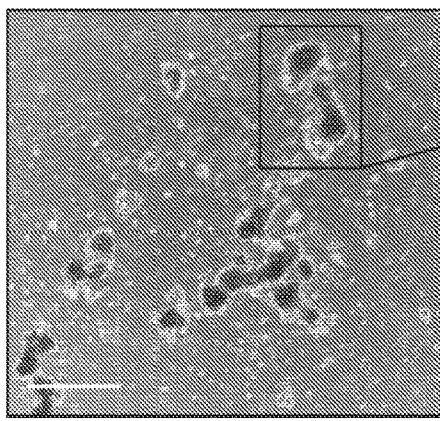
Figure 1H:
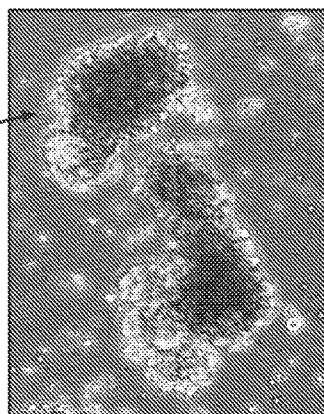
Figure 1I:
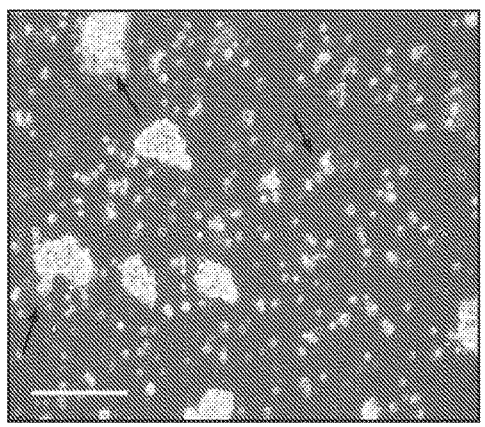
Figure 1J:
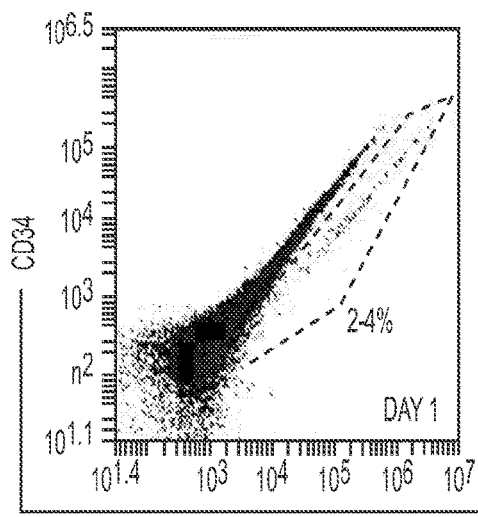
Figure 1K:
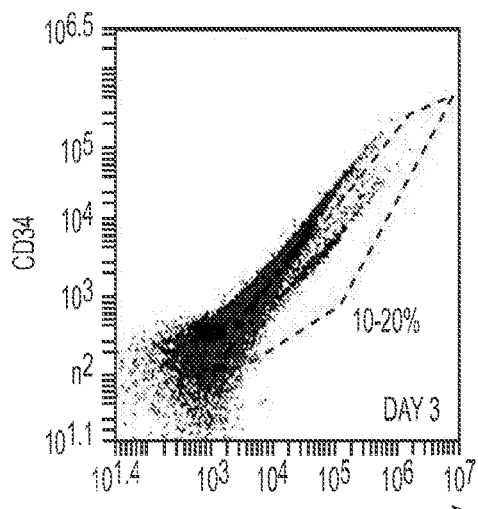
Figure 1L:
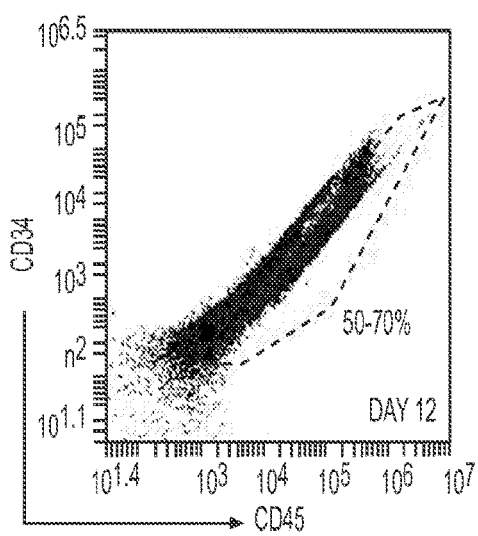
Figure 1M:
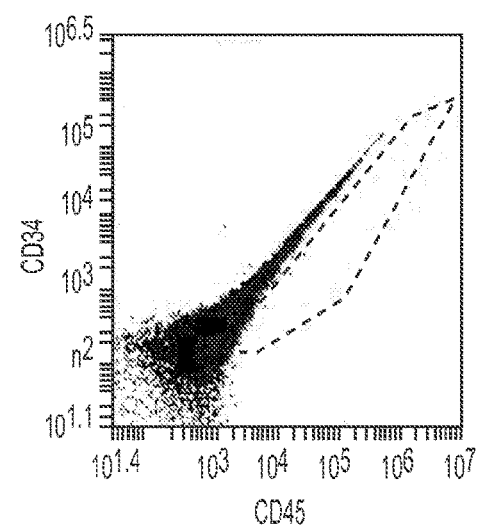
Figure 1N:
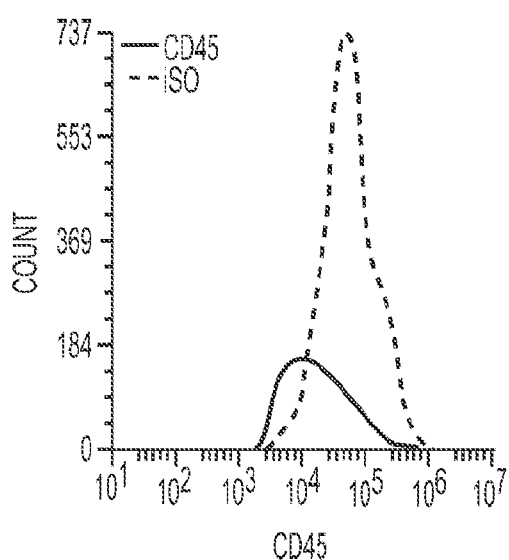
Figure 1O:
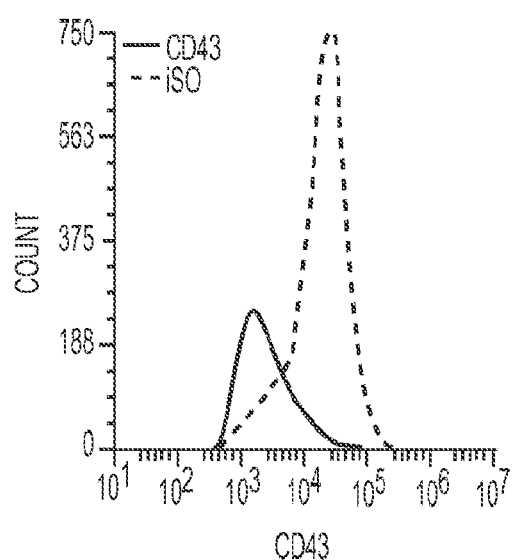
Figure 2:
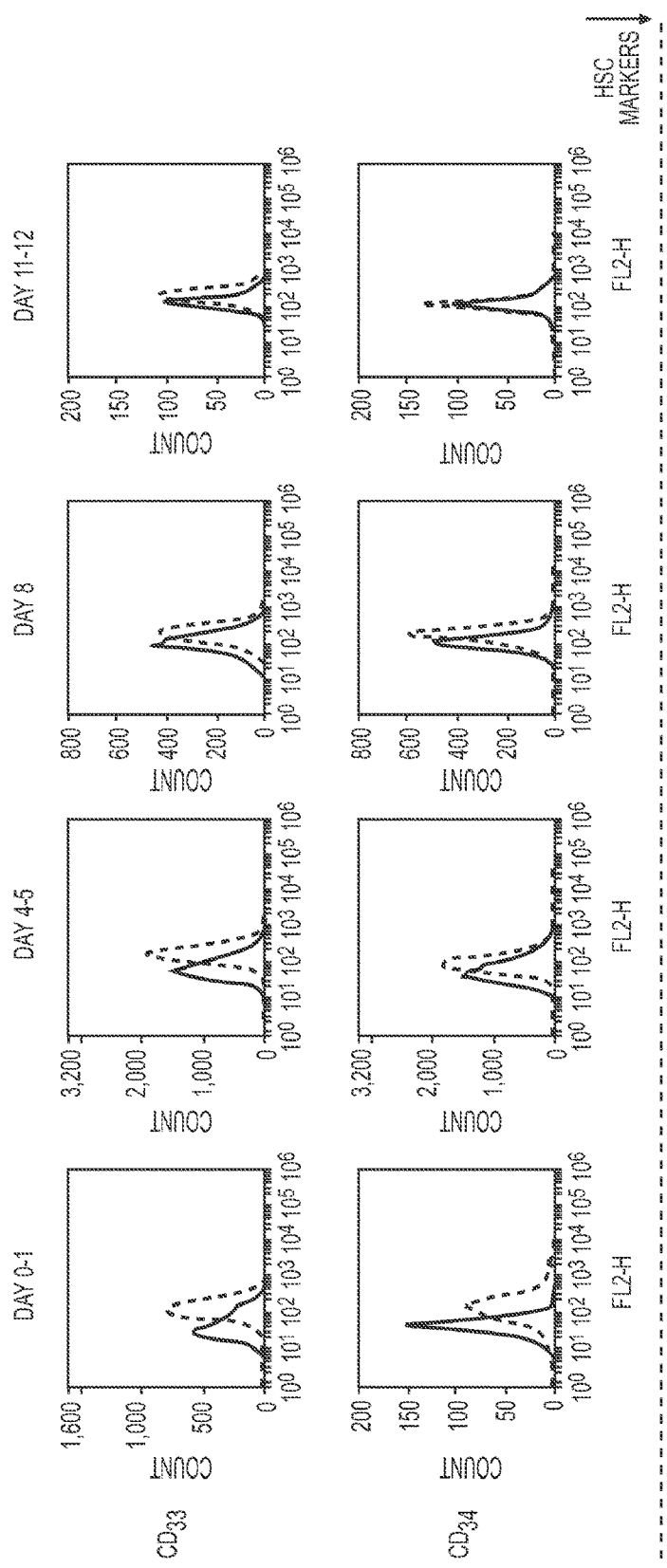
FIG. 2 exemplifies the decreasing expression of stem cell markers (HSC), and the increasing expression of myeloid markers over a twelve day period of HSC to common myeloid progenitors that is exemplified in FIG. 1. In the histograms, antigen and isotype controls are represented in red and black, respectively.
Figure 2:
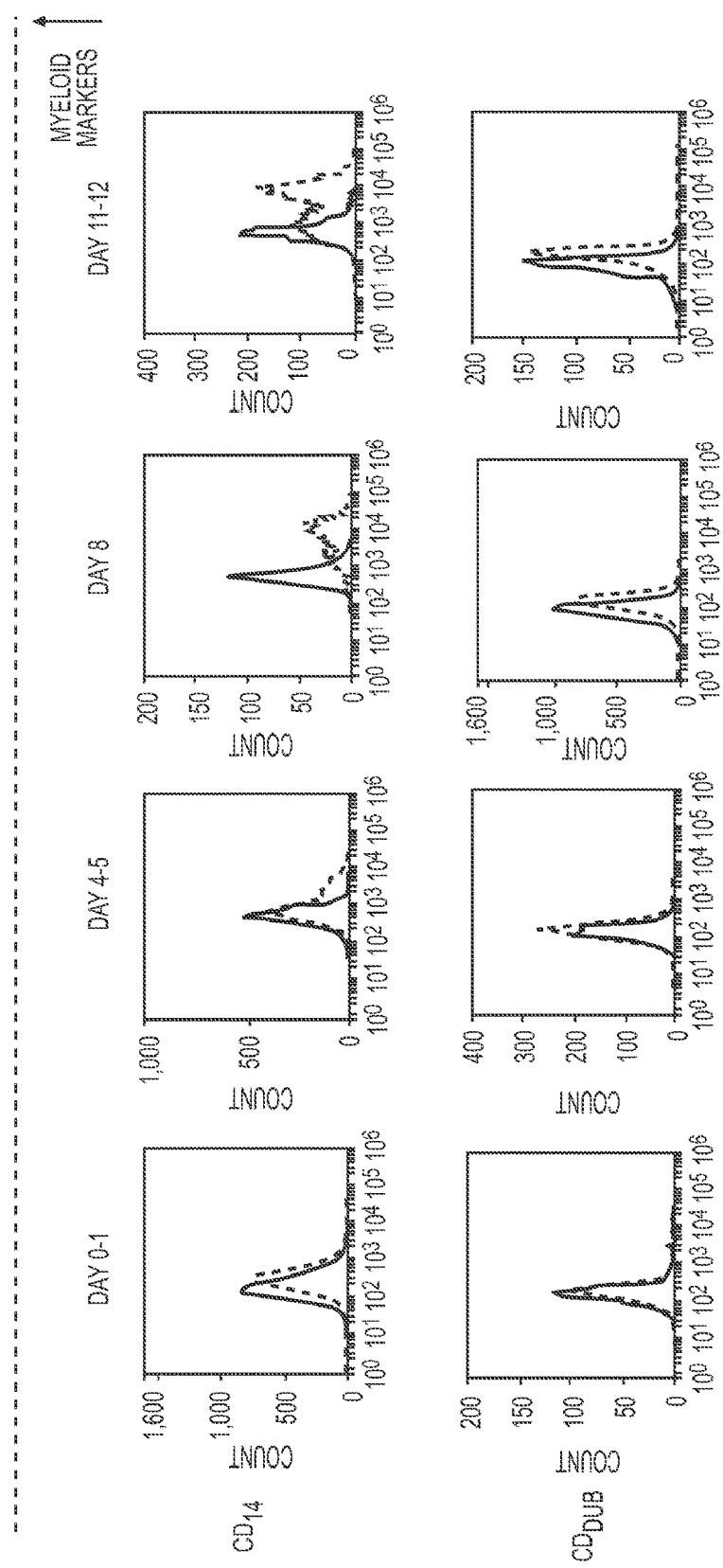

Differentiation of common myeloid progenitors. Myeloid cells were maintained in pHEMA-coated (Sigma) T25 flasks. To induce the differentiation of HSC into common myeloid progenitors (CMP), cells were treated with collagenase IV (1 mg/ml) in KnockOut DMEM/F-12 (Life Technologies) for 20 min at 37° C., followed by treatment with 0.05% trypsin-EDTA for 15 min at 37° C. Trypsin activity was quenched with 10% FBS, pelleted (300× g), resuspended in Myeloid differentiation medium (MDM), and plated in pHEMA coated flasks. Myeloid expansion was carried out for 10-12 days. MDM comprised α-MEM, 10% FBS, 100 ng/ml GM-CSF, 100 µM monothioglycerol. MDM was also used to expand myeloid cell numbers. Within one day of replating, differentiating CMP precursors reformed into clumps with pumpkin-shaped nuclei (FIG. 1G, H); after 3 days, the clumps began to break-up and single cells emerged (FIG. 1I). Surface expression of HSC markers, including CD34, decreased while CMP markers increased, including CD14, CD11b (SI 2), CD45 (FIG. 1J-N), and CD43 (FIG. 1O; FIG. 2).

Figure 3E:
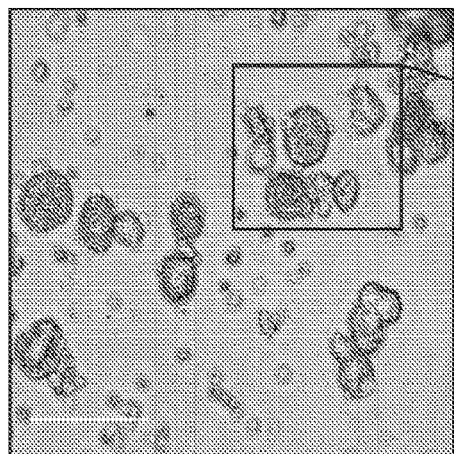
FIG. 3 exemplifies the morphology and functional activity of hESC-derived dendritic cells (DC)s, including: (A) After 10 days of culture with GM-CSF and IL-4 a significant proportion of cells differentiated into immature (i) DC, which were larger and brighter (arrows) than undifferentiated CMP (arrowheads); (B) Photomicrographs showing phagocytosis of carboxylate-modified red fluorescent latex beads (2 μm size) by iDC, and fluorescent overlay of bright field image showing fluorescent beads within iDC (arrows); (C) Dot plot of forward side scatter and side scatter (FSC/SSC) showing iDC with internalized beads; (D) Histogram of flow cytometry showing red fluorescent beads internalized by iDC (FL4 channel); (E) Image of iDC that were stimulated with TNF-α and LPS for 72 h; (F) Inset of cells boxed in B, arrows indicate long processes and mature DC morphology; (G) DIC image of mature DC shown using Hoffman optics; (H) Hematoxylin staining of mature DC showing long dendritic processes (arrows) and dark purple nuclei; (I) Flow cytometry showing DCsign immunostaining of iDC with (red) and without (blue) TNF-α and LPS induced maturation; (J) Flow cytometry of showing increased CD80+ immunostaining following DC maturation; (K) CD86+ immunostaining after TNF-α and LPS induced maturation; and (L) Surface expression of HLA-DR on mature DC.
Figure 3F:
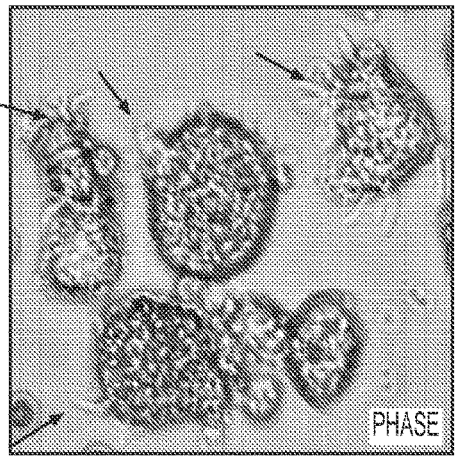
Figure 3G:
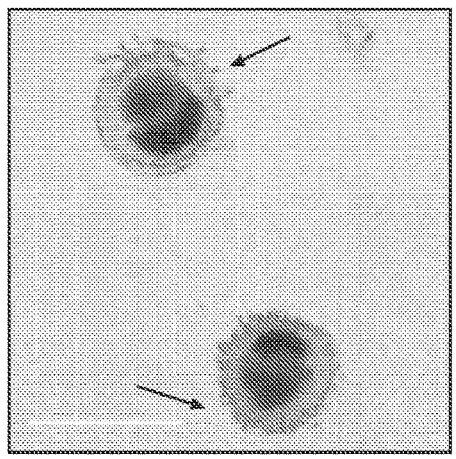

Generation of immature dendritic cells (iDC)s. For generating myeloid DC after myeloid expansion, cells were filtered by 70 µm strainer and fractioned with 25% Percoll® to remove dead cells and cell aggregates (FIG. 5A). Cells were rinsed with 5% FBS in PBS and replated in DC differentiation medium (DDM) for eight to ten days. DDM was Stem Span® SFEM medium (Stem Cell Technologies) supplemented with Ex-cyte® growth supplement (Millipore), 100 ng/ml GM-CSF, 100 ng/ml IL-4 (Endogen). Half the DDM volume of the iDC cultures were replaced every four days with fresh DDM. To expand the number of iDC, they were split and maintained under the same conditions. DC maturation was induced in DDM supplemented with TNF-α (100 ng/ml) and LPS (250 ng/ml) for three days. After eight days under DC differentiation conditions, iDCs had a wrinkled morphology (FIG. 3A) and showed surface expression of DCsign, CD80, and CD86 (FIG. 3I-K) An characteristic behavior of iDC is the phagocytosis of pathogens and cell fragments, which was assayed using human Ig-coated fluorescent latex beads (Dagenault et al., 2010). More specifically, carboxylate-modified red fluorescent latex beads with a mean diameter of 2 µm (L3030; Sigma) were opsonized in 50% human AB serum with PBS for 30 min. at 37° C. After that incubation, these opsonized latex beads were added to the DC cultures and incubated with gentle shaking for 30 min at 37° C. An identical control was incubated at 4° C. After 30 min., phagocytosis was halted by adding 2 ml of ice cold PBS, followed by washing the cells twice with ice cold PBS. DC were resuspended in 1 ml of cold PBS and fixed by adding an equal volume of 4% paraformaldehyde, and kept in the dark at 4° C. until imaging. The iDC internalized these beads (FIG. 3B) and flow cytometry showed a large proportion of iDC had phagocytosed beads (FIG. 3C, D).

Figure 3H:
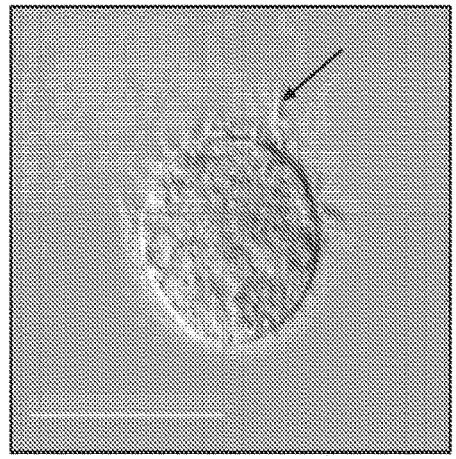

Maturation of dendritic cells. Immature DC were preloaded with peptides of interest prior to triggering maturation with DDM supplemented with 100 ng/ml TNF-α (PeproTech) and 250 ng/ml LPS (Sigma). Mature DC had branched dendritic processes that were observed with phase-contrast microscopy (FIG. 3E, F), light microscopy of Hematoxylin and eosin (H&E) staining (FIG. 3G), and DIC microscopy (FIG. 3H). H&E staining was performed using fixed cells (2% paraformaldehyde) that were spread onto glass slides by Cytospin. Slides with iDCs and mature DCs were covered by H&E solution and incubated for 15 min., followed by treatment with acid and bluing solutions (Vector Laboratories). Slides were rinsed with water, run through and alcohol series (50%, 70%, 95%, 100% ethanol) and coverslips were mounted with Permount (Fisher). Images of H&E staining were captured with a color CCD camera mounted on a Nikon® microscope.

Figure 3I:
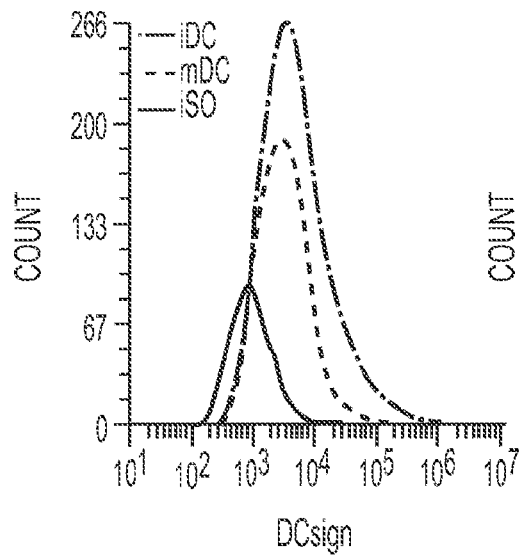
Figure 3J:
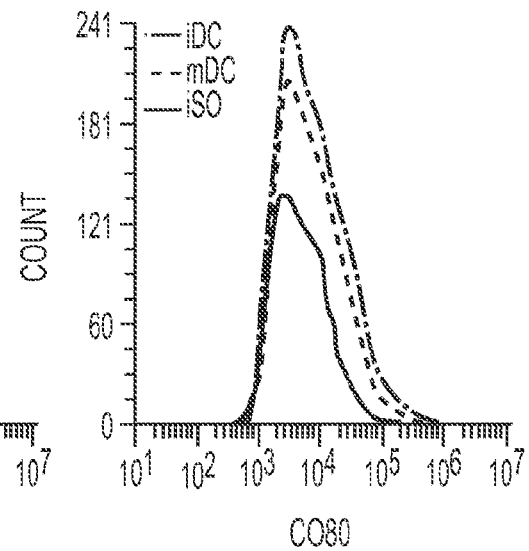
Figure 3K:
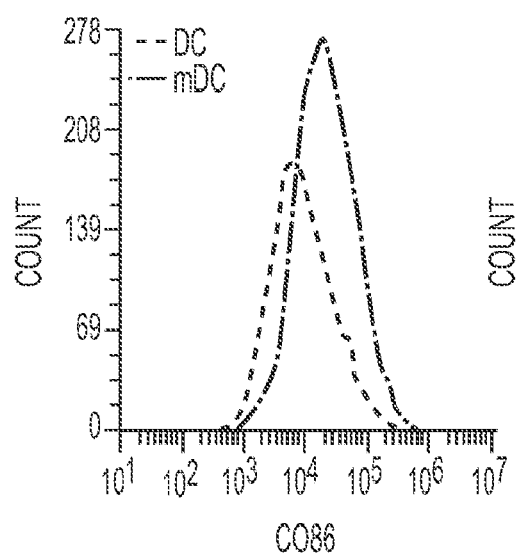
Figure 3L:
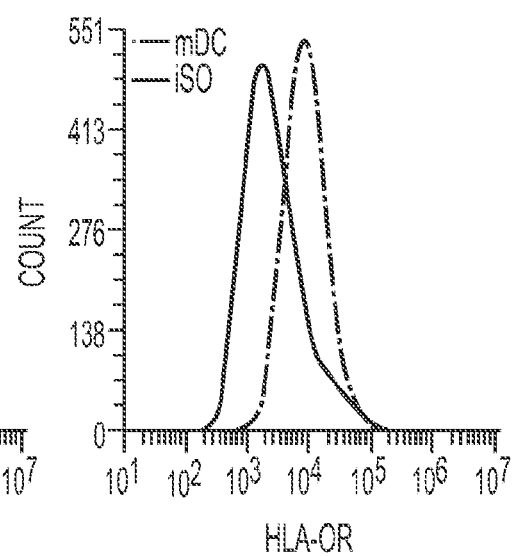
Figure 4:
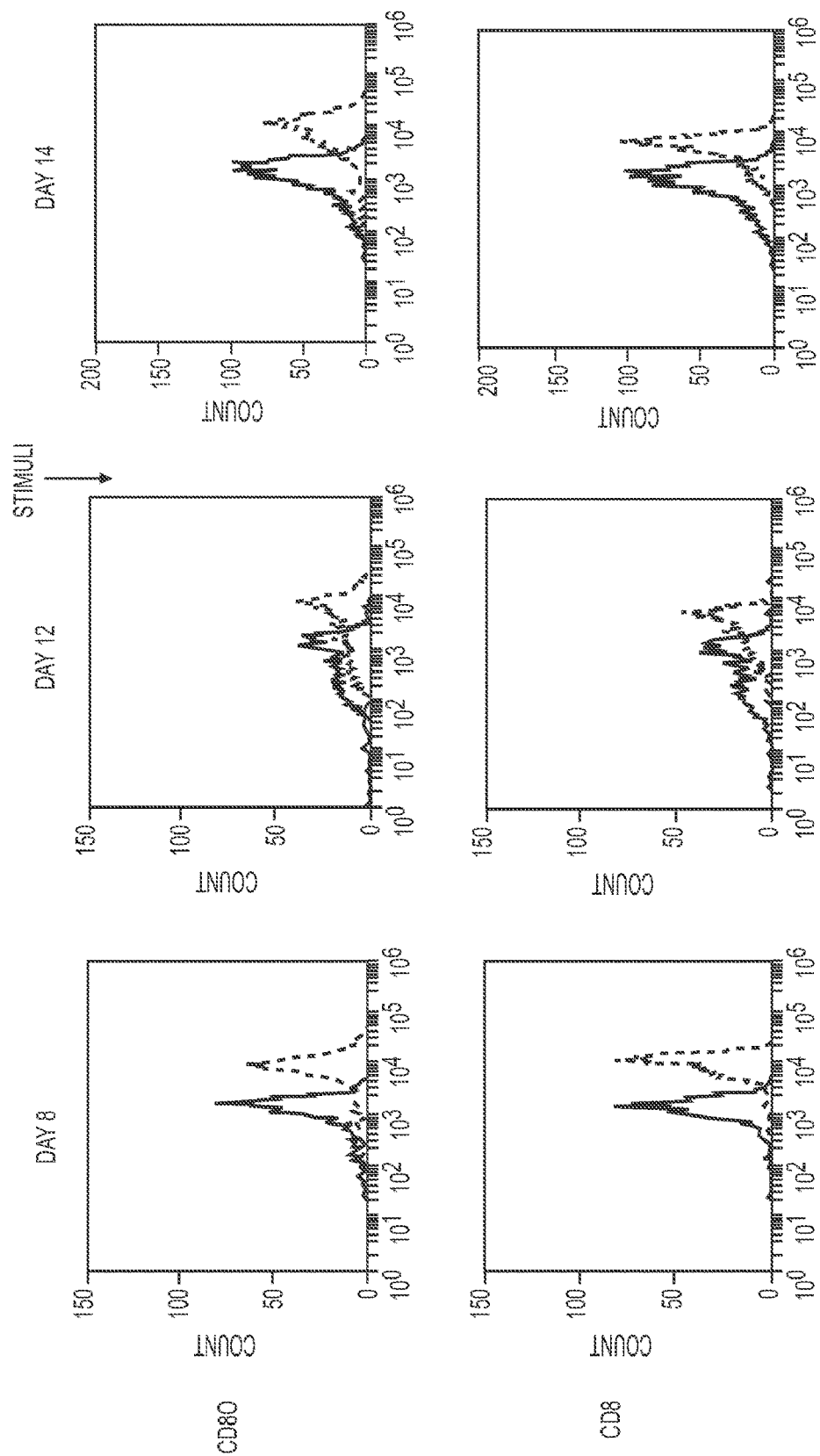
FIG. 4 exemplifies flow cytometry results showing expression of DC markers during CMP to DC differentiation on days eight, twelve, and fourteen. DC maturation factors were given at day twelve. In the histograms, antigen and isotype controls are represented in red and black, respectively.
Figure 4:
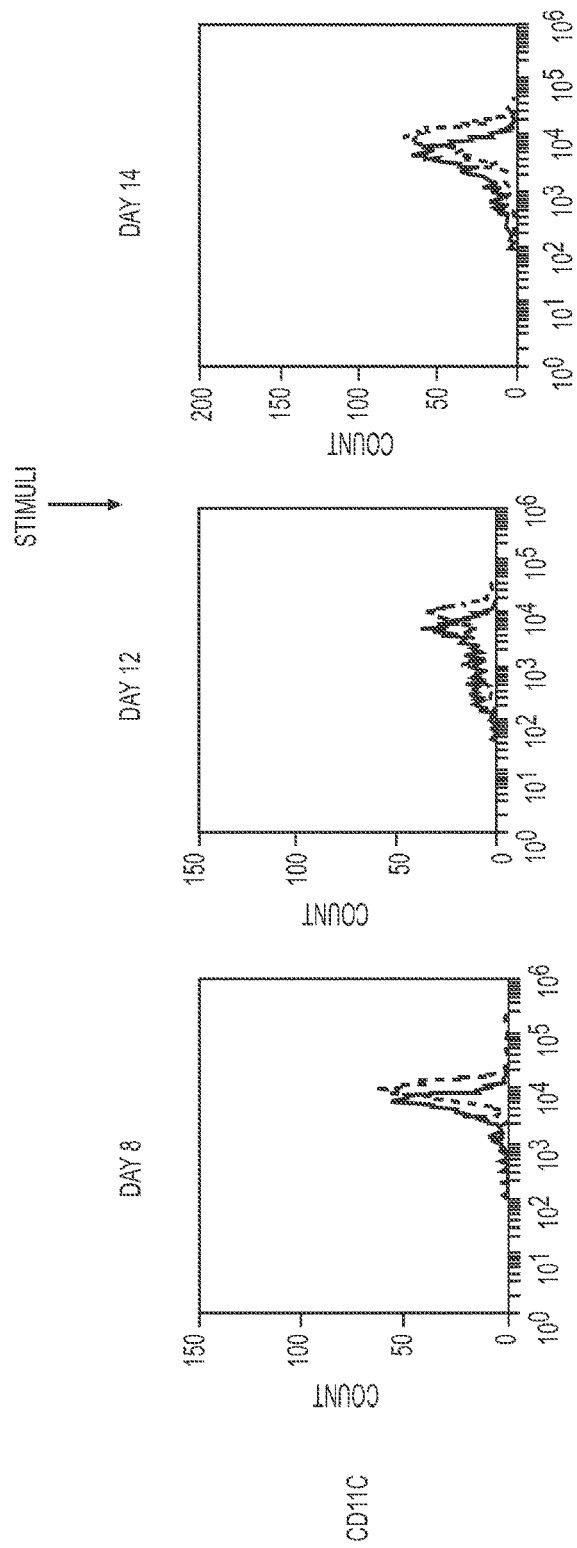
Figure 5E:
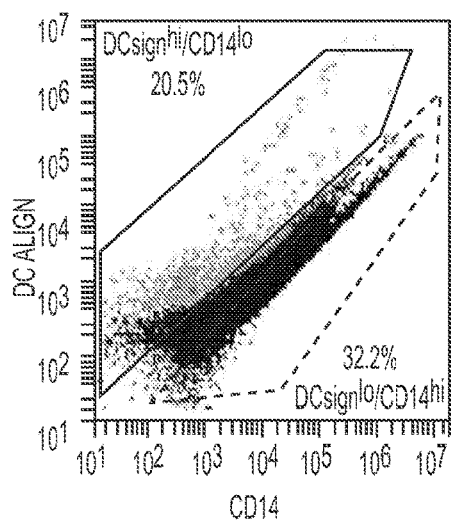
FIG. 5 exemplifies that hESC-derived DC require two populations to form islands of activation (IOA), including: (A) Schematic of the protocol used to process DC for co-culture with T cells; (B) Flow cytometry dot plot of iDC showing population gated on FSC/SSC dot plot; (C) DCsign/FSC plot of population gated in B, Q1-UR (42.8%) are DCsign+ cells. (D) CD14+/FSC dot plot of population gated in (B), Q5-UR (51.3%); (E) Dot plot of DCsign:CD14 showing ratio of CD14$^{lo}$/DCsign$^{hi}$ to CD14$^{hi}$/DCsign$^{lo}$ at 1:1.5, defined as proportionally balanced DC; (F) Photomicrograph of DC mixed with maturation factors, showing islands of activation (IOA); (G) High magnification bright field image of IOA; (H) Phase-contrast image of IOA, note thin rim; (I) DC purified with anti-CD14 magnetic microbeads did not include the DCsign$^{hi}$/CD14$^{lo}$ population, (J) and did not form IOA; (K) DC purified with anti-DCsign MACS microbeads did not include the DCsign$^{lo}$/CD14$^{hi}$ population, and (L) and did not form IOA.

Flow cytometry confirmed that both iDC and mature DC expressed DCsign (FIG. 3I). More particularly, cultures of iDC that were purified with Percoll separation (FIG. 5A), contained populations that expressed high levels of DCsign (FIG. 5B, C) or CD14 (FIG. 5D). One population was DCsign$^{hi}$/CD14$^{lo}$ and another population was DCsign$^{lo}$/CD14$^{hi}$ (FIG. 5E). These populations were typically in a ratio of about 1:1.5, respectively. For proportional balancing studies iDC were purified using anti-CD14 or anti-DCsign magnetic beads. Briefly, DC were filtered with 70 µm strainer to remove aggregates and purified with myeloid dendritic cell kits for separating CD14 expressing cell followed by the MACS column (Miltenyi) purification. Isolated cells were cultures for four weeks in DDM. To enrich for isolation of DCsign$^{hi}$ cells, we used a human DCsign kit (Miltenyi) to purify the cells and they were also expanded for four weeks in DDM.

Figure 5F:
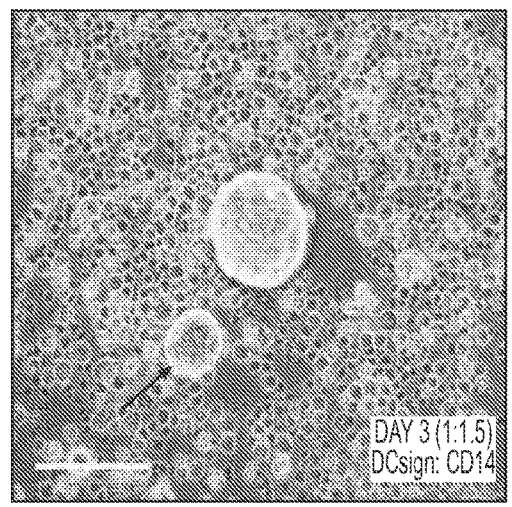
Figure 5G:
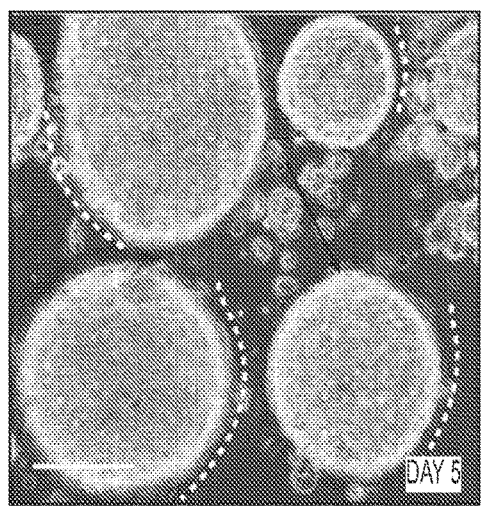
Figure 5H:
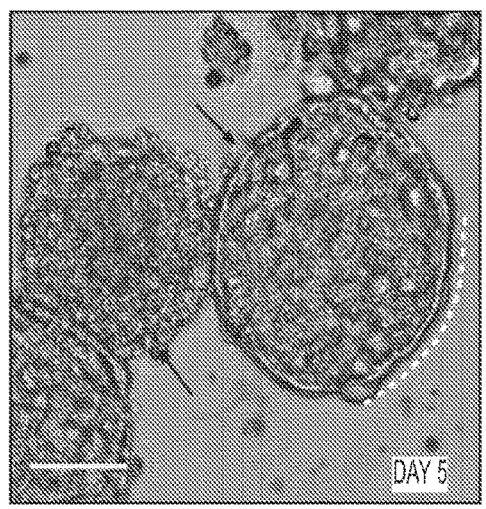

When mature DCs were mixed with primary T cells, the cultures developed aggregates of cells within three to five days, referred to as "Islands of activation" (IOA) (FIG. 5F-H) IOA were imaged by first fluorescently labeling DC incubating them in pre-warmed serum-free media containing DiI (2 µM, Life Technologies) for 20 min at 37'C, and isolated T cells were labeled with DiO (1 µM) in the same manner. After incubation, 10× volumes of T cell medium was added and cells were pelleted at 300× g for 5 min. Cells were then washed twice with 0.1% BSA in PBS. Fluorescently labeled DCs (red) and T cells (green) were mixed and cultured in a pHEMA-coated flask overnight (16 h), then fixed by adding an equal volume of 4% paraformaldehyde and let stand for 30 min. Nuclei were labeled with DAPI by adding it directly to the fixing solution (20 µM final). The cells were not washed as centrifugation and resuspension may disrupt the IOA, so IOA were picked with a microscope and placed in a cover glass bottomed chamber for imaging. Images of IOA were captured with a Nikon® C1 confocal microscope.

Purification of iDCs with anti-DCsign magnetic beads enriched the DCsign$^{hi}$/CD14$^{lo}$ population and removed most of the DCsign$^{lo}$/CD14$^{hi}$ population (FIG. 5I), but prevented the formation of IOA (FIG. 5J). Complementary studies, enriching for DCsign$^{lo}$/CD14$^{hi}$ cells with anti-CD14 magnetic beads, reduced the DCsign$^{hi}$/CD14$^{lo}$ population (FIG. 5K) and also prevented the formation of IOA (FIG. 5L).

Flow cytometry also confirmed that both iDC and mature DC expressed CD80 (FIG. 3J), CD86 (FIG. 3K), and CD11c (FIG. 3). The HLA class II complex is sequestered in the endosomes of iDC, and traffics to the surface as DC mature (FIG. 3L).

Figure 6I:
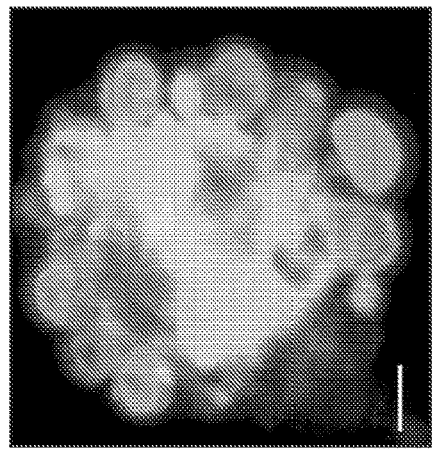
FIG. 6 exemplifies the purification of CD4+ T cells and stimulation with mature DC, including: (A) Schematic diagram outlining the purification of T cells from whole blood; (B) Dot plot (FSC/SSC) of flow cytometry showing gated T cell population, and (C) histogram showing anti-CD4 immunostaining of gated population; (D) Low magnification photomicrograph of purified T cells showing uniform morphology; (E) Histogram showing CFSE immunostaining of CD4+ T cells at Day 0 and (F) ten days after co-culture with DC and IL-2, which show that the fluorescence of daughter cells is halved with each cell division, as indicated by the red number at each cells division from 1-7; (G) Photograph of an Island of activation consisting of DiI-labeled T cells and DC; (H) Nuclear staining of cells with DAPI, pseudocolored red for contrast, showing large DC nuclei in the middle and small T cell nuclei around the perimeter; (I) Merged images of (G) and (H); (J) Histogram of CFSE fluorescence in CD4+ T cells that were incubate with IL-2 and DC from a standard preparation, and (K) a DCsign-purified preparation, and (L) a CD14-purified preparation.
Figure 6H:
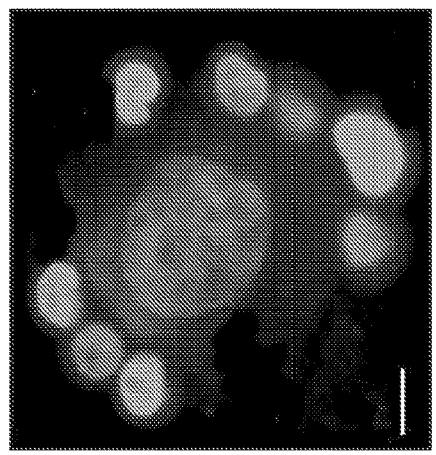
Figure 6G:
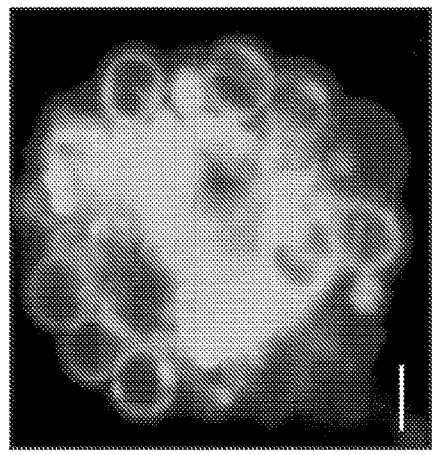
Figures 6J, 6K, 6L:
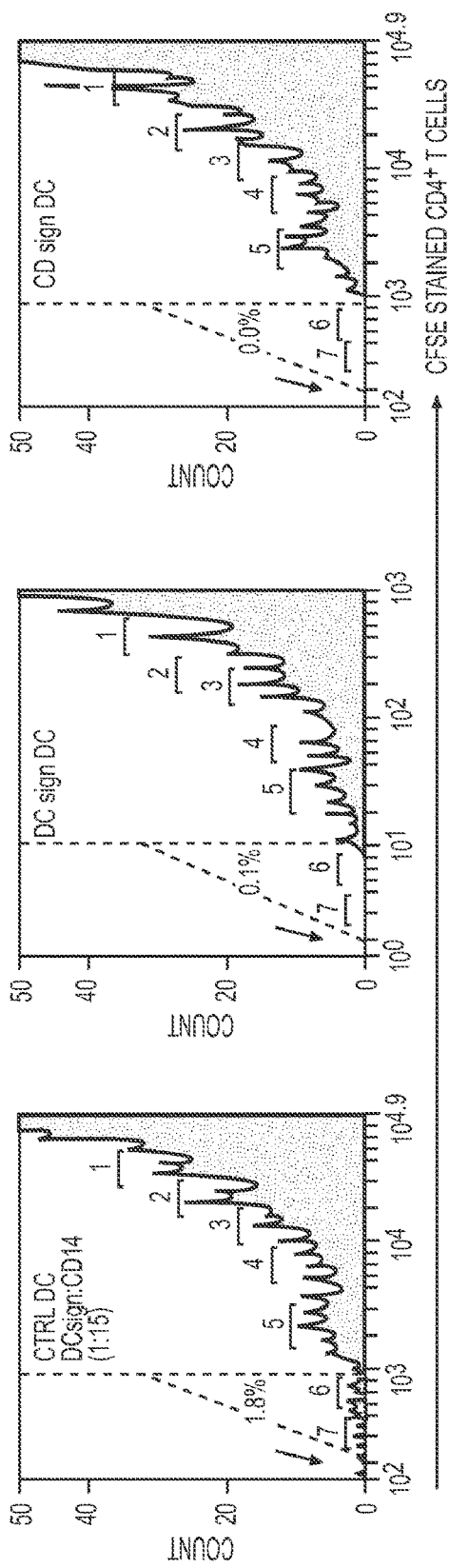

To determine if hESC-derived DC could stimulate T cell proliferation, human T cells were isolated from whole blood (FIG. 6A), labeled with CFSE, and co-cultured with antigen-loaded mature DC for seven to ten days. Afterwards, CD4$^+$ T cells were immunostained with anti-CD4 and proliferation was assessed by CFSE fluorescence of the CD4$^+$ population (FIG. 6B, C). T cells (FIG. 6D) incubated with DC and IL-2 (Life Technologies) were used as positive controls to determine CFSE fluorescence of serial cell divisions (FIG. 6E, F). To examine IOA, we fluorescently labeled T cells with lipophilic DiI before mixing them with mature DC. The next day, IOA could be seen with T cells surrounding larger DC (FIG. 6G-I). T cells mixed with mature DC and IL-2 proliferated for up to 7 generations (FIG. 6J), but only five generations of proliferation occurred with DC that had been purified with anti-DCsign (FIG. 6K) or anti-CD14 (FIG. 6L) magnetic beads.

hESC-derived DCs stimulate influenza HA peptide-specific CD4$^+$ T cell proliferation. T cells were collected from 20 mL whole blood samples drawn from human subjects before and one week after receiving a commercial influenza vaccine (FLULAVAL®, distributed by GlaxoSmithKline) by intramuscular injection. The whole blood was drawn from subjects in EDTA containing blood tubes (#366643, BD Biosciences). Under sterile conditions the blood sample was diluted to 1:1 with PBS, and 40 mL of the diluted sample layered on top of 30 mL of Ficoll-hypaque®, and spun at 400×g for 30 min. The peripheral blood lymphocyte (PBL) layer was collected (FIG. 6A) and diluted with PBS (1:7) followed by the centrifugation at 300×g for 10 min. Cells were rinsed twice more by resuspending pellets in PBS. Viable cells were counted by trypan blue exclusion. Adherent cells were removed to enrich for T cells using nylon wool columns. Briefly, the nylon wool column was washed with T cell medium (1640 RPMI with 10% FBS) and incubated at 37° C. for one hour. Then, $10^7$ cells/ml of PBL were added to the pre-warmed column and incubated for one hour at 37° C., after which non-adherent cells were collected by opening the column's stopcock. The column was washed twice with five ml of T cell medium to collect total effluent. T cell enriched fractions were incubated with CFSE solution (4 µM in PBS) for 8 min at 37° C. water bath. After incubation, the solution was diluted with 10 volumes of T cell medium, pelleted by centrifugation (300×g, 10 min) and washed twice with PBS containing 0.1% BSA. CFSE labeled cells were resuspended, counted, and a fraction was used to evaluate CFSE fluorescence by flow cytometry (Accuri®, BD Biosciences). Prior to flow cytometry cells were immunostained with Alexa®647-conjugated anti-CD4 antibody (BD Biosciences), to allow for analysis of CFSE fluorescence in the CD4$^+$ population. Further flow cytometric data and histogram analyzed was done by FCS express 4 flow cytometry software (De Novo Software).

CFSE-labeled T cells were co-cultured with mature DC that had been pre-loaded with the influenza HA immunogenic peptide (amino acids 126-138, H-HNTNGVTAAC-SHE-OH, Anaspec). (Le Nouën et al., 2010; Schmidt et al., 2012). Peptide loading of the DCs involved resuspending lyophilized influenza HA peptide in water and a one-tenth volume of 10×PBS to neutralize the pH. Immature DCs were loaded with influenza peptide at a final concentration of 10 micrograms per mL in culture medium for 4 days in a humidified 5% $CO_2$ incubator. Immature DCs were then matured with TNF-alpha and LPS as before.

Analysis of CD4$^+$ T cell proliferation showed little response to control DC in pre-vaccine samples (FIG. 7A), but post-vaccine samples showed a marked increase in CD4$^+$ T cell proliferation (FIG. 7B, C), likely due to non-specific effects of adjuvant in the vaccine (Fox et al., 2012; Tetsutani et al., 2012; Caproni et al., 2012). Mature DC that were pre-loaded with Influenza peptide also had little stimulatory effect on pre-vaccine CD4$^+$ T cells (FIG. 7A), but post-vaccine T cells responded with increased proliferation that was well above their responses to control DC (FIG. 7B-E). The only difference between control DC and influenza-DC used in post-vaccine assays was preloading of the influenza peptide, suggesting the increase was due to the proliferation of influenza-specific CD4$^+$ T cells.

Briefly, all procedures involving human subjects were performed under approved Institutional Review Board Protocols from the Western University of Health Sciences (Pomona, Calif.), Arrowhead Regional Medical Center (Colton, Calif.), and Casa Colina (Pomona, Calif.). Informed consent forms were explained to all participants and signed by all subjects, and/or legal guardians.

Example 2

Analysis of Alzheimer's Patients' Aβ-Specific CD4$^+$ T Cell Response

To evaluate if hESC-derived DC could detect CD4$^+$ T cell responses in chronic conditions we recruited six subjects with a presumptive diagnosis of Alzheimer's disease (AD) and three age-matched controls. Whole blood was collected, processed, and T cells isolated according to the same methods described in Example 1. CD4$^+$ T cell proliferation was evaluated in response to mature DC that were pre-loaded with 10 mg/ml of Aβ1-42 peptide (BioMer Technology) according to the same method for loading DCs described above for influenza HA peptide.

Figures 7C, 7D:
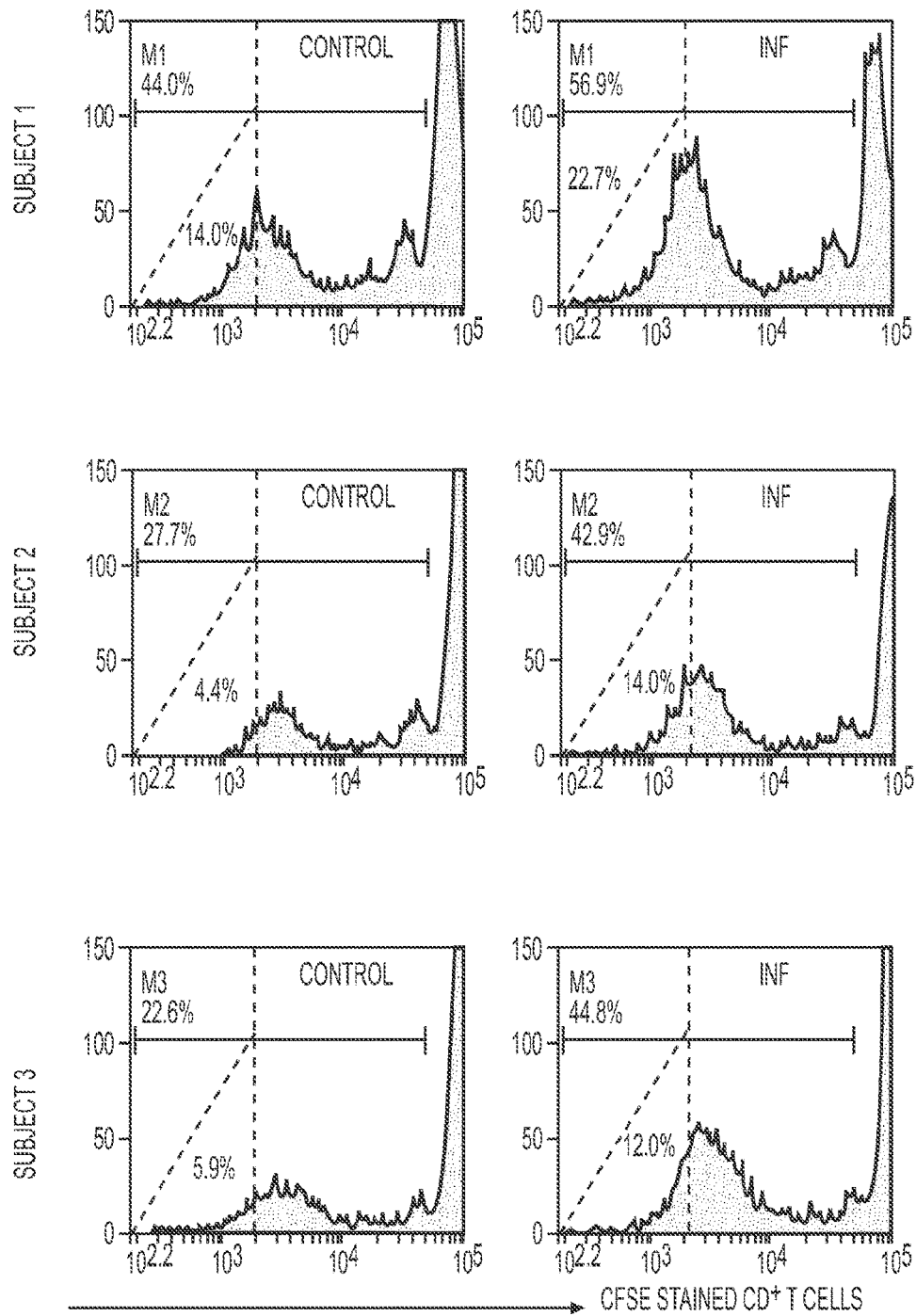
FIG. 7 exemplifies an analysis of DC-induced T cell proliferation, including: (A) Three histograms showing CFSE fluorescence of CD4+ T cells isolated from human subjects (Subject 1-3) prior to vaccination, and that had been co-cultured with hESC-derived DC that had been pre-loaded with Influenza peptide (INF, blue) or no peptide (ctrl, red); (B) Three histograms showing CFSE fluorescence in CD4+ T cells isolated from the same subjects one week after receiving an influenza vaccine, and that had been co-cultured with DC that were pre-loaded with Influenza peptide (INF, blue) or no peptide (ctrl, red); (C) Three histograms of CFSE fluorescence of post-vaccine CD4+ T cells co-cultured with control DC (control), in which dashed lined indicates fifth cell division as calculated from companion cultures that contained IL-2; (D) CFSE fluorescence of post-vaccine CD4+ T cells co-cultured with DC that were pre-loaded with Influenza peptide (INF); (E) Bar graph showing relative proliferation (divisions five to seven) of CD4+ T cells in three human subjects before (pre-) and after (post-) receiving an Influenza vaccine. White bars indicate CD4+ T cell proliferation in cultures that contained Influenza peptide pre-loaded DC (INF); black bars indicate CD4+ T cell proliferation in cultures that contained DC not loaded with peptide (ctrl); (F) Bar graph showing CD4+ T cell proliferation (five to seven divisions) in three control subjects (c1-3) and six subjects with a presumptive diagnosis of Alzheimer's disease (AD 1-6). White bars indicate CD4+ T cell proliferation (five to seven divisions) in cultures that contained DC pre-loaded with human Aβ 1-42 peptide; black bars indicate CD4+ T cell proliferation (five to seven divisions) in cultures that contained DC that were not pre-loaded with peptide.
Figure 7E:
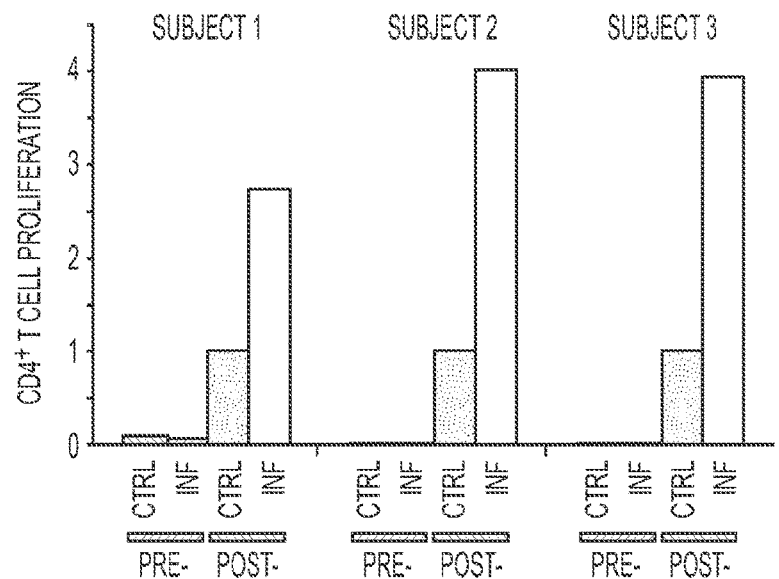
Figure 7F:
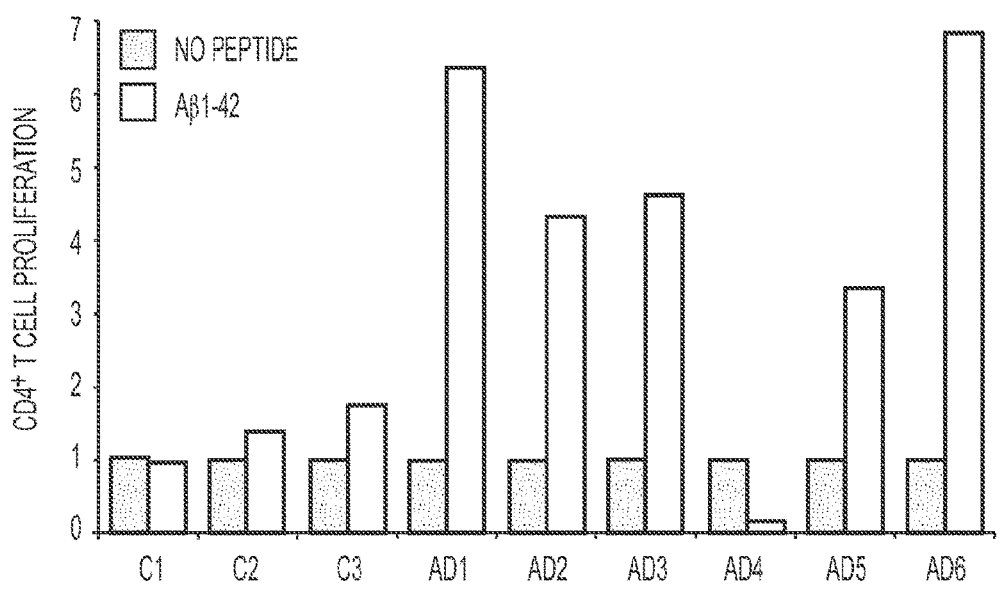
Figure 8:
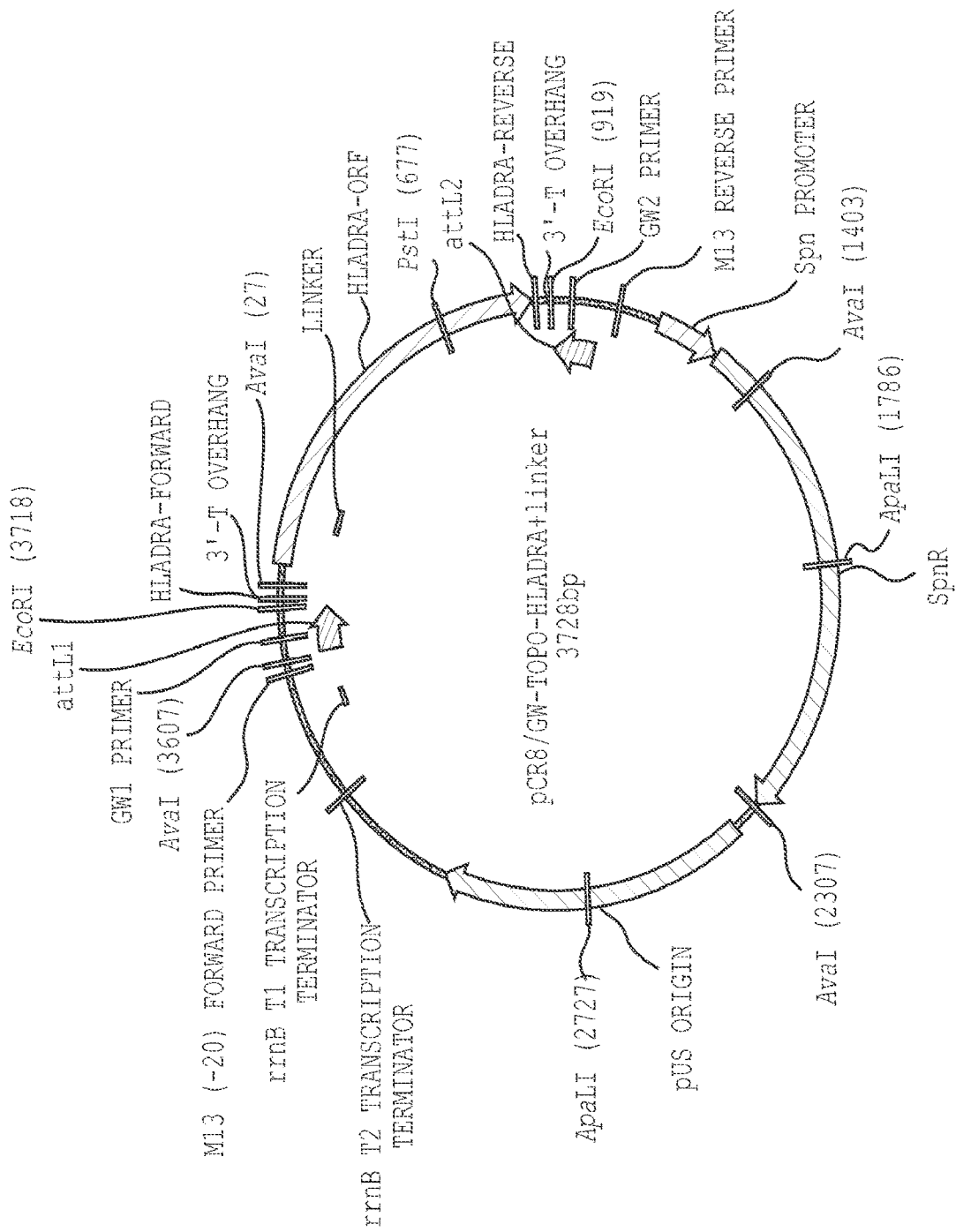
FIG. 8 shows a plasmid map of the pCR8/GW-TOPO-HLADRA+linker vector.
Figure 23:
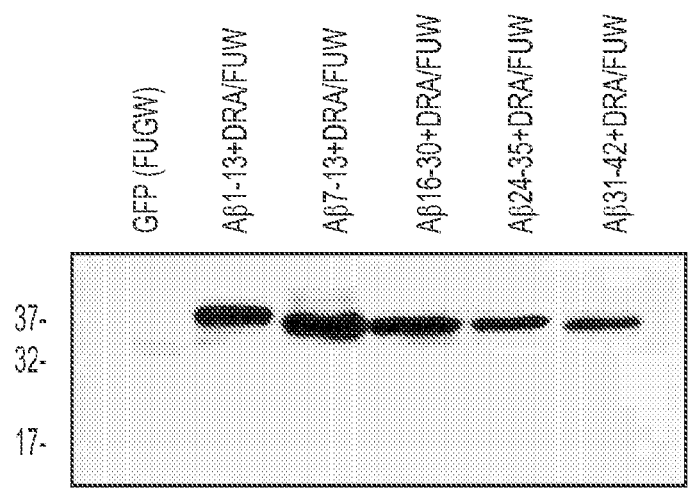
FIG. 23 shows a Western blot of cell lysates from 293 cells that were infected with lentiviruses that were engineered to express either green fluorescence protein (GFP), which served as the vector control (Lane 1), and each of the following HLA-DRA/Aβ fusion proteins, respectively: HLA-DRA/Aβ 1-13 (Lane 2); HLA-DRA/Aβ 7-13 (Lane 3)p; HLA-DRA/Aβ 16-30 (Lane 4); HLA-DRA/Aβ 24-35 (Lane 5), and HLA-DRA/Aβ 31-42 (Lane 6).
Figure 24:
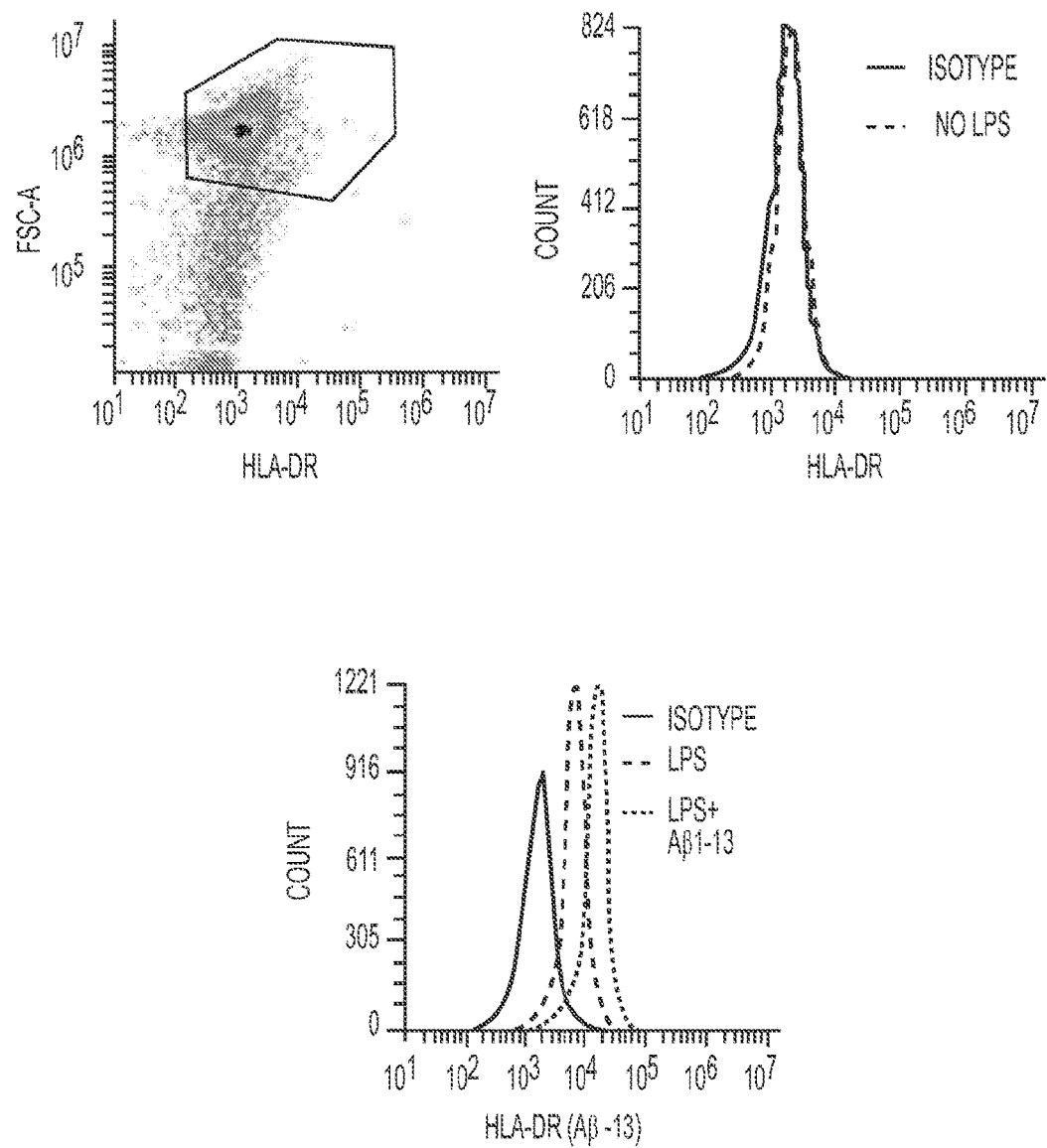
FIG. 24 shows the surface expression of recombinant HLA-DRA constructs that are expressed in the human dendritic cell line, KG-1. Top left shows a FDC/SSC scatter plot of KG-1 cells with gating indicated. The top middle panel shows anti-HLA-DRA immunostaining of KG-1 cells without stimulation. The top right panel shows anti-HLA-DRA immunostaining of KG-1 cells after LPS stimulation. Control cells (red) exhibited less HLA-DRA staining than cells infected with lentivirus that expressed HLA-DRA/Aβ 7-13 (blue). Isotype control staining is indicated in black for all plots. The lower four plots show similar increases in HLA-DRA immunostaining of KG-1 cells that were infected with lentivirus vector containing the HLA-DRA/Aβ 7-13, HLA-DRA/Aβ 16-30, HLA-DRA/Aβ 24-35, and HLA-DRA/Aβ 31-42, as indicated.
Figure 25A:
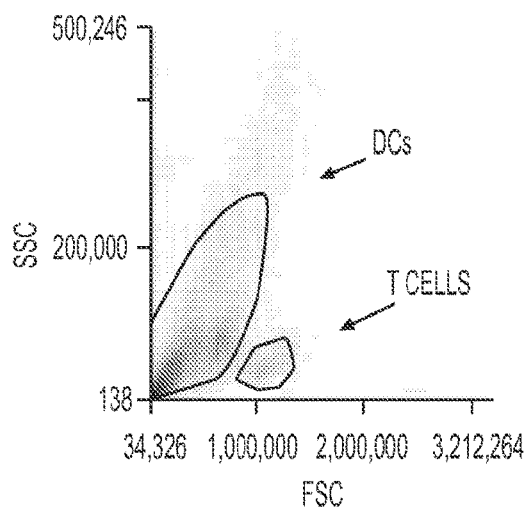
FIG. 25 shows: (A) a FSC/SSC scatter plot that indicates hESC-derived myeloid dendritic cells (DCs) and T cells that were isolated from fresh blood sample(s) were detected in a mixture of those cells. Prior to flow cytometer analysis, the T cells were prelabled with CFSE, then mixed with the DC, and then all the cells in the mixture were stained with fluorescently-conjugated anti-CD4. The fsc/ssc in this step is to separate potential T cells from the other population—including DC and non-DC—that was gated out. We are not proving they are DC. Fluorescently labeled CD4+ cells were gated from a smaller subset. Not all detection events in the DC population were actually DCs; (B) a T cell-gated FSC/SSC scatter plot of only the CD4+ T cell population shown in (A); (C) a scatter plot of CFSE fluorescence on the x-axis and anti-CD4 on the y-axis of the CD4+ T cell population described in (B), showing T cells that had divided (i.e., proliferated), contained less CFSE, and thus, by the population of cells that is represented on the left side of the plot, and at the beginning of the experiment there was no measurable proliferation and therefore no cells on the left; (D) shows a scatter plot as shown in (C), except that the mixture of T cells and DCs were cultured together for ten days prior to analysis either under control conditions (T cells cultured with DCs that did not express a HLA-DRA(Ab) construct, or under test conditions (T cells cultured with DCs that did express a HLA-DRA(Ab) construct). The control cell population, which is represented as green events, had 2.6% of their total population of CD4+ T cells depicted on the left side of the plot, i.e., the side of the plot that shows divided cells. The experimental cell population, which is represented as red events, had 3.8% of their total population of CD4+ T cells depicted on the left side of the plot. The difference between 3.8 and 2.6 indicates an Aβ-specific T cell population.
FIG. 25(E) shows FSC/SSC scatter plots of CFSE fluorescence on the x-axis and anti-CD4 on the y-axis of the CD4+ T cell populations that had been infected with lentivirus that had been engineered to express HLA-DRA constructs that either contained full-length Aβ, A1 (Aβ1-13), B2 (Aβ7-13), C3 (Aβ16-30), D4 (Aβ24-35), or E5 (Aβ1-42), respectively.
Figure 25B:
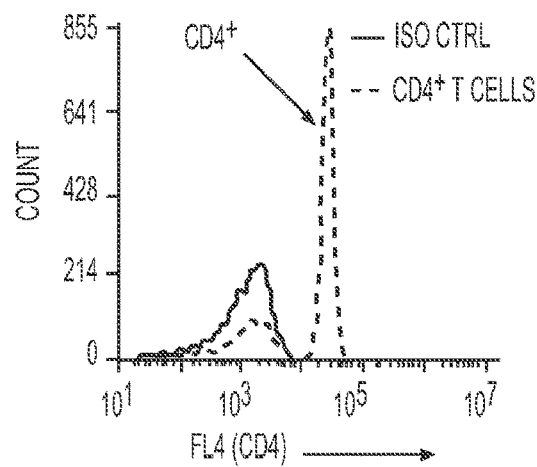
Figure 25C:
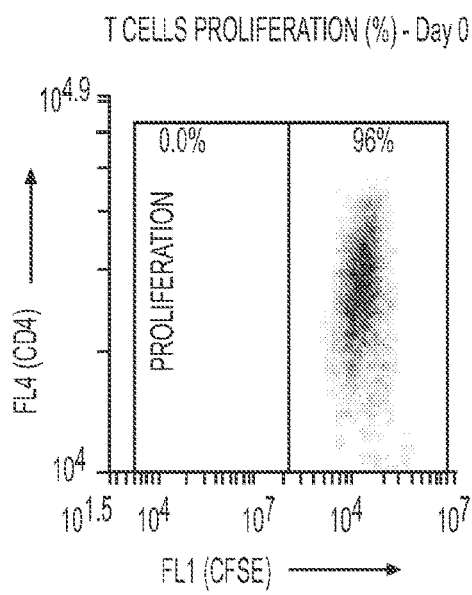
Figure 25D:
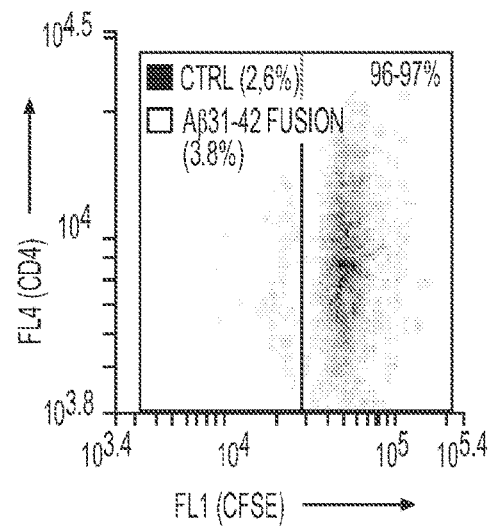
Figure 26:
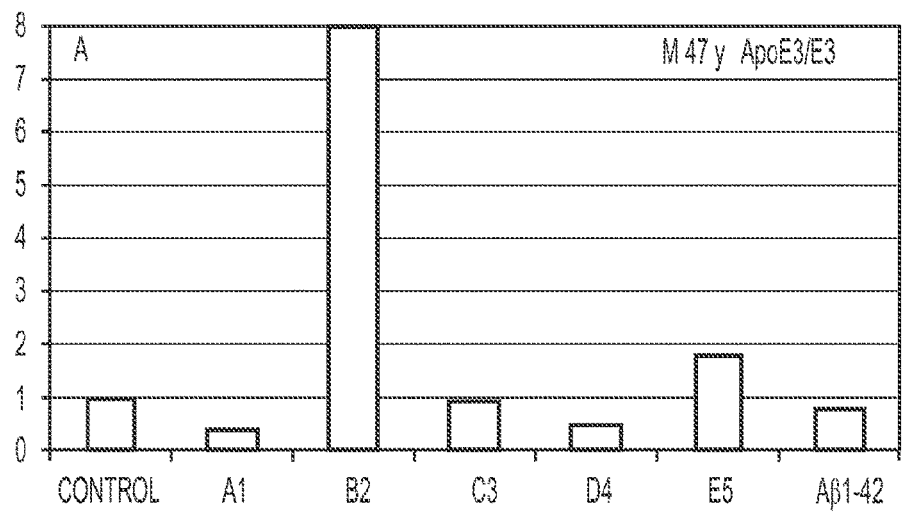
FIG. 26 shows bar graphs of cell proliferation responses of CD4+ T cells that that had been isolated from the blood of a 47 year old male with an ApoE3/E3 genotype, and no signs of dementia. The CD4+ T cells were co-cultured with hESC-derived DCs that had been infected with lentivirus that had been engineered to express HLA-DRA constructs that either contained HLA-DRA only (the control), A1 (Aβ1-13), B2 (Aβ7-13), C3 (Aβ16-30), D4 (Aβ24-35), or E5 (Aβ1-42), respectively. Bars represent the proportions of cells that underwent five or more cell divisions, i.e., indicative of a sustained and specific proliferative response.
Figure 27:
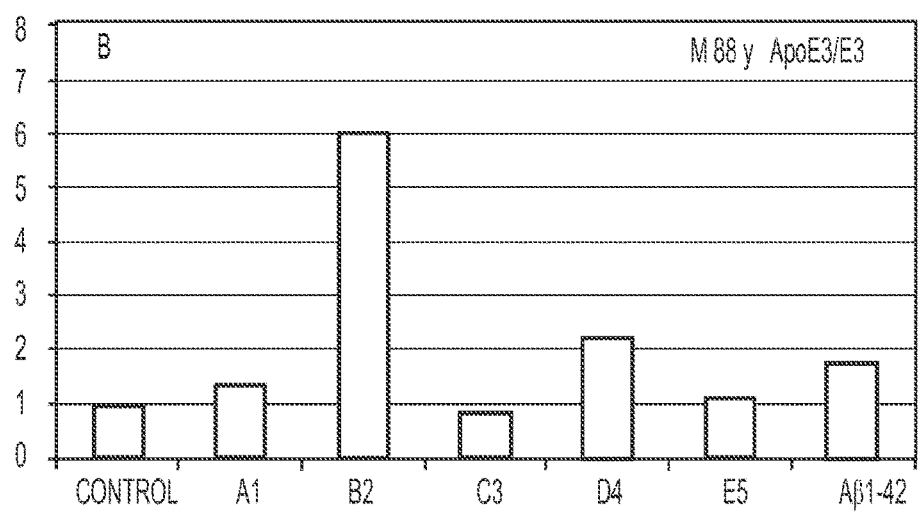
FIG. 27 shows the same type of data shown by FIG. 26, except that the blood donor was an 88 year old male with an ApoE3/E3 genotype, and no signs of Alzheimer's disease.
Figure 28:
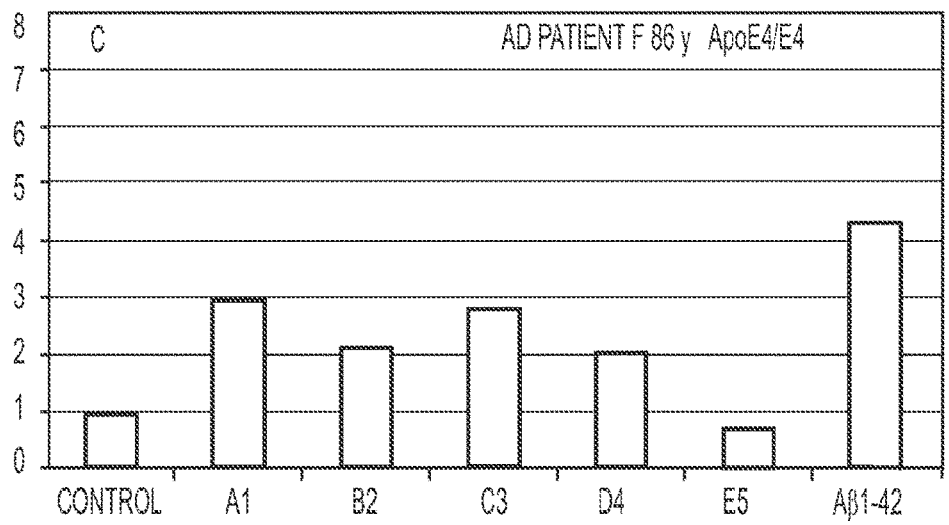
FIG. 28 shows the same type of data shown by FIG. 26, except that the blood donor was an 86 year old female with an ApoE4/E4 genotype, that had been diagnosed with Alzheimer's disease for 14 years.
Figure 29:
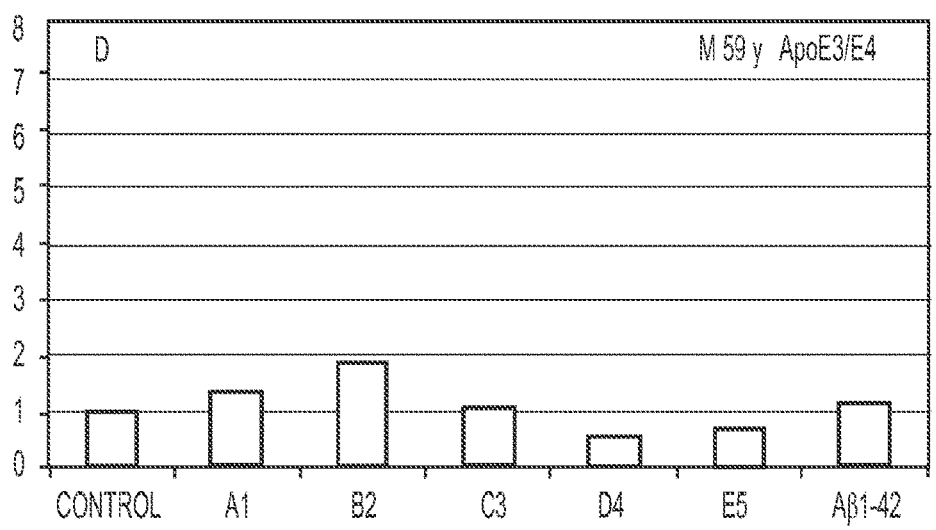
FIG. 29 shows the same type of data shown by FIG. 26, except that the blood donor was a 58 year old female with an ApoE3/E4 genotype, and the daughter of a mother with advanced Alzheimer's disease. The donor is the sister of the donors in FIG. 30 and FIG. 31.
Figure 30:
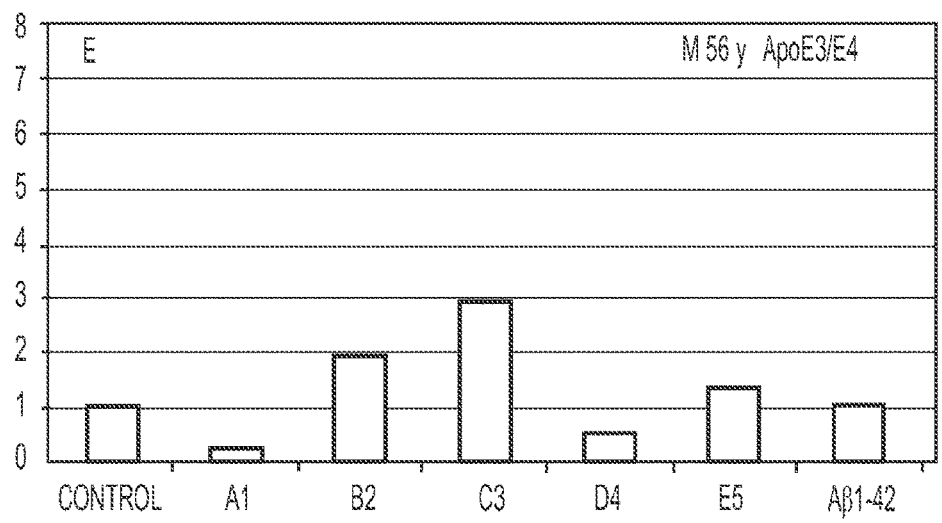
FIG. 30 shows the same type of data shown by 26, that the blood donor was the 56 year old sister of the donors in FIG. 29 and FIG. 31, and like her sisters, has an ApoE3/E4 genotype.
Figure 31:
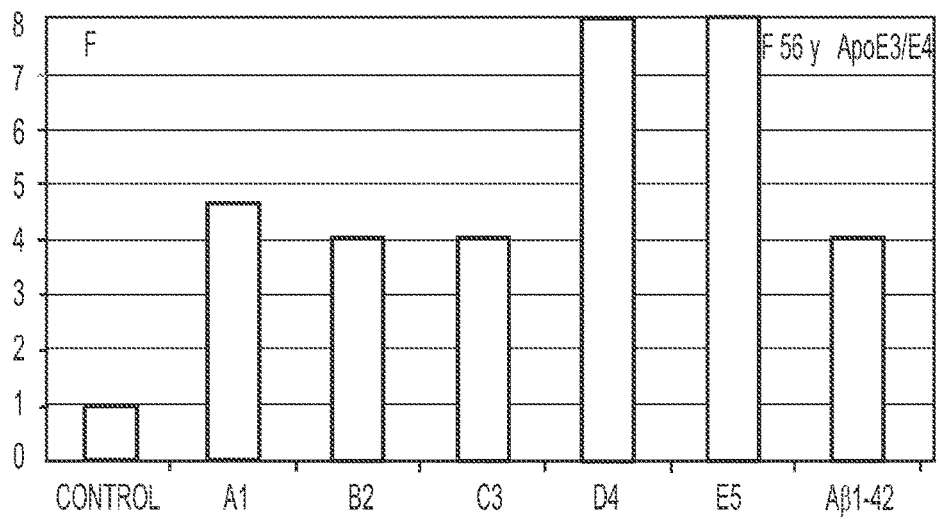
FIG. 31 shows the same type of data shown by 26, that the blood donor was the 61 year old sister of the donors in FIG. 30 and FIG. 29, and like her sisters, has an ApoE3/E4 genotype.

Insoluble deposits of this peptide accumulate in neuritic brain plaques, and are a definitive hallmark of Alzheimer's disease pathology (Braak and Braak, 1997). Aβ-specific CD4$^+$ T cells attenuate Alzheimer's disease pathology and behaviors in mouse models for the disease (Ethell et al., 2006; Cao et al., 2009). Vaccination with Aβ1-42 was tried as an Alzheimer's therapy and though promising, the trial was halted due to inflammation of brain meninges in a subset (6%) of subjects (Orgogozo et al., 2003). As yet it remains unclear if Aβ-specific T cell responses emerge during AD etiology and if they may provide early beneficial effects that become overwhelmed as the disease progresses (Ethell et al., 2002; Ethell and Buhler, 2003; Cao et al., 2009). T cells were prepared as above in Example 1, and co-cultured with mature DCs that had been pre-loaded with Aβ1-42. Five of six AD subjects showed greater than a three-fold increase in CD4$^+$ T cell proliferation in response to Aβ-presenting DCs than control DCs, while none of the control subjects showed a response greater than 2× controls (FIG. 7F). The absence of a proliferative response to Aβ-loaded DC in one AD subject (AD4) may have been due to an incorrect diagnosis as a definitive diagnosis of AD can only made with post-mortem brain pathology (Alzheimer, 1907; Fischer, 1907).

Example 3

Method of Using hESC-Derived DCs Transduced with Lentiviral Constructs Engineered to Express HLA-DRA-Aβ Fusion Proteins to Assess CD4$^+$ T Cell Responses Compositions and methods of the invention have been used to assess repertoires of CD4$^+$ T cell responses to the Alzheimer's peptide, Amyloid-beta (Aβ), in thirty-six human subjects. The CD4$^+$ T cells were obtained from whole blood that was obtained using standard phlebotomy methods. An initial Nylon wool-based purification method removed the majority of myeloid cells and B cells, thereby enriching the T cell population. The T cells were then stained with carboxyfluorescein diacetate succinimidyl ester (CFSE) and then mixed with a panel of HLA-DRA-Aβ fusion protein-expressing APCs and cocultured for 7-10 days. The panel of fusion proteins included full length Aβ; Aβ1-13; Aβ7-13; Aβ16-30; Aβ24-35; Aβ31-42; and Aβ7-23. After the incubation period the cell mixture was stained with CD4-specific fluorescent antibodies, and run through a flow cytometer. CD4-specific fluorescence was used to identify $CD4^+$ T cells, and CFSE intensity was used to determine how much proliferation those $CD4^+$ T cells have undergone since the T cells were initially stained with CFSE. The following examples exemplify the various steps of the invention.

The HLA-DRA/Amyloidfl β fusion constructs. Human HLA class II alpha chain (HLA-DRA, gene bank entry provided) was cloned from human blood peripheral blood monocytes (PBMC) from 1 mL of whole blood by isolating RNA using standard methods, and then using a standard reverse transcription method to create the HLA-DRA cDNA template. The HLA-DRA nucleotide sequence was then amplified by adding the HLA-DRA cDNA template in a standard polymerase chain reaction (PCR) (Primers were HLA-DRAF(forward): 5'-TTATTCTTGTCTGTTCTGC-CTC (SEQ ID NO: 3); HLA-DRAR(reverse) 5'-CT-TCTCTCTAAGAAACACCATCACCTC (SEQ ID NO: 4), which were designed by the inventor, Doug Ethell) containing proof-reading DNA polymerase enzyme, "Phusion" (New England Biolabs). The products of the PCR were resolved on an agarose gel, and a single band of the correct size (approximately 2 kb) was isolated from the gel, and then ligated into pCR®8/GW TOPO® TA vector (Invitrogen Corp., Life Technologies, Carlsbad, Calif.) according to the manufacturer's instructions. A pCR®8 TOPO® TA plasmid that contained a HLA-DRA clone with the correct sequence and without mutations was selected. Site-directed mutagenesis (SDM) was used to introduce the nucleotide sequence that encoded the poly-glycine/serine linker at the 5' end of the HLA-DRA sequence. Standard DNA sequencing of subsequent clones resulting from the SDM was used to identify a clone with the correct sequence. FIG. 9 shows a plasmid map of the resulting pCR®8/GW TOPO® -HLA-DRA+linker plasmid. SDM was used with this plasmid was used to generate each of the amyloid beta (Aβ)fusion constructs used in these studies. Specifically, Aβlinker+ HLA-DRA fusion constructs were made that contained the following Aβ fragments: Aβ1-13 (FIG.11); Aβ7-13 (FIG. 12); Aβ16-30 (FIG. 13); Aβ24-35 (FIG. 14); Aβ31-42 (FIGS. 15); and Aβ7-23 (FIG. 16).

Each of the above Aβ+linker+HLA-DRA fusion constructs were subcloned from their respective pCR®8/GW TOPO® vectors into a FUW lentivirus vector (described in Science. 2002 Feb. 1. 295(5556):868-72. Epub 2002 Jan. 10) at the EcoRI site of the multiple cloning site of the FUW vector using a standard molecular biology cloning approach. Each Aβ+linker+HLA-DRA fusion restriction fragment was gel purified prior to insertion into the FUW vector. The orientation of the Aβ+linker+HLA-DRA insert was confirmed by restriction digests. Specifically, the nucleases XbaI and PstI were used to confirm orientation of the inserts.

Protein expression of the Aβ+linker+HLA-DRA fusion proteins was driven by the ubiquitin promoter that was present on the FUW plasmid. Western blot analysis showed that that the FUW constructs expressed the Aβ+linker+ HLA-DRA fusion proteins when the constructs were introduced into 293 cells. See FIG. 15. The Western blot analysis of the cell lysates was performed by using an HLA-DRA-specific antibody (Abnova cat # MAB7134, clone L243) to probe the blot.

Human Embryonic Stem Cell (hESC)-Derived Dendritic Cells. A frozen vial of H9 line of hESC (WiCell/National Stem Cell Bank) was quickly thawed in a 37° C. water bath by gently shaking the cryovial continuously until only a small frozen pellet remains. The cryovial was then removed from the water bath and wiped with isopropyl alcohol. Using a 1 ml pipette tip, the contents of the cryovial were transferred to a 15 ml conical tube. Nine mL of pre-warmed Stem cell medium (mTeSR complete from Stem Cell Technologies, Vancouver, Canada) was added dropwise to the tube, and gently mixed as the medium was added. The cells were then centrifuged at 300×g for 5 minutes at room temperature (25° C.). The medium was aspirated, leaving the cell pellet intact. Using a 1 ml pipette tip, the cell pellet was gently resuspended while taking care to maintain the cells as aggregates. Ensuring that clumps are evenly distributed, 1 ml cell of cell aggregates were transferred to a matrigel (Becton-Dickinson, prepared per the manufacturer's instruction) coated T25 flask. The flask was then moved side to side quickly, followed by forward to back motions until the cell aggregates were evenly distributed within the medium. The cells were cultured in a humidified incubator at 37° C., with 5% $CO_2$. The hESC cultures were fed every other day with a 100% replacement of fresh mTeSR media per T25 flask (4 ml). At approximately 5-7 days after being thawed, the hESC cultures were checked for the presence of hESC colonies that were ready to passage (i.e., dense centered with smooth edges).

Passage of undifferentiated hESCs. Colonies of hESC's that were ready to passage, as described above, were examined using a microscope to identify regions undifferentiated colonies, which were removed by scraping the matrigel surface with a pipette tip. No more than 20% of the surface area of each flask was scraped at this step. The detached cells were transferred to a matrigel-coated T25 flasks that contained 4 mL of mTeSR media. Any relatively large colonies that existed after transfer of the undifferentiated cells to a new T25 flask were broken up by gently pipetting the colonies up and down through a 1 mL pipette tip. The undifferentiated cells were gently mixed by rocking the T25 flask, and then the flask was placed in the incubator. Undifferentiated hESC colonies, identifiable by the absence of rough colony edges, were maintained by feeding the cultures every other day with 4 ml of mTeSR medium. The undifferentiated hESC's were used in experiments 5 to 6 days after passage.

Culture of OP9 cells. OP9 bone-marrow stromal cells (ATCC cat No. CRL-2749) were used to stimulate hematopoietic stem cell (HSC) lineage differentiation of the hESC, although other bone-marrow stromal cells could be substituted in this procedure. OP9 cells were kept in OP9 medium: 1× alpha-MEM (Life Technologies) medium supplemented with 20% FBS (without heat-inactivation), L-glutamine. The OP9 cultures were maintained in T75 flasks that in a humidified incubator at 37° C. and 5% $CO_2$, as described in the ATCC protocol. Briefly, OP9 cultures were fed every 2 days, and passaged every day 4 days. To passage the OP9 cultures, the culture medium was aspirated from the flask, and the OP9 cell monolayer was washed with 8 mL of PBS. In order to detach the OP9 cells from the flask surface, TRYPLE express (Life Technologies) solution (4 mL) was added to the flask, and the flask was placed in a 37° C. incubator for 5 min. The TRYPLE treatment was stopped by adding 4 mL of 0.5% BSA in PBS. The treated cells and solution were transferred to a 15 ml tube and the tube was centrifuged at 300×g for 5 min. Following centrifugation, the supernatant was aspirated, and the cells were resuspended in 1 mL OP9 medium. The cell solution was resuspended into 30 mL OP9 medium and 10 mL of resuspended cells were added to each of 3 new T75 flasks. The OP9 cells grew to 85% confluence after about 4 days, when they were split again as described above.

Hematopoietic Differentiation of hESCs by Co-culture with OP9 Stromal Cells. To prepare for hESC differentiation T75 flasks of OP9 cells were overgrown (i.e., 4 to 5 days post-split). The culture medium was aspirated and 10 mL of hESC-HSC differentiation media (1× alpha-MEM supplemented with 10% FBS (not heat-inactivated) and 100 µM Monothioglycerol (MTG, Sigma cat# M6145) was added to the flask, and the culture incubated for 20 min. While the OP9 cells were incubating with the hESC-HSC differentiation medium, the mTeSR medium was removed from a T25 flask of hESC colonies (5 to 6 days post-split), and the hESC culture was rinsed with 5 mL PBS. The cells were covered with 3 mL of PBS supplemented with 5% FBS, and the hESC colonies were then detached from the surface of the T25 flask and broken up using a cell scraper (BD Falcon cat#353085) The detached hESC colonies were then transferred to a 15 mL conical tube by pipette. The flask was then rinsed with another 3 mL of PBS/5% FBS, which was added to the same 15 mL tube that contained the colonies from the scraping. The 15 mL tube containing disrupted hESC colonies was centrifuged at 300×g for 5 min. The supernatant was aspirated, and the pellet was gently resuspended in 1 mL of hESC-differentiated medium, by tapping the flask and gently triturating with a 1 mL pipette, and care was taken not to break up cell clumps. The volume of the cell suspension was between 1.5 mL and 2 mL, and typically contained about $10^6$ cells/ml. An additional 9 mL of hESC-HSC differentiation medium was gently added to the hESC cell suspension, and care was taken to keep the hESC cell clumps intact. Then 10 mL of hESC-containing hESC-HSC medium was evenly distributed to the OP9 flask that is had been incubating with 10 mL of hESC-HSC differentiation media, as described above. The flask was then place in a humidified incubator at 37° C. and 5% $CO_2$. After one day of incubation, all of the media was aspirated away. Twenty mL of fresh hESC-HSC differentiation medium was added to the flask and the flask was returned to the incubator. The combined hESC/OP9 cultures were fed 4 and 6 days from the initial plating by replacing 50% of the medium (10 ml) with fresh hESC-HSC differentiation medium at each feeding. Beginning at day 4, the co-cultures were examined under a microscope to observe differentiation of the hESC colonies. Good HSC differentiation was marked by misshapen colonies that contrasted with undifferentiated hESC colonies, and the cultures did not contain adipogenic (large vacuole containing) OP9 cells. HSC colonies were harvested 7 to 8 days after initial plating.

Expansion of Myeloid Progenitors in GM-CSF Bulk Cultures. Coating of Plastic Surfaces with pHEMA. Poly(2-hydroxyethylmethacrylate)/pHEMA (Sigma cat# P3932) coating solution was prepared by adding 4 g of pHEMA to 10 mL 95% ethanol containing 10 mM NaOH in a 50 mL tube and rotating it in a 37° C. incubator overnight. To coat T25 flasks, 2 mL of pHEMA coating solution was used and the flask rotated tilted until the entire bottom surface was covered. The flask was placed on its side and excess pHEMA coating solution was drained into a corner and removed with aspiration. The flask was immediately placed in a horizontal position with the cap off and allowed to dry in the tissue culture hood overnight (no UV). The next day the lid was place on the flask and stored at room temperature until use. A single-cell suspension of day 8 hESC/OP9 co-cultures was prepared by successive enzymatic treatments with a collagenase-trypsin solution as follows. First, the medium of the hESC/OP9 co-culture was aspirated and washed with 10 ml PBS. Then 5 ml of collagenase solution (Sterile-filtered collagenase type IV in DMEM/F12 (1 mg/ml), Life Technologies No. 17104-019) per T75 flask was added and the flask incubated at 37° C. for 20 min. The collagenase solution was removed from the flask and transferred into a 50 ml conical tube. Five ml of Trypsin-EDTA solution (0.05% Trypsin in 0.5 mM EDTA solution, Life Technologies #25300-054) was then added to the same hESC/OP9 co-culture flask, and the flask was incubated for 20 min at 37° C. Five ml of PBS-5% FBS was added to the flask containing the Trypsin-EDTA solution, and the detached cells were resuspended by pipetting with a 10 ml serological pipet. The cells were then transferred to the same 50 ml collection tube that contained the collected collagenase solution, and the cells were mixed by closing the tube and inverting it. The cells were centrifuged in the same tube at 400×g for 10 minutes. The supernatant was removed, and the cells were washed with PBS-5% FBS, and centrifuged again for 400×g for 10 minutes. This wash step was repeated twice more and after the last wash the supernatant was removed. The cells were resuspended in 10 ml of myeloid cell expansion medium (MCEM. MCEM contained α-MEM supplemented with 10% non-heated inactivated hyclone FBS (Hyclone), 1×MTG (100 µM), and 100 ng/ml GM-CSF (R&D Systems cat. 215-GM). The GM-CSF was added immediately before use. After resuspending the cells in MCEM, the cell suspension was filtered through a 70 µM nylon filter that was fitted onto a 50 ml tube. After the filtering step, the total cell number of cells was calculated using a hemacytometer and trypan blue. The cells were ultimately suspended at a concentration of 2 to $3 \times 10^6$ cells/ml. The suspended cells, which included hESC-derived common myeloid progenitor cells, were dispensed into pHEMA-coated T25 flasks (5 ml/T25 flask), and incubated at 37° C. and 5% $CO_2$. The cultures were fed new MCEM 4, 8, and 12 days after plating, by replacing 50% of each flask's medium with fresh MCEM. At each feeding, 2.5 mL of media was removed and centrifuged at 300×g for 10 min. The supernatant was completely removed and the cell pellet was resuspended in fresh MCEM, and returned to the flask. Cells were harvested at either 11 or 12 days after the co-culture was established.

Differentiation of Myeloid Progenitors to DC. The myeloid progenitors described in the step above, were collected directly from the T25 flask and then filtered through a 70 µm nylon sieve, transferred to a 15 ml of conical tube, and centrifuged at 400×g for 10 minutes. A pipette was used to remove the supernatant, and the cells were then resuspended in 5 ml of PBS. The cell suspension was underlayed with 5 ml of 25% Percoll (Sigma cat. No. P1644), and then centrifuged for 400×g for 15 minutes. The cells were washed twice with PBS-5% FBS and centrifugation of 450×g for 10 min., with care taken to keep the cell pellet intact. After the final wash, the cells were resuspended in 8 mL of Dendritic Cell Differentiation medium: (DCDM). DCDM consisted of StemSpan serum-free expansion media (SFEM) (Stem Cell Tech cat. #09650), supplemented with a 1/500 dilution of EX-CYTE growth enhancement supplement (Millipore. cat. #81-129-N), 100 ng/mL recombinant human GM-CSF (Sigma), and 100 ng/mL of recombinant human IL-4 (R&D Biosystems). Half of the cell-containing solution was added to a each of two T25 flasks. The final concentration of the cell suspension in each flask was between $2 \times 10^5$ and $1 \times 10^6$ cells/mL of DCDM. The cells were fed 4 and 8 days after plating by replacing 50% of the DCDM. Two mL of medium was removed from each flask and centrifuged at 400×g for 10 min. The supernatant was removed and the cells were resuspended in 2 mL of fresh DCDM, and the solution was added back to the flask, which was returned to the incubator.

Maturation of Dendritic cells (DC) (General maturation process). Using a standard Trypsin solution cell-detachment method, 10-12 day culture of dendritic cells were collected in to a 15 ml conical tube, and centrifuged at 400×g for 10 minutes. The supernatant was removed by pipetting, and the pellet was resuspended and gently mixed with 4 ml of freshly prepared DC maturation medium (SFEM supplemented with EX-CYTE growth enhancement supplement (Millipore. cat. #81-129-N). The resuspended DCs were transferred to a pHEMA coated T25 flask, and incubated at 37° C. and 5% $CO_2$. The DCs began to form dendritic processes began by days 2-3 after plating the cells Infection and Maturation of Dendritic Cells. Preparation of Lentiviruses. Lentiviruses were produced by the transfection of plasmids in HEK293 cells. Human embryonic kidney 293 cells/HEK293 (hereafter referred to as simply 293) cells were maintained in 293 medium (Dulbecco Minimal Essential Medium (DMEM) supplemented with 10% FBS and L-glutamine) in a humidified incubator at 37° C. with 5% $CO_2$. Cells were split at 80% confluence by removing the medium with aspiration, rinsing cells with PBS (5 mL for a 10 cm diameter dish), and the placing Trypsin-EDTA on the cells for 3 to 4 min (5 mL for a 10 cm diameter dish). After Trypsin-EDTA treatment, 5 mL of 293 medium was added to the dish and the cells were gently dislodged by pipetting the solution up and down. Resuspended 293 cells and the medium were transferred to a 15 mL tube, and centrifuged at 500×g for 5 min. The supernatant was removed with aspiration, the cell pellet resuspended in 1 mL of PBS, and cells counted using a hemacytometer. Cells were dilutes in 293 medium and $5\times10^5$ cells in 2 mL were plated in each well of a 6-well plate. The plate was place in the incubator overnight, and the next day the cells were transfected with plasmids. Lipofectamine2000 (Life Technologies) was used to transfect plasmids into the 293 cells. All fusion protein-expressing lentiviruses were made separately in different wells using, as follows. Fifty microliters of OptiMEM (Life Technologies) was placed into two 1.5 mL microcentrifuge tubes and allowed to warm to room temperature over 10 min in the tissue culture hood. In one tube the following plasmids were added: 2 µg of Lentivirus-expressing Aβ-HLA-DRA fusion protein construct, 2 µg of VSVG, 2 µg of Δ8.9. All plasmids were prepared from ampicillin-resistant $E.$ $coli$ cultures using Endo-Free Maxi Kits (Qiagen). In the second tube 10 mL of lipofectamine2000 was added. The contents of both tubes were added together, mixed and left in the tissue culture hood for 20 min. After this time, the solution was added to a well of 293 cells dropwise, as per the manufacturer's lipofectamine protocol (Life Technologies). After lipofectamine-containing solutions were added to each well the plate was returned to the incubator. The next day, the media was removed from the 293 cells and replace with 1 mL of DCDM. Cells were incubated again for two days, when virus-containing medium was removed and ready to infect immature DC. After 10 days in DCDM, dendritic cells were collected and pelleted in 15 mL conical tubes at 400×g. The supernatant was removed with a pipet, and the DC-containing pellet was resuspended with 1 mL of DCDM and the cells counted with a hemacytometer. Generally, $5\times10^5$ cells were used for each Aβ-fusion lentivirus infection and experimental control (i.e., IL-2, Abeta peptide, untreated control). A total of 10 wells of a pHEMA-coated 24 well plate were prepared for infections and controls. The pHEMA coating was done as above except 500 µL of pHEMA coating solution was used for each well. Lentivirus-containing media (600 µL) from 293 transfected with fusion protein vectors were added to 7 of the wells. Conditioned media from 293 cells that had been transfected with either the empty FUGW lentivirus vector, or FUGW vectors containing the Aβ fusion protein DNA sequences (Aβ 1-13, Aβ 7-13, Aβ 16-30, Aβ 24-35, and Aβ 31-42), were added to six of the wells, respectively. The three remaining wells were treated as follows: 1) with DC differentiation medium containing 10 µg/ml of Aβ1-42 polypeptide (Biomer Technology, Pleasanton Calif.); 2) with DC differentiation medium containing IL-2; and 3) with only DC differentiation medium. Then $5\times10^5$ differentiated DCs were added to each well. After adding the differentiated DCs, the plate was moved side to side and then incubated for 2 days at 37° C. and 5% $CO_2$. On the $2^{nd}$ day after starting the infections, the media were removed from each well, and one mL replaced with DC maturation medium (DCMM). DCMM consisted of DCDM supplemented with 100 µg/mL recombinant human TNF-α, and 250 ng/mL lipopolysaccharide (LPS). The infected DCs were incubated with DCMM for 3 additional days.

Isolation of T cells. Whole blood was collected from the volunteers using standard phlebotomy techniques. Approximately 20 mL of whole blood was collected from each subject into purple top EDTA-coated phlebotomy tubes (Becton-Dickinson). The blood was diluted 1:1 with PBS (Gibco cat. #14040), and 24 mL of the diluted blood was layered onto 18 mL Ficoll-Paque Plus in a 50 mL conical tube (proportion 1:1.4, GE Healthcare Biosciences, Upsala, SE, cat #17-1440-02). The tube containing the diluted blood and Ficoll solution was centrifuged at 400×g for 30 min at room temperature. The supernatant (i.e., the yellow plasma component) was aspirated and discarded. The interface layer, between the plasma component and the Ficoll layer, was carefully removed and transferred into a fresh tube. This interface layer contained the peripheral blood lymphocytes (PBL) and monocytes. The PBL-containing tube was filled with 25 mL of 1×PBS, mixed and then centrifuged at 1500×g for 10 min. The supernatant was removed by aspiration and the pellet was resuspended with 10 mL of PBS. The at 1500× g for 10 min and the washing step repeated twice more. After the final rinse, cells were resuspended in 1 mL of PBS and counted using a hemocytometer. The cells were then re-suspended in RPMI to a cell concentration of $20\text{-}50\times10^6$ cells/mL.

T cells were purified from the adherent cells such as B cells and monocytes by passing the PBLs incubating them in a sterile Nylon wool column (Polysciences Inc. Cat. No. 21759). Briefly, the 10 mL Nylon wool column was wetted by adding 5 mL of RPMI medium to the top of the column, and allowing the medium to pass through the column by opening the stop cock at the bottom of the column. A second wash with 5 mL of RPMI medium was also done, and then 5 mL of RPMI medium was left in the column by adding the medium to the top, with the stop cock closed. The top of the column was then sealed with a syringe plunger and the RPMI medium-containing column was then incubated at 37° C. for 1 hour. After this incubation, the column was clamped in a vertical position and the stop cock was opened to allow the RPMI medium to run through column. The column was then rinsed with another 5 mL of RPMI with the stopcock open. Four mL of cell suspension ($2\text{-}5\times10^6$ cells/mL) was added to the top of the column (total 4 mL of PBL) and the solution was allowed to enter the column with the stopcock closed. One mL of RPMI was then layered on top of the column and allowed to enter the nylon wool. The stopcock was closed, the top of the column was sealed with a syringe plunger, and the column was incubated at 37° C. for 1 hour. After the 1 hour incubation, the column was mounted vertically in the tissue culture hood and the plunger was removed. The stopcock was opened and the effluent collected by flow through the column by gravity. This effluent consisted of a T cell enriched fraction. The column was washed once more with 10 mL of RPMI medium, and the effluent was collected by gravity flow. The two effluents were combined in a 50 mL conical tube and centrifuged at 1500×g for 10 min. The supernatant was aspirated ad the T cell enriched preparation was resuspended in 1 mL of PBS. Cells were counted using a hemacytometer. Only the relatively large cells in the cell suspension were counted as T cells of interest.

Carboxyfluorescein diacetate succinimidyl ester (CFSE) staining of T cells. Once the T cell suspension collected from the Nylon column was counted, the suspension was centrifuged at 1500×g for 10 min, and resuspended in 4 mL of PBS containing 0.1% BSA, pre-warmed to 37° C. Then 4 mL of PBS/BSA containing 8 µM CFSE (CellTrace™ CFSE Cell Proliferation Kit, Invitrogen) was added to 4 mL of cell suspension, and the mixture was incubated in a 37° C. water bath for 8 min. Immediately after the incubation, the cell solution was diluted with 10 mL of RPMI that contained 10% hyclone fetal bovine serum (FBS). The cell suspension was then centrifuged at 1500×g for 10 min at 25° C. CFSE-stained T cells were washed twice with 10 mL of PBS containing 0.1% BSA (Bovine serum albumin fraction V, Calbiochem. cat #2930), with 5 min centrifugations at 1500×g at 25° C. After the final wash, the T cells were resuspended in 1 mL of RPMI and counted. CFSE staining was confirmed by analyzing an aliquot of the CFSE-stained resuspended T cells by flow cytometry (Accuri/BD). Analysis was performed by flow cytometry (FL1 channel) to confirm uniform intensity of CFSE staining. The mature differentiation media was removed from the mature DCs that had been infected 3 days earlier.

Coculturing mature, HLA-DRA-Aβ-presenting dendritic cells with CFSE-labeled T cells from Subjects Diagnosed with AD. One million (1×10$^6$) CFSE-stained T cells were then added to each well of mature dendritic cells that had been infected with HLA-DRA-Aβ fusion protein-expressing lentiviruses, pre-loaded with Aβ1-42 peptide (10 µg/ml), or two untreated wells. Cells were mixed by moving the 24-well plate in a side to side motion, followed by forward to back motions so that the T cells were evenly distributed in the wells. The plate was returned to the incubator. On the following day, 1 µl of human IL-2 (GIBCO, Cat No. PHC0026) was added to each well. The final concentration of IL-2 was 200 ng/ml. The IL-2 was distributed by subjecting the plate to gentle side to side motions, and then the cells were incubated at 37° C. for 9 days. At day 10, the populations of CD4-positive T cells were determined by ACCURI™ flow cytometry, as described below.

Immunostaining with anti-CD4. The day 10 co-cultures of T cells and engineered DCs were collected by using a fresh 1 mL pipette tip for each well to transfer the medium in each well to a separate 15 mL conical tube. The surface of the plate wells were washed with 1 ml of PBS, and the washings were pooled with the previous wash from corresponding wells. Once the cells from all of the wells had been collected, the tubes were centrifuged at 450×g for 10 min. The supernatant was discarded, and the cells were washed once with 5 mL PBS and then centrifuged again at 450×g for 10 min. The supernatant was discarded, and the pellet was collected. The cells were immunostained (live) with fluorescently conjugated anti-CD4 antibody and assayed by flow cytometry. After the incubation, 50 µl of each cell suspension (i.e., 1×10$^6$ cells) were transferred to fresh flow cytometry tubes. One µl of fluor Alexa647-conjugated anti-CD4 antibody (Alexa Fluor® 647 mouse anti-human CD4 antibody, BD Biosciences, Cat. No. 557707) was added to each tube. The remaining 50 µl of NMS-blocked T cells were used for antibody isotype controls. One µl of isotype control antibody (Alexa Fluor® 647 mouse IgG1k isotype control, BD Biosciences, Cat. No. 557714) was added to the cells used for the isotype control of each experimental condition. Both the anti-CD4-labelled and the isotype control cells were incubated for 1 hour in the dark at 4° C. After the incubation, 1 mL of cold 0.5% BSA in PBS (Calbiochem Cat. No. 2930) was added to each tube, and the tubes were centrifuged at 200×g for 5 minutes. The supernatant was discarded, and the washing step was repeated twice. The last wash contained only PBS without 0.5% BSA. The cells in each tube were resuspended with 200 µl ice-cold 1×PBS.

Measurement of CD4$^+$ T cells proliferation by ACCURI™ flow cytometry. Cells were assayed using an Accuri flow cytometer. A forward scatter (FSC) and side scatter (SSC) dot plot was used to create a gate around the T cell containing population, which was determined in preliminary studies. Cell events within that gate were plotted on a histogram for FL2, which indicated Alexa 647 fluorescence (red). Cells labeled by the anti-CD4 antibody were significantly more fluorescent in the histogram and gating was used to isolate that population. An FL1 (green) fluorescence histogram showed CFSE labeling in CD4$^+$ cells. The most intense labeling was seen (far right) in cells that had not divided. Cells that underwent cell divisions had progressively less CFSE fluorescence. The IL-2 treatment condition CFSE plot was used to determine the extent of fluorescence for each step (i.e. division). Those markers were transferred to the CFSE plots of each experimental condition to determine CD4$^+$ T cells had divided more than 5 times during the experiment. Comparisons of T cell proliferation profiles in each condition were used to determine the relative abundance and responsiveness of Aβ-specific CD4$^+$ T cells in each blood sample.

REFERENCES

Agrawal, A., and Gupta S. (2011). Impact of aging on dendritic cell functions in humans. Ageing Res. Rev. 10, 336-345.

Albani S, et al. (2011), Induction of immune tolerance in the treatment of rheumatoid arthritis. Nat. Rev. Rheumatol. 7, 272-281.

Braak, H., and Braak, E. (1997). Diagnostic criteria for neuropathologic assessment of Alzheimer's disease. Neurobiol. Aging 18, S85-S88.

Cao, C., et al. (2009). Aβ-specific T cells are sufficient for beneficial effects in the APP+PS1 mouse model for Alzheimer's disease. Neurobiol. Dis. 34, 63-70.

Choi, K. D., et al. (2009). Generation of mature human myelomonocytic cells through expansion and differentiation of pluripotent stem cell-derived lin-CD34+CD43+CD45+ progenitors. J. Clin. Invest. 119, 2818-2829.

Chow, A., et al. (2002). Dendritic cell maturation triggers retrograde MHC class II transport from lysosomes to the plasma membrane Nature 418, 988-994.

Codarri, L., et al. (2012). Communication between pathogenic T cells and myeloid cells in neuroinflammatory disease. Trends Immunol. October 29. pii: S1471-4906(12)00174-3. doi: 10.1016/j.it.2012.09.007. [Epub ahead of print]

Daigneault, M., et al. (2010). The identification of markers of macrophage differentiation in PMA-stimulated THP-1 cells and monocyte-derived macrophages. PLoS One 5, e8668.

Delong, T., et al. (2012). Novel autoantigens for diabetogenic CD4 T cells in autoimmune diabetes. Immunol. Res. September 13. [Epub ahead of print].

Ethell, D. W., et al. (2002). Metalloproteinase shedding of Fas ligand regulates β-amyloid neurotoxicity. Curr. Biol. 12, 1595-1600.

Ethell, D. W., and Buhler, L. A. (2003). Fas ligand-mediated apoptosis in degenerative disorders of the brain. J. Clin. Immunol. 23, 363-370.

Ethell, D. W. et al. (2006). Aβ-specific T cells reverse cognitive decline and synaptic loss in Alzheimer's mice. Neurobiol. Dis. 23, 351-361.

Fox, C. B., et al. (2012). Adjuvanted pandemic influenza vaccine: variation of emulsion components affects stability, antigen structure, and vaccine efficacy. Influenza Other Respi Viruses. November 5. doi: 10.1111/irv.12031.

Frasca, D., and Blomberg, B. B. (2011). Aging impairs murine B cell differentiation and function in primary and secondary lymphoid tissues. Aging Dis. 2, 361-373.

Gojanovich, G. S., and Hess P. R. (2012). Making the most of major histocompatibility complex molecule multimers: applications in type 1 diabetes. Clin. Dev. Immunol., 380289. doi: 10.1155/2012/380289. Epub 2012 May 28.

Haas, W., et al. (1993). Gamma/delta T cells. Ann. Rev. Immunol. 11, 637-685.

Haskins, K., and Cooke, A. (2011). CD4 T cells and their antigens in the pathogenesis of autoimmune diabetes. Curr. Opin. Immunol. 23, 739-745.

Hayday, A. C. (1995). γδ T cell specificity and function: how much like who? In T Cell Receptors, J. I. Bell, M. J. Owen, and E. Simpson, eds. (Oxford, U. K: Oxford University Press) 1995, pp. 70.

Hosken, N. A., et al. (1995). The effect of antigen dose on CD41 T helper cell phenotype development in a T cell receptor-αβ-transgenic model. J. Exp. Med. 182, 1579-1584.

Huang, J., et al. (2012). T cell antigen recognition at the cell membrane Mol. Immunol. 52, 155-164.

Klein, L., et al. (2010). Autophagy-mediated antigen processing in CD4(+) T cell tolerance and immunity. FEBS Lett. 584, 1405-1410.

Le Nouën, C., et al. (2010). Effects of human respiratory syncytial virus, metapneumovirus, parainfluenza virus 3 and influenza virus on CD4+ T cell activation by dendritic cells. PLoS One 5, e15017

McFarland, H. F., and Martin, R. (2007). Multiple sclerosis: a complicated picture of autoimmunity. Nat. Immunol. 8, 913-919.

Nakken, B., et al. (2011). B-cells and their targeting in rheumatoid arthritis-current concepts and future perspectives. Autoimmun. Rev. 11, 28-34.

Orgogozo, J. M., et al. (2003). Subacute meningoencephalitis in a subset of patients with AD after Abeta42 immunization. Neurology 61, 46-54.

Pao, W., et al. (1996). γδ T cell help of B cells is induced by repeated parasitic infection in the absence of other T cells. Curr. Biol. 6, 1317-1325.

Pereira, L. F., et al. (2011). Impaired in vivo CD4+ T cell expansion and differentiation in aged mice is not solely due to T cell defects: decreased stimulation by aged dendritic cells. Mech. Ageing Dev. 132, 187-194.

Philpott, K. L., et al. (1992). Lymphoid development in mice congenitally lacking T cell receptor αβ-expressing cells. Science 256, 1448-1452.

Sallusto, F., et al. (2012). T-cell trafficking in the central nervous system. Immunol. Rev. 248, 216-227.

S. Sakaguchi. (2000). Regulatory T cells: key controllers of immunologic self-tolerance. Cell 101, 455-458.

Schmidt, T., et al. (2012). CD4+ T-cell immunity after pandemic influenza vaccination cross-reacts with seasonal antigens and functionally differs from active influenza infection. Eur. J. Immunol. 42, 1755-1766.

Small, E. J., et al. (2000). Immunotherapy of hormone-refractory prostate cancer with antigen-loaded dendritic cells. J. Clin. Oncol. 18, 3894-3903.

Tetsutani, K., and Ishii, K. J. (2012). Adjuvants in influenza vaccines. Vaccine 30, 7658-7661.

J. A. Villadangos, P. Schnorrer, N. S. Wilson. (2005). Control of MHC class II antigen presentation in dendritic cells: a balance between destructive forces. Immunol. Rev. 207, 191-205.

Vodyanik, M. A., et al. (2005). Human embryonic stem cell-derived CD34+ cells: efficient production in the coculture with OP9 stromal cells and analysis of lympho-hematopoietic potential. Blood 105, 617-626.

Vodynik, M. A., and Sluvkin, I. I. (2007). Directed differentiation of human embryonic stem cells to dendritic cells. Methods Mol. Biol., 407, 275-293.

Wen, L., Barber, D. F., Pao, W., Wong, F. S., Owen, M. J., and Hayday, A. (1998). Primary gamma delta cell clones can be defined phenotypically and functionally as Th1/Th2 cells and illustrate the association of CD4 with Th2 differentiation. J. Immunol. 160, 1965-1974.

The claimed invention is:

1. A dendritic cell comprising a single peptide antigen presented on the surface of said dendritic cell, wherein said single peptide antigen is attached to a human leukocyte antigen-antigen D related alpha (HLA-DRA) alpha chain peptide through a peptide linker, wherein said HLA-DRA alpha chain peptide comprises a transmembrane domain and a cytoplasmic domain of HLA-DRA alpha chain peptide and wherein said single peptide antigen is not covalently linked with a major histocompatibility complex (MHC) beta chain peptide.

* * * * *

SEQUENCE LISTING

```
<160> NUMBER OF SEQ ID NOS: 25

<210> SEQ ID NO 1
<211> LENGTH: 13
<212> TYPE: PRT
<213> ORGANISM: Influenza A virus

<400> SEQUENCE: 1

His Asn Thr Asn Gly Val Thr Ala Ala Cys Ser His Glu
1               5                   10
```

-continued

```
<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Gly Gly Gly Ser Gly Gly Gly Gly Ser Gly Gly Gly Gly Ser
1               5                   10                  15

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttattcttgt ctgttctgcc tc                                                  22

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cttctctcta agaaacacca tcacctc                                             27

<210> SEQ ID NO 5
<211> LENGTH: 223
<212> TYPE: PRT
<213> ORGANISM: Homo sapiens

<400> SEQUENCE: 5

Ile Ile Gln Ala Glu Phe Tyr Leu Asn Pro Asp Gln Ser Gly Glu Phe
1               5                   10                  15

Met Phe Asp Phe Asp Gly Asp Glu Ile Phe His Val Asp Met Ala Lys
            20                  25                  30

Lys Glu Thr Val Trp Arg Leu Glu Glu Phe Gly Arg Phe Ala Ser Phe
        35                  40                  45

Glu Ala Gln Gly Ala Leu Ala Asn Ile Ala Val Asp Lys Ala Asn Leu
    50                  55                  60

Glu Ile Met Thr Lys Arg Ser Asn Tyr Thr Pro Ile Thr Asn Val Pro
65                  70                  75                  80

Pro Glu Val Thr Val Leu Thr Asn Ser Pro Val Glu Leu Arg Glu Pro
                85                  90                  95

Asn Val Leu Ile Cys Phe Ile Asp Lys Phe Thr Pro Pro Val Val Asn
            100                 105                 110

Val Thr Trp Leu Arg Asn Gly Lys Pro Val Thr Thr Gly Val Ser Glu
        115                 120                 125

Thr Val Phe Leu Pro Arg Glu Asp His Leu Phe Arg Lys Phe His Tyr
    130                 135                 140

Leu Pro Phe Leu Pro Ser Thr Glu Asp Val Tyr Asp Cys Arg Val Glu
145                 150                 155                 160

His Trp Gly Leu Asp Glu Pro Leu Leu Lys His Trp Glu Phe Asp Ala
                165                 170                 175
```

```
Pro Ser Pro Leu Pro Gly Thr Thr Glu Asn Val Val Cys Ala Leu Gly
        180                 185                 190

Leu Thr Val Gly Leu Val Gly Ile Ile Ile Gly Thr Ile Phe Ile Ile
        195                 200                 205

Lys Gly Leu Arg Leu Ser Asn Ala Ala Glu Arg Gly Pro Leu
    210                 215                 220

<210> SEQ ID NO 6
<211> LENGTH: 226
<212> TYPE: PRT
<213> ORGANISM: Homo sapiens

<400> SEQUENCE: 6

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
            20                  25                  30

Ile Gln Ala Glu Phe Tyr Leu Asn Pro Asp Gln Ser Gly Glu Phe Met
        35                  40                  45

Phe Asp Gly Asp Glu Ile Phe His Val Asp Met Ala Lys Lys Glu Thr
50                  55                  60

Val Trp Arg Leu Glu Glu Phe Gly Arg Phe Ala Ser Phe Glu Ala Gln
65                  70                  75                  80

Gly Ala Leu Ala Asn Ile Ala Val Asp Lys Ala Asn Leu Glu Ile Met
                85                  90                  95

Thr Lys Arg Ser Asn Tyr Thr Pro Ile Thr Asn Asp Lys Phe Thr Pro
            100                 105                 110

Pro Val Val Asn Val Thr Trp Leu Arg Asn Gly Lys Pro Val Thr Thr
        115                 120                 125

Gly Val Ser Glu Thr Val Phe Leu Pro Arg Glu Asp His Leu Phe Arg
    130                 135                 140

Lys Phe His Tyr Leu Pro Phe Leu Pro Ser Thr Glu Asp Val Tyr Asp
145                 150                 155                 160

Cys Arg Val Glu His Trp Gly Leu Asp Glu Pro Leu Leu Lys His Trp
                165                 170                 175

Glu Phe Asp Pro Ser Pro Leu Pro Thr Thr Glu Asn Val Val Cys
            180                 185                 190

Ala Leu Gly Leu Thr Val Gly Leu Val Gly Ile Ile Ile Gly Thr Ile
        195                 200                 205

Phe Ile Ile Lys Gly Val Arg Lys Ser Asn Ala Ala Glu Arg Arg Gly
    210                 215                 220

Pro Leu
225

<210> SEQ ID NO 7
<211> LENGTH: 265
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ser Ala Gln Glu Ser Trp Ala Ile Lys Glu Glu His Val Asp Ala
1               5                   10                  15

Glu Phe Arg His Asp Ser Gly Tyr Glu Val His Ile Gly Gly Gly Ser
            20                  25                  30
```

```
Gly Gly Gly Gly Ser Gly Gly Gly Ser Ile Ile Gln Ala Glu Phe
            35                  40                  45

Tyr Leu Asn Pro Asp Gln Ser Gly Glu Phe Met Phe Asp Phe Asp Gly
 50                  55                  60

Asp Glu Ile Phe His Val Asp Met Ala Lys Lys Glu Thr Val Trp Arg
 65                  70                  75                  80

Leu Glu Glu Phe Gly Arg Phe Ala Ser Phe Glu Ala Gln Gly Ala Leu
                 85                  90                  95

Ala Asn Ile Ala Val Asp Lys Ala Asn Leu Glu Ile Met Thr Lys Arg
            100                 105                 110

Ser Asn Tyr Thr Pro Ile Thr Asn Val Pro Pro Glu Val Thr Val Leu
            115                 120                 125

Thr Asn Ser Pro Val Glu Leu Arg Glu Pro Asn Val Leu Ile Cys Phe
        130                 135                 140

Ile Asp Lys Phe Thr Pro Pro Val Val Asn Val Thr Trp Leu Arg Asn
145                 150                 155                 160

Gly Lys Pro Val Thr Thr Gly Val Ser Glu Thr Val Phe Leu Pro Arg
                165                 170                 175

Glu Asp His Leu Phe Arg Lys Phe His Tyr Leu Pro Phe Leu Pro Ser
            180                 185                 190

Thr Glu Asp Val Tyr Asp Cys Arg Val Glu His Trp Gly Leu Asp Glu
            195                 200                 205

Pro Leu Leu Lys His Trp Glu Phe Asp Ala Pro Ser Pro Leu Pro Gly
        210                 215                 220

Thr Thr Glu Asn Val Val Cys Ala Leu Gly Leu Thr Val Gly Leu Val
225                 230                 235                 240

Gly Ile Ile Ile Gly Thr Ile Phe Ile Ile Lys Gly Leu Arg Leu Ser
                245                 250                 255

Asn Ala Ala Glu Arg Arg Gly Pro Leu
            260                 265

<210> SEQ ID NO 8
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Ala Gln Glu Ser Trp Ala Ile Lys Glu Glu His Val Asp Ser
 1               5                  10                  15

Gly Tyr Glu Val His Ile Gly Gly Ser Gly Gly Gly Gly Ser Gly
            20                  25                  30

Gly Gly Gly Ser Ile Ile Gln Ala Glu Phe Tyr Leu Asn Pro Asp Gln
            35                  40                  45

Ser Gly Glu Phe Met Phe Asp Phe Asp Gly Asp Glu Ile Phe His Val
        50                  55                  60

Asp Met Ala Lys Lys Glu Thr Val Trp Arg Leu Glu Glu Phe Gly Arg
 65                  70                  75                  80

Phe Ala Ser Phe Glu Ala Gln Gly Ala Leu Ala Asn Ile Ala Val Asp
                 85                  90                  95

Lys Ala Asn Leu Glu Ile Met Thr Lys Arg Ser Asn Tyr Thr Pro Ile
            100                 105                 110

Thr Asn Val Pro Pro Glu Val Thr Val Leu Thr Asn Ser Pro Val Glu
```

```
                115                 120                 125
Leu Arg Glu Pro Asn Val Leu Ile Cys Phe Ile Asp Lys Phe Thr Pro
        130                 135                 140
Pro Val Val Asn Val Thr Trp Leu Arg Asn Gly Lys Pro Val Thr Thr
145                 150                 155                 160
Gly Val Ser Glu Thr Val Phe Leu Pro Arg Glu Asp His Leu Phe Arg
                165                 170                 175
Lys Phe His Tyr Leu Pro Phe Leu Pro Ser Thr Glu Asp Val Tyr Asp
                180                 185                 190
Cys Arg Val Glu His Trp Gly Leu Asp Glu Pro Leu Leu Lys His Trp
                195                 200                 205
Glu Phe Asp Ala Pro Ser Pro Leu Pro Gly Thr Thr Glu Asn Val Val
        210                 215                 220
Cys Ala Leu Gly Leu Thr Val Gly Leu Val Gly Ile Ile Ile Gly Thr
225                 230                 235                 240
Ile Phe Ile Ile Lys Gly Leu Arg Leu Ser Asn Ala Ala Glu Arg Arg
                245                 250                 255
Gly Pro Leu

<210> SEQ ID NO 9
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Ala Gln Glu Ser Trp Ala Ile Lys Glu Glu His Val Lys Leu
1               5                   10                  15
Val Phe Phe Ala Glu Asp Val Gly Ser Asn Lys Gly Ala Ile Gly Gly
                20                  25                  30
Gly Ser Gly Gly Gly Gly Ser Gly Gly Gly Gly Ser Ile Ile Gln Ala
        35                  40                  45
Glu Phe Tyr Leu Asn Pro Asp Gln Ser Gly Glu Phe Met Phe Asp Phe
    50                  55                  60
Asp Gly Asp Glu Ile Phe His Val Asp Met Ala Lys Lys Glu Thr Val
65                  70                  75                  80
Trp Arg Leu Glu Glu Phe Gly Arg Phe Ala Ser Phe Glu Ala Gln Gly
                85                  90                  95
Ala Leu Ala Asn Ile Ala Val Asp Lys Ala Asn Leu Glu Ile Met Thr
            100                 105                 110
Lys Arg Ser Asn Tyr Thr Pro Ile Thr Asn Val Pro Pro Glu Val Thr
        115                 120                 125
Val Leu Thr Asn Ser Pro Val Glu Leu Arg Glu Pro Asn Val Leu Ile
    130                 135                 140
Cys Phe Ile Asp Lys Phe Thr Pro Pro Val Val Asn Val Thr Trp Leu
145                 150                 155                 160
Arg Asn Gly Lys Pro Val Thr Thr Gly Val Ser Glu Thr Val Phe Leu
                165                 170                 175
Pro Arg Glu Asp His Leu Phe Arg Lys Phe His Tyr Leu Pro Phe Leu
            180                 185                 190
Pro Ser Thr Glu Asp Val Tyr Asp Cys Arg Val Glu His Trp Gly Leu
        195                 200                 205
Asp Glu Pro Leu Leu Lys His Trp Glu Phe Asp Ala Pro Ser Pro Leu
```

```
                    210                 215                 220
Pro Gly Thr Thr Glu Asn Val Val Cys Ala Leu Gly Leu Thr Val Gly
225                 230                 235                 240

Leu Val Gly Ile Ile Ile Gly Thr Ile Phe Ile Ile Lys Gly Leu Arg
                245                 250                 255

Leu Ser Asn Ala Ala Glu Arg Arg Gly Pro Leu
            260                 265

<210> SEQ ID NO 10
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Ala Gln Glu Ser Trp Ala Ile Lys Glu Glu His Val Val Gly
1               5                   10                  15

Ser Asn Lys Gly Ala Ile Ile Gly Leu Met Ile Gly Gly Ser Gly
            20                  25                  30

Gly Gly Gly Ser Gly Gly Gly Ser Ile Ile Gln Ala Glu Phe Tyr
        35                  40                  45

Leu Asn Pro Asp Gln Ser Gly Glu Phe Met Phe Asp Phe Asp Gly Asp
 50                  55                  60

Glu Ile Phe His Val Asp Met Ala Lys Lys Glu Thr Val Trp Arg Leu
65                  70                  75                  80

Glu Glu Phe Gly Arg Phe Ala Ser Phe Glu Ala Gln Gly Ala Leu Ala
                85                  90                  95

Asn Ile Ala Val Asp Lys Ala Asn Leu Glu Ile Met Thr Lys Arg Ser
            100                 105                 110

Asn Tyr Thr Pro Ile Thr Asn Val Pro Pro Glu Val Thr Val Leu Thr
        115                 120                 125

Asn Ser Pro Val Glu Leu Arg Glu Pro Asn Val Leu Ile Cys Phe Ile
130                 135                 140

Asp Lys Phe Thr Pro Pro Val Val Asn Val Thr Trp Leu Arg Asn Gly
145                 150                 155                 160

Lys Pro Val Thr Thr Gly Val Ser Glu Thr Val Phe Leu Pro Arg Glu
                165                 170                 175

Asp His Leu Phe Arg Lys Phe His Tyr Leu Pro Phe Leu Pro Ser Thr
            180                 185                 190

Glu Asp Val Tyr Asp Cys Arg Val Glu His Trp Gly Leu Asp Glu Pro
        195                 200                 205

Leu Leu Lys His Trp Glu Phe Asp Ala Pro Ser Pro Leu Pro Gly Thr
210                 215                 220

Thr Glu Asn Val Val Cys Ala Leu Gly Leu Thr Val Gly Leu Val Gly
225                 230                 235                 240

Ile Ile Ile Gly Thr Ile Phe Ile Ile Lys Gly Leu Arg Leu Ser Asn
                245                 250                 255

Ala Ala Glu Arg Arg Gly Pro Leu
            260

<210> SEQ ID NO 11
<211> LENGTH: 264
<212> TYPE: PRT
<213> ORGANISM: Artificial Sequence
<220> FEATURE:
```

-continued

<223> OTHER INFORMATION: Description of Artificial Sequence: Synthetic
      polypeptide

<400> SEQUENCE: 11

```
Met Ser Ala Gln Glu Ser Trp Ala Ile Lys Glu His Val Ile Ile
1               5                   10                  15

Gly Leu Met Val Gly Val Val Ala Ile Gly Gly Ser Gly
                20                  25                  30

Gly Gly Gly Ser Gly Gly Gly Ser Ile Ile Gln Ala Glu Phe Tyr
                35                  40                  45

Leu Asn Pro Asp Gln Ser Gly Glu Phe Met Phe Asp Phe Asp Gly Asp
                50                  55                  60

Glu Ile Phe His Val Asp Met Ala Lys Lys Glu Thr Val Trp Arg Leu
65                  70                  75                  80

Glu Glu Phe Gly Arg Phe Ala Ser Phe Glu Ala Gln Gly Ala Leu Ala
                85                  90                  95

Asn Ile Ala Val Asp Lys Ala Asn Leu Glu Ile Met Thr Lys Arg Ser
                100                 105                 110

Asn Tyr Thr Pro Ile Thr Asn Val Pro Pro Glu Val Thr Val Leu Thr
                115                 120                 125

Asn Ser Pro Val Glu Leu Arg Glu Pro Asn Val Leu Ile Cys Phe Ile
                130                 135                 140

Asp Lys Phe Thr Pro Pro Val Val Asn Val Thr Trp Leu Arg Asn Gly
145                 150                 155                 160

Lys Pro Val Thr Thr Gly Val Ser Glu Thr Val Phe Leu Pro Arg Glu
                165                 170                 175

Asp His Leu Phe Arg Lys Phe His Tyr Leu Pro Phe Leu Pro Ser Thr
                180                 185                 190

Glu Asp Val Tyr Asp Cys Arg Val Glu His Trp Gly Leu Asp Glu Pro
                195                 200                 205

Leu Leu Lys His Trp Glu Phe Asp Ala Pro Ser Pro Leu Pro Gly Thr
                210                 215                 220

Thr Glu Asn Val Val Cys Ala Leu Gly Leu Thr Val Gly Leu Val Gly
225                 230                 235                 240

Ile Ile Ile Gly Thr Ile Phe Ile Ile Lys Gly Leu Arg Leu Ser Asn
                245                 250                 255

Ala Ala Glu Arg Arg Gly Pro Leu
                260
```

<210> SEQ ID NO 12
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ser Ala Gln Glu Ser Trp Ala Ile Lys Glu His Val Asp Ser
1               5                   10                  15

Gly Tyr Glu Val His His Gln Lys Leu Val Phe Phe Ala Glu Asp Ile
                20                  25                  30

Gly Gly Gly Ser Gly Gly Gly Gly Ser Gly Gly Gly Ser Ile Ile
                35                  40                  45

Gln Ala Glu Phe Tyr Leu Asn Pro Asp Gln Ser Gly Glu Phe Met Phe
                50                  55                  60
```

```
Asp Phe Asp Gly Asp Glu Ile Phe His Val Asp Met Ala Lys Lys Glu
 65                  70                  75                  80

Thr Val Trp Arg Leu Glu Glu Phe Gly Arg Phe Ala Ser Phe Glu Ala
             85                  90                  95

Gln Gly Ala Leu Ala Asn Ile Ala Val Asp Lys Ala Asn Leu Glu Ile
        100                 105                 110

Met Thr Lys Arg Ser Asn Tyr Thr Pro Ile Thr Asn Val Pro Pro Glu
        115                 120                 125

Val Thr Val Leu Thr Asn Ser Pro Val Glu Leu Arg Glu Pro Asn Val
    130                 135                 140

Leu Ile Cys Phe Ile Asp Lys Phe Thr Pro Pro Val Val Asn Val Thr
145                 150                 155                 160

Trp Leu Arg Asn Gly Lys Pro Val Thr Thr Gly Val Ser Glu Thr Val
                165                 170                 175

Phe Leu Pro Arg Glu Asp His Leu Phe Arg Lys Phe His Tyr Leu Pro
            180                 185                 190

Phe Leu Pro Ser Thr Glu Asp Val Tyr Asp Cys Arg Val Glu His Trp
        195                 200                 205

Gly Leu Asp Glu Pro Leu Leu Lys His Trp Glu Phe Asp Ala Pro Ser
    210                 215                 220

Pro Leu Pro Gly Thr Thr Glu Asn Val Val Cys Ala Leu Gly Leu Thr
225                 230                 235                 240

Val Gly Leu Val Gly Ile Ile Ile Gly Thr Ile Phe Ile Ile Lys Gly
                245                 250                 255

Leu Arg Leu Ser Asn Ala Ala Glu Arg Arg Gly Pro Leu
            260                 265

<210> SEQ ID NO 13
<211> LENGTH: 1010
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1008)
<220> FEATURE:
<221> NAME/KEY: modified_base
<222> LOCATION: (970)..(970)
<223> OTHER INFORMATION: a, c, t, g, unknown or other
<220> FEATURE:
<221> NAME/KEY: modified_base
<222> LOCATION: (988)..(988)
<223> OTHER INFORMATION: a, c, t, g, unknown or other

<400> SEQUENCE: 13 tat gat ttt att ttg act gat agt gac ctg ttt cgt tgc aac aaa ttg      48
Tyr Asp Phe Ile Leu Thr Asp Ser Asp Leu Phe Arg Cys Asn Lys Leu
 1               5                  10                  15 gat gag caa tgc ttt ttt ata atg cca act ttg tac aaa aaa gca ggc      96
Asp Glu Gln Cys Phe Phe Ile Met Pro Thr Leu Tyr Lys Lys Ala Gly
            20                  25                  30 tcc gaa ttc gcc ctt tta ttc ttg tct gtt ctg cct cac tcc cga gct     144
Ser Glu Phe Ala Leu Leu Phe Leu Ser Val Leu Pro His Ser Arg Ala
        35                  40                  45 cta ctg act ccc aac aga gcg ccc aag aag aaa atg gcc ata agt gga     192
Leu Leu Thr Pro Asn Arg Ala Pro Lys Lys Lys Met Ala Ile Ser Gly
    50                  55                  60 gtc cct gtg cta gga ttt ttc atc ata gct gtg ctg atg agc gct cag     240
Val Pro Val Leu Gly Phe Phe Ile Ile Ala Val Leu Met Ser Ala Gln
 65                 70                  75                  80
```

```
                 65                  70                  75                  80
gaa tca tgg gct atc aaa gaa gaa cat gtg gat gca gag ttc cga cac        288
Glu Ser Trp Ala Ile Lys Glu Glu His Val Asp Ala Glu Phe Arg His
                 85                  90                  95 gat tcc gga tac gag gtg cac ata gga gga gga agt ggc ggc ggc ggc        336
Asp Ser Gly Tyr Glu Val His Ile Gly Gly Gly Ser Gly Gly Gly Gly
            100                 105                 110 agc ggt ggt ggt ggt agt atc atc cag gcc gag ttc tat ctg aat cct        384
Ser Gly Gly Gly Gly Ser Ile Ile Gln Ala Glu Phe Tyr Leu Asn Pro
        115                 120                 125 gac caa tca ggc gag ttt atg ttt gac ttt gat ggt gat gag att ttc        432
Asp Gln Ser Gly Glu Phe Met Phe Asp Phe Asp Gly Asp Glu Ile Phe
    130                 135                 140 cat gtg gat atg gca aag aag gag acg gtc tgg cgg ctt gaa gaa ttt        480
His Val Asp Met Ala Lys Lys Glu Thr Val Trp Arg Leu Glu Glu Phe
145                 150                 155                 160 gga cga ttt gcc agc ttt gag gct caa ggt gca ttg gcc aac ata gct        528
Gly Arg Phe Ala Ser Phe Glu Ala Gln Gly Ala Leu Ala Asn Ile Ala
                165                 170                 175 gtg gac aaa gcc aac ctg gaa atc atg aca aag cgc tcc aac tat act        576
Val Asp Lys Ala Asn Leu Glu Ile Met Thr Lys Arg Ser Asn Tyr Thr
            180                 185                 190 ccg atc acc aat gta cct cca gag gta act gtg ctc acg aac agc cct        624
Pro Ile Thr Asn Val Pro Pro Glu Val Thr Val Leu Thr Asn Ser Pro
        195                 200                 205 gtg gaa ctg aga gag ccc aac gtc ctc atc tgt ttc ata gac aag ttc        672
Val Glu Leu Arg Glu Pro Asn Val Leu Ile Cys Phe Ile Asp Lys Phe
    210                 215                 220 acc cca cca gtg gtc aat gtc acg tgg ctt cga aat gga aaa cct gtc        720
Thr Pro Pro Val Val Asn Val Thr Trp Leu Arg Asn Gly Lys Pro Val
225                 230                 235                 240 acc aca gga gtg tca gag aca gtc ttc ctg ccc agg gaa gac cac ctt        768
Thr Thr Gly Val Ser Glu Thr Val Phe Leu Pro Arg Glu Asp His Leu
                245                 250                 255 ttc cgc aag ttc cac tat ctc ccc ttc ctg ccc tca act gag gac gtt        816
Phe Arg Lys Phe His Tyr Leu Pro Phe Leu Pro Ser Thr Glu Asp Val
            260                 265                 270 tac gac tgc agg gtg gag cac tgg ggc ttg gat gag cct ctt ctc aag        864
Tyr Asp Cys Arg Val Glu His Trp Gly Leu Asp Glu Pro Leu Leu Lys
        275                 280                 285 cac tgg gag ttt gat gct cca agc ccc tct ccc aga gac tac aga gaa        912
His Trp Glu Phe Asp Ala Pro Ser Pro Ser Pro Arg Asp Tyr Arg Glu
    290                 295                 300 acg tgg gtg tgt gcc ctg ggc ctg act gtg ggg tct ggt ggg gca tca        960
Thr Trp Val Cys Ala Leu Gly Leu Thr Val Gly Ser Gly Gly Ala Ser
305                 310                 315                 320 tta ttg gga ncc att ctt cat cat caa ngg att gcg caa aag caa tgc       1008
Leu Leu Gly Xaa Ile Leu His His Gln Xaa Ile Ala Gln Lys Gln Cys
                325                 330                 335 ac                                                                    1010
```

<210> SEQ ID NO 14
<211> LENGTH: 336
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (324)..(324)

```
<223> OTHER INFORMATION: Thr, Ala, Pro or Ser
<220> FEATURE:
<221> NAME/KEY: MOD_RES
<222> LOCATION: (330)..(330)
<223> OTHER INFORMATION: Arg, Gly or Trp

<400> SEQUENCE: 14

Tyr Asp Phe Ile Leu Thr Asp Ser Asp Leu Phe Arg Cys Asn Lys Leu
1               5                   10                  15

Asp Glu Gln Cys Phe Phe Ile Met Pro Thr Leu Tyr Lys Lys Ala Gly
            20                  25                  30

Ser Glu Phe Ala Leu Leu Phe Leu Ser Val Leu Pro His Ser Arg Ala
        35                  40                  45

Leu Leu Thr Pro Asn Arg Ala Pro Lys Lys Met Ala Ile Ser Gly
    50                  55                  60

Val Pro Val Leu Gly Phe Phe Ile Ile Ala Val Leu Met Ser Ala Gln
65                  70                  75                  80

Glu Ser Trp Ala Ile Lys Glu Glu His Val Asp Ala Glu Phe Arg His
                85                  90                  95

Asp Ser Gly Tyr Glu Val His Ile Gly Gly Ser Gly Gly Gly Gly
            100                 105                 110

Ser Gly Gly Gly Gly Ser Ile Ile Gln Ala Glu Phe Tyr Leu Asn Pro
        115                 120                 125

Asp Gln Ser Gly Glu Phe Met Phe Asp Phe Asp Gly Asp Glu Ile Phe
130                 135                 140

His Val Asp Met Ala Lys Lys Glu Thr Val Trp Arg Leu Glu Glu Phe
145                 150                 155                 160

Gly Arg Phe Ala Ser Phe Glu Ala Gln Gly Ala Leu Ala Asn Ile Ala
                165                 170                 175

Val Asp Lys Ala Asn Leu Glu Ile Met Thr Lys Arg Ser Asn Tyr Thr
            180                 185                 190

Pro Ile Thr Asn Val Pro Pro Glu Val Thr Val Leu Thr Asn Ser Pro
        195                 200                 205

Val Glu Leu Arg Glu Pro Asn Val Leu Ile Cys Phe Ile Asp Lys Phe
    210                 215                 220

Thr Pro Pro Val Val Asn Val Thr Trp Leu Arg Asn Gly Lys Pro Val
225                 230                 235                 240

Thr Thr Gly Val Ser Glu Thr Val Phe Leu Pro Arg Glu Asp His Leu
                245                 250                 255

Phe Arg Lys Phe His Tyr Leu Pro Phe Leu Pro Ser Thr Glu Asp Val
            260                 265                 270

Tyr Asp Cys Arg Val Glu His Trp Gly Leu Asp Glu Pro Leu Leu Lys
        275                 280                 285

His Trp Glu Phe Asp Ala Pro Ser Pro Ser Pro Arg Asp Tyr Arg Glu
    290                 295                 300

Thr Trp Val Cys Ala Leu Gly Leu Thr Val Gly Ser Gly Gly Ala Ser
305                 310                 315                 320

Leu Leu Gly Xaa Ile Leu His His Gln Xaa Ile Ala Gln Lys Gln Cys
                325                 330                 335

<210> SEQ ID NO 15
<211> LENGTH: 962
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<220> FEATURE:
<221> NAME/KEY: CDS
<222> LOCATION: (3)..(14)
<220> FEATURE:
<221> NAME/KEY: CDS
<222> LOCATION: (24)..(917)
<220> FEATURE:
<221> NAME/KEY: modified_base
<222> LOCATION: (892)..(892)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: CDS
<222> LOCATION: (921)..(959)
<220> FEATURE:
<221> NAME/KEY: modified_base
<222> LOCATION: (944)..(944)
<223> OTHER INFORMATION: a, c, t, g, unknown or other

<400> SEQUENCE: 15
```

| | | | | | | | | | | | | |
|---|---|---|---|---|---|---|---|---|---|---|---|---|
| ga ttt tat ttt gac tgatagtga cct gtt tcg ttg caa caa att gat gag | | | | | | | | | | | | 50 |
| Phe Tyr Phe Asp | | | Pro Val Ser Leu Gln Gln Ile Asp Glu | | | | | | | | | |
| 1 | | | 5 | | | | 10 | | | | | |
| caa tgc ttt ttt ata atg cca act ttg tac aaa aaa gca ggc tcc gaa | | | | | | | | | | | | 98 |
| Gln Cys Phe Phe Ile Met Pro Thr Leu Tyr Lys Lys Ala Gly Ser Glu | | | | | | | | | | | | |
| 15 | | | | 20 | | | | 25 | | | | |
| ttc gcc ctt tta ttc ttg tct gtt ctg cct cac tcc cga gct cta ctg | | | | | | | | | | | | 146 |
| Phe Ala Leu Leu Phe Leu Ser Val Leu Pro His Ser Arg Ala Leu Leu | | | | | | | | | | | | |
| 30 | | | | 35 | | | | 40 | | | | 45 |
| act ccc aac aga gcg ccc aag aag aaa atg gcc ata agt gga gtc cct | | | | | | | | | | | | 194 |
| Thr Pro Asn Arg Ala Pro Lys Lys Lys Met Ala Ile Ser Gly Val Pro | | | | | | | | | | | | |
| | | | 50 | | | | 55 | | | | 60 | |
| gtg cta gga ttt ttc atc ata gct gtg ctg atg agc gct cag gaa tca | | | | | | | | | | | | 242 |
| Val Leu Gly Phe Phe Ile Ile Ala Val Leu Met Ser Ala Gln Glu Ser | | | | | | | | | | | | |
| | 65 | | | | 70 | | | | 75 | | | |
| tgg gct atc aaa gaa gaa cat gtg gat tcc gga tac gag gtg cac cag | | | | | | | | | | | | 290 |
| Trp Ala Ile Lys Glu Glu His Val Asp Ser Gly Tyr Glu Val His Gln | | | | | | | | | | | | |
| | 80 | | | | 85 | | | | 90 | | | |
| aag ata gga gga gga agt ggc ggc ggc agc ggt ggt ggt ggt agt | | | | | | | | | | | | 338 |
| Lys Ile Gly Gly Gly Ser Gly Gly Gly Ser Gly Gly Gly Gly Ser | | | | | | | | | | | | |
| | 95 | | | | 100 | | | | 105 | | | |
| atc atc cag gcc gag ttc tat ctg aat cct gac caa tca ggc gag ttt | | | | | | | | | | | | 386 |
| Ile Ile Gln Ala Glu Phe Tyr Leu Asn Pro Asp Gln Ser Gly Glu Phe | | | | | | | | | | | | |
| 110 | | | | 115 | | | | 120 | | | | 125 |
| atg ttt gac ttt gat ggt gat gag att ttc cat gtg gat atg gca aag | | | | | | | | | | | | 434 |
| Met Phe Asp Phe Asp Gly Asp Glu Ile Phe His Val Asp Met Ala Lys | | | | | | | | | | | | |
| | | | 130 | | | | 135 | | | | 140 | |
| aag gag acg gtc tgg cgg ctt gaa gaa ttt gga cga ttt gcc agc ttt | | | | | | | | | | | | 482 |
| Lys Glu Thr Val Trp Arg Leu Glu Glu Phe Gly Arg Phe Ala Ser Phe | | | | | | | | | | | | |
| | | 145 | | | | 150 | | | | 155 | | |
| gag gct caa ggt gca ttg gcc aac ata gct gtg gac aaa gcc aac ctg | | | | | | | | | | | | 530 |
| Glu Ala Gln Gly Ala Leu Ala Asn Ile Ala Val Asp Lys Ala Asn Leu | | | | | | | | | | | | |
| | | 160 | | | | 165 | | | | 170 | | |
| gaa atc atg aca aag cgc tcc aac tat act ccg atc acc aat gta cct | | | | | | | | | | | | 578 |
| Glu Ile Met Thr Lys Arg Ser Asn Tyr Thr Pro Ile Thr Asn Val Pro | | | | | | | | | | | | |
| 175 | | | | 180 | | | | 185 | | | | |
| cca gag gta act gtg ctc acg aac agc cct gtg gaa ctg aga gag ccc | | | | | | | | | | | | 626 |
| Pro Glu Val Thr Val Leu Thr Asn Ser Pro Val Glu Leu Arg Glu Pro | | | | | | | | | | | | |
| 190 | | | | 195 | | | | 200 | | | | 205 |
| aac gtc ctc atc tgt ttc ata gac aag ttc acc cca cca gtg gtc aat | | | | | | | | | | | | 674 |
| Asn Val Leu Ile Cys Phe Ile Asp Lys Phe Thr Pro Pro Val Val Asn | | | | | | | | | | | | |
| | | | 210 | | | | 215 | | | | 220 | |

-continued

```
gtc acg tgg ctt cga aat gga aaa cct gtc acc aca gga gtg tca gag      722
Val Thr Trp Leu Arg Asn Gly Lys Pro Val Thr Thr Gly Val Ser Glu
            225                 230                 235 aca gtc ttc ctg ccc agg gaa gac cac ctt ttc cgc aag ttc cac tat      770
Thr Val Phe Leu Pro Arg Glu Asp His Leu Phe Arg Lys Phe His Tyr
        240                 245                 250 ctc ccc ttc ctg ccc tca act gag gac gtt tac gac tgc agg gtg gag      818
Leu Pro Phe Leu Pro Ser Thr Glu Asp Val Tyr Asp Cys Arg Val Glu
    255                 260                 265 cac tgg ggc ttg gat gag cct ctt ctc aag cac tgg gag ttt gat gct      866
His Trp Gly Leu Asp Glu Pro Leu Leu Lys His Trp Glu Phe Asp Ala
270                 275                 280                 285 cca agc ccc tct ccc aga gac tac ana naa acg tgg tgt gtg ccc tgg      914
Pro Ser Pro Ser Pro Arg Asp Tyr Xaa Xaa Thr Trp Cys Val Pro Trp
                290                 295                 300 gcc tga ctg tgg ggt ctg gtg ggc atc atn att ggg gac cat cat tca      962
Ala     Leu Trp Gly Leu Val Gly Ile Xaa Ile Gly Asp His His
            305                 310                 315

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Tyr Phe Asp
1

<210> SEQ ID NO 17
<211> LENGTH: 298
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (290)..(290)
<223> OTHER INFORMATION: Lys, Arg, Thr or Ile
<220> FEATURE:
<221> NAME/KEY: MOD_RES
<222> LOCATION: (291)..(291)
<223> OTHER INFORMATION: Lys, Glu or Gln

<400> SEQUENCE: 17

Pro Val Ser Leu Gln Gln Ile Asp Glu Gln Cys Phe Phe Ile Met Pro
1               5                   10                  15

Thr Leu Tyr Lys Lys Ala Gly Ser Glu Phe Ala Leu Leu Phe Leu Ser
            20                  25                  30

Val Leu Pro His Ser Arg Ala Leu Leu Thr Pro Asn Arg Ala Pro Lys
        35                  40                  45

Lys Lys Met Ala Ile Ser Gly Val Pro Val Leu Gly Phe Phe Ile Ile
    50                  55                  60

Ala Val Leu Met Ser Ala Gln Glu Ser Trp Ala Ile Lys Glu Glu His
65                  70                  75                  80

Val Asp Ser Gly Tyr Glu Val His Gln Lys Ile Gly Gly Ser Gly
            85                  90                  95

Gly Gly Gly Ser Gly Gly Gly Ser Ile Ile Gln Ala Glu Phe Tyr
            100                 105                 110
```

```
Leu Asn Pro Asp Gln Ser Gly Glu Phe Met Phe Asp Phe Asp Gly Asp
            115                 120                 125

Glu Ile Phe His Val Asp Met Ala Lys Lys Glu Thr Val Trp Arg Leu
    130                 135                 140

Glu Glu Phe Gly Arg Phe Ala Ser Phe Glu Ala Gln Gly Ala Leu Ala
145                 150                 155                 160

Asn Ile Ala Val Asp Lys Ala Asn Leu Glu Ile Met Thr Lys Arg Ser
                165                 170                 175

Asn Tyr Thr Pro Ile Thr Asn Val Pro Pro Glu Val Thr Val Leu Thr
            180                 185                 190

Asn Ser Pro Val Glu Leu Arg Glu Pro Asn Val Leu Ile Cys Phe Ile
        195                 200                 205

Asp Lys Phe Thr Pro Pro Val Val Asn Val Thr Trp Leu Arg Asn Gly
    210                 215                 220

Lys Pro Val Thr Thr Gly Val Ser Glu Thr Val Phe Leu Pro Arg Glu
225                 230                 235                 240

Asp His Leu Phe Arg Lys Phe His Tyr Leu Pro Phe Leu Pro Ser Thr
                245                 250                 255

Glu Asp Val Tyr Asp Cys Arg Val Glu His Trp Gly Leu Asp Glu Pro
            260                 265                 270

Leu Leu Lys His Trp Glu Phe Asp Ala Pro Ser Pro Ser Pro Arg Asp
        275                 280                 285

Tyr Xaa Xaa Thr Trp Cys Val Pro Trp Ala
    290                 295

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ile or Met

<400> SEQUENCE: 18

Leu Trp Gly Leu Val Gly Ile Xaa Ile Gly Asp His His
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Leu Val Phe Phe Ala Glu Asp Val Gly Ser Asn Gly Ala
1               5                   10

<210> SEQ ID NO 20
<211> LENGTH: 1003
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (15)..(1001)
```

<220> FEATURE:
<221> NAME/KEY: modified_base
<222> LOCATION: (963)..(963)
<223> OTHER INFORMATION: a, c, t, g, unknown or other
<220> FEATURE:
<221> NAME/KEY: modified_base
<222> LOCATION: (981)..(981)
<223> OTHER INFORMATION: a, c, t, g, unknown or other

<400> SEQUENCE: 20

```
atgatttatt ttga ctg ata gtg acc tgt tcg ttg caa caa att gat gag      50
              Leu Ile Val Thr Cys Ser Leu Gln Gln Ile Asp Glu
               1               5                  10 caa tgc ttt ttt ata atg cca act ttg tac aaa aaa gca ggc tcc gaa      98
Gln Cys Phe Phe Ile Met Pro Thr Leu Tyr Lys Lys Ala Gly Ser Glu
     15                  20                  25 ttc gcc ctt tta ttc ttg tct gtt ctg cct cac tcc cga gct cta ctg     146
Phe Ala Leu Leu Phe Leu Ser Val Leu Pro His Ser Arg Ala Leu Leu
 30                  35                  40 act ccc aac aga gcg ccc aag aag aaa atg gcc ata agt gga gtc cct     194
Thr Pro Asn Arg Ala Pro Lys Lys Lys Met Ala Ile Ser Gly Val Pro
 45                  50                  55                  60 gtg cta gga ttt ttc atc ata gct gtg ctg atg agc gct cag gaa tca     242
Val Leu Gly Phe Phe Ile Ile Ala Val Leu Met Ser Ala Gln Glu Ser
                 65                  70                  75 tgg gct atc aaa gaa gaa cat gtg gta gga tcc aac aag ggc gca atc     290
Trp Ala Ile Lys Glu Glu His Val Val Gly Ser Asn Lys Gly Ala Ile
             80                  85                  90 ata ggt ctc atg ata gga gga gga agt ggc ggc ggc ggc agc ggt ggt     338
Ile Gly Leu Met Ile Gly Gly Gly Ser Gly Gly Gly Gly Ser Gly Gly
         95                 100                 105 ggt ggt agt atc atc cag gcc gag ttc tat ctg aat cct gac caa tca     386
Gly Gly Ser Ile Ile Gln Ala Glu Phe Tyr Leu Asn Pro Asp Gln Ser
     110                 115                 120 ggc gag ttt atg ttt gac ttt gat ggt gat gag att ttc cat gtg gat     434
Gly Glu Phe Met Phe Asp Phe Asp Gly Asp Glu Ile Phe His Val Asp
125                 130                 135                 140 atg gca aag aag gag acg gtc tgg cgg ctt gaa gaa ttt gga cga ttt     482
Met Ala Lys Lys Glu Thr Val Trp Arg Leu Glu Glu Phe Gly Arg Phe
                 145                 150                 155 gcc agc ttt gag gct caa ggt gca ttg gcc aac ata gct gtg gac aaa     530
Ala Ser Phe Glu Ala Gln Gly Ala Leu Ala Asn Ile Ala Val Asp Lys
             160                 165                 170 gcc aac ctg gaa atc atg aca aag cgc tcc aac tat act ccg atc acc     578
Ala Asn Leu Glu Ile Met Thr Lys Arg Ser Asn Tyr Thr Pro Ile Thr
         175                 180                 185 aat gta cct cca gag gta act gtg ctc acg aac agc cct gtg gaa ctg     626
Asn Val Pro Pro Glu Val Thr Val Leu Thr Asn Ser Pro Val Glu Leu
     190                 195                 200 aga gag ccc aac gtc ctc atc tgt ttc ata gac aag ttc acc cca cca     674
Arg Glu Pro Asn Val Leu Ile Cys Phe Ile Asp Lys Phe Thr Pro Pro
205                 210                 215                 220 gtg gtc aat gtc acg tgg ctt cga aat gga aaa cct gtc acc aca gga     722
Val Val Asn Val Thr Trp Leu Arg Asn Gly Lys Pro Val Thr Thr Gly
                 225                 230                 235 gtg tca gag aca gtc ttc ctg ccc agg gaa gac cac ctt ttc cgc aag     770
Val Ser Glu Thr Val Phe Leu Pro Arg Glu Asp His Leu Phe Arg Lys
             240                 245                 250 ttc cac tat ctc ccc ttc ctg ccc tca act gag gac gtt tac gac tgc     818
Phe His Tyr Leu Pro Phe Leu Pro Ser Thr Glu Asp Val Tyr Asp Cys
         255                 260                 265
```

-continued

```
agg gtg gag cac tgg ggc ttg gat gag cct ctt ctc aag cac tgg gag    866
Arg Val Glu His Trp Gly Leu Asp Glu Pro Leu Leu Lys His Trp Glu
    270                 275                 280 ttt gat gct cca agc ccc tct ccc aga gac tac aga gaa acg tgg gtg    914
Phe Asp Ala Pro Ser Pro Ser Pro Arg Asp Tyr Arg Glu Thr Trp Val
285                 290                 295                 300 tgt gcc ctg ggc ctg act gtg ggg tct ggt ggg gca tca tta ttg gga    962
Cys Ala Leu Gly Leu Thr Val Gly Ser Gly Gly Ala Ser Leu Leu Gly
                305                 310                 315 ncc att ctt cat cat caa ngg att gcg caa aag caa tgc ac            1003
Xaa Ile Leu His His Gln Xaa Ile Ala Gln Lys Gln Cys
                320                 325
```

<210> SEQ ID NO 21
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (317)..(317)
<223> OTHER INFORMATION: Thr, Ala, Pro or Ser
<220> FEATURE:
<221> NAME/KEY: MOD_RES
<222> LOCATION: (323)..(323)
<223> OTHER INFORMATION: Arg, Gly or Trp

<400> SEQUENCE: 21

```
Leu Ile Val Thr Cys Ser Leu Gln Gln Ile Asp Glu Gln Cys Phe Phe
1               5                   10                  15

Ile Met Pro Thr Leu Tyr Lys Lys Ala Gly Ser Glu Phe Ala Leu Leu
                20                  25                  30

Phe Leu Ser Val Leu Pro His Ser Arg Ala Leu Leu Thr Pro Asn Arg
            35                  40                  45

Ala Pro Lys Lys Lys Met Ala Ile Ser Gly Val Pro Val Leu Gly Phe
        50                  55                  60

Phe Ile Ile Ala Val Leu Met Ser Ala Gln Glu Ser Trp Ala Ile Lys
65                  70                  75                  80

Glu Glu His Val Val Gly Ser Asn Lys Gly Ala Ile Ile Gly Leu Met
                85                  90                  95

Ile Gly Gly Gly Ser Gly Gly Gly Ser Gly Gly Gly Ser Ile
            100                 105                 110

Ile Gln Ala Glu Phe Tyr Leu Asn Pro Asp Gln Ser Gly Glu Phe Met
        115                 120                 125

Phe Asp Phe Asp Gly Asp Glu Ile Phe His Val Asp Met Ala Lys Lys
130                 135                 140

Glu Thr Val Trp Arg Leu Glu Glu Phe Gly Arg Phe Ala Ser Phe Glu
145                 150                 155                 160

Ala Gln Gly Ala Leu Ala Asn Ile Ala Val Asp Lys Ala Asn Leu Glu
                165                 170                 175

Ile Met Thr Lys Arg Ser Asn Tyr Thr Pro Ile Thr Asn Val Pro Pro
            180                 185                 190

Glu Val Thr Val Leu Thr Asn Ser Pro Val Glu Leu Arg Glu Pro Asn
        195                 200                 205

Val Leu Ile Cys Phe Ile Asp Lys Phe Thr Pro Pro Val Val Asn Val
    210                 215                 220

Thr Trp Leu Arg Asn Gly Lys Pro Val Thr Thr Gly Val Ser Glu Thr
225                 230                 235                 240
```

```
Val Phe Leu Pro Arg Glu Asp His Leu Phe Arg Lys Phe His Tyr Leu
            245                 250                 255

Pro Phe Leu Pro Ser Thr Glu Asp Val Tyr Asp Cys Arg Val Glu His
            260                 265                 270

Trp Gly Leu Asp Glu Pro Leu Leu Lys His Trp Glu Phe Asp Ala Pro
            275                 280                 285

Ser Pro Ser Pro Arg Asp Tyr Arg Glu Thr Trp Val Cys Ala Leu Gly
            290                 295                 300

Leu Thr Val Gly Ser Gly Gly Ala Ser Leu Leu Gly Xaa Ile Leu His
305                 310                 315                 320

His Gln Xaa Ile Ala Gln Lys Gln Cys
            325

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ile Ile Gly Leu Met Val Gly Gly Val Val Ile Ala
1               5                   10

<210> SEQ ID NO 23
<211> LENGTH: 1019
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(15)
<220> FEATURE:
<221> NAME/KEY: CDS
<222> LOCATION: (25)..(1017)
<220> FEATURE:
<221> NAME/KEY: modified_base
<222> LOCATION: (979)..(979)
<223> OTHER INFORMATION: a, c, t, g, unknown or other
<220> FEATURE:
<221> NAME/KEY: modified_base
<222> LOCATION: (997)..(997)
<223> OTHER INFORMATION: a, c, t, g, unknown or other

<400> SEQUENCE: 23 atg att tat ttt gac tgatagtga cct gtt tcg ttg caa caa att gat gag      51
Met Ile Tyr Phe Asp          Pro Val Ser Leu Gln Gln Ile Asp Glu
1               5                        10 caa tgc ttt ttt ata atg cca act ttg tac aaa aaa gca ggc tcc gaa        99
Gln Cys Phe Phe Ile Met Pro Thr Leu Tyr Lys Lys Ala Gly Ser Glu
15              20                  25                  30 ttc gcc ctt tta ttc ttg tct gtt ctg cct cac tcc cga gct cta ctg       147
Phe Ala Leu Leu Phe Leu Ser Val Leu Pro His Ser Arg Ala Leu Leu
                35                  40                  45 act ccc aac aga gcg ccc aag aag aaa atg gcc ata agt gga gtc cct       195
Thr Pro Asn Arg Ala Pro Lys Lys Lys Met Ala Ile Ser Gly Val Pro
            50                  55                  60 gtg cta gga ttt ttc atc ata gct gtg ctg atg agc gct cag gaa tca       243
Val Leu Gly Phe Phe Ile Ile Ala Val Leu Met Ser Ala Gln Glu Ser
        65                  70                  75 tgg gct atc aaa gaa gaa cat gtg gat tcc gga tac gag gtg cac cac       291
```

```
                Trp Ala Ile Lys Glu Glu His Val Asp Ser Gly Tyr Glu Val His His
                 80                  85                  90 cag aag ctc gtg ttc ttc gca gag gat ata gga gga gga agt ggc ggc      339
Gln Lys Leu Val Phe Phe Ala Glu Asp Ile Gly Gly Gly Ser Gly Gly
 95                 100                 105                 110 ggc ggc agc ggt ggt ggt ggt agt atc atc cag gcc gag ttc tat ctg      387
Gly Gly Ser Gly Gly Gly Gly Ser Ile Ile Gln Ala Glu Phe Tyr Leu
                    115                 120                 125 aat cct gac caa tca ggc gag ttt atg ttt gac ttt gat ggt gat gag      435
Asn Pro Asp Gln Ser Gly Glu Phe Met Phe Asp Phe Asp Gly Asp Glu
                130                 135                 140 att ttc cat gtg gat atg gca aag aag gag acg gtc tgg cgg ctt gaa      483
Ile Phe His Val Asp Met Ala Lys Lys Glu Thr Val Trp Arg Leu Glu
            145                 150                 155 gaa ttt gga cga ttt gcc agc ttt gag gct caa ggt gca ttg gcc aac      531
Glu Phe Gly Arg Phe Ala Ser Phe Glu Ala Gln Gly Ala Leu Ala Asn
        160                 165                 170 ata gct gtg gac aaa gcc aac ctg gaa atc atg aca aag cgc tcc aac      579
Ile Ala Val Asp Lys Ala Asn Leu Glu Ile Met Thr Lys Arg Ser Asn
175                 180                 185                 190 tat act ccg atc acc aat gta cct cca gag gta act gtg ctc acg aac      627
Tyr Thr Pro Ile Thr Asn Val Pro Pro Glu Val Thr Val Leu Thr Asn
                    195                 200                 205 agc cct gtg gaa ctg aga gag ccc aac gtc ctc atc tgt ttc ata gac      675
Ser Pro Val Glu Leu Arg Glu Pro Asn Val Leu Ile Cys Phe Ile Asp
                210                 215                 220 aag ttc acc cca cca gtg gtc aat gtc acg tgg ctt cga aat gga aaa      723
Lys Phe Thr Pro Pro Val Val Asn Val Thr Trp Leu Arg Asn Gly Lys
            225                 230                 235 cct gtc acc aca gga gtg tca gag aca gtc ttc ctg ccc agg gaa gac      771
Pro Val Thr Thr Gly Val Ser Glu Thr Val Phe Leu Pro Arg Glu Asp
        240                 245                 250 cac ctt ttc cgc aag ttc cac tat ctc ccc ttc ctg ccc tca act gag      819
His Leu Phe Arg Lys Phe His Tyr Leu Pro Phe Leu Pro Ser Thr Glu
255                 260                 265                 270 gac gtt tac gac tgc agg gtg gag cac tgg ggc ttg gat gag cct ctt      867
Asp Val Tyr Asp Cys Arg Val Glu His Trp Gly Leu Asp Glu Pro Leu
                    275                 280                 285 ctc aag cac tgg gag ttt gat gct cca agc ccc tct ccc aga gac tac      915
Leu Lys His Trp Glu Phe Asp Ala Pro Ser Pro Ser Pro Arg Asp Tyr
                290                 295                 300 aga gaa acg tgg gtg tgt gcc ctg ggc ctg act gtg ggg tct ggt ggg      963
Arg Glu Thr Trp Val Cys Ala Leu Gly Leu Thr Val Gly Ser Gly Gly
            305                 310                 315 gca tca tta ttg gga ncc att ctt cat cat caa ngg att gcg caa aag     1011
Ala Ser Leu Leu Gly Xaa Ile Leu His His Gln Xaa Ile Ala Gln Lys
        320                 325                 330 caa tgc ac                                                          1019
Gln Cys
335
```

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Ile Tyr Phe Asp

<210> SEQ ID NO 25
<211> LENGTH: 331
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (319)..(319)
<223> OTHER INFORMATION: Thr, Ala, Pro or Ser
<220> FEATURE:
<221> NAME/KEY: MOD_RES
<222> LOCATION: (325)..(325)
<223> OTHER INFORMATION: Arg, Gly or Trp

<400> SEQUENCE: 25

```
Pro Val Ser Leu Gln Gln Ile Asp Glu Gln Cys Phe Phe Ile Met Pro
1               5                   10                  15

Thr Leu Tyr Lys Lys Ala Gly Ser Glu Phe Ala Leu Leu Phe Leu Ser
            20                  25                  30

Val Leu Pro His Ser Arg Ala Leu Leu Thr Pro Asn Arg Ala Pro Lys
        35                  40                  45

Lys Lys Met Ala Ile Ser Gly Val Pro Val Leu Gly Phe Phe Ile Ile
50                  55                  60

Ala Val Leu Met Ser Ala Gln Glu Ser Trp Ala Ile Lys Glu Glu His
65                  70                  75                  80

Val Asp Ser Gly Tyr Glu Val His His Gln Lys Leu Val Phe Phe Ala
                85                  90                  95

Glu Asp Ile Gly Gly Gly Ser Gly Gly Gly Ser Gly Gly Gly Gly Gly
            100                 105                 110

Ser Ile Ile Gln Ala Glu Phe Tyr Leu Asn Pro Asp Gln Ser Gly Glu
        115                 120                 125

Phe Met Phe Asp Phe Asp Gly Asp Glu Ile Phe His Val Asp Met Ala
    130                 135                 140

Lys Lys Glu Thr Val Trp Arg Leu Glu Glu Phe Gly Arg Phe Ala Ser
145                 150                 155                 160

Phe Glu Ala Gln Gly Ala Leu Ala Asn Ile Ala Val Asp Lys Ala Asn
                165                 170                 175

Leu Glu Ile Met Thr Lys Arg Ser Asn Tyr Thr Pro Ile Thr Asn Val
            180                 185                 190

Pro Pro Glu Val Thr Val Leu Thr Asn Ser Pro Val Glu Leu Arg Glu
        195                 200                 205

Pro Asn Val Leu Ile Cys Phe Ile Asp Lys Phe Thr Pro Pro Val Val
    210                 215                 220

Asn Val Thr Trp Leu Arg Asn Gly Lys Pro Val Thr Thr Gly Val Ser
225                 230                 235                 240

Glu Thr Val Phe Leu Pro Arg Gly Asp His Leu Phe Arg Lys Phe His
                245                 250                 255

Tyr Leu Pro Phe Leu Pro Ser Thr Glu Asp Val Tyr Asp Cys Arg Val
            260                 265                 270

Glu His Trp Gly Leu Asp Glu Pro Leu Leu Lys His Trp Glu Phe Asp
        275                 280                 285

Ala Pro Ser Pro Ser Pro Arg Asp Tyr Arg Glu Thr Trp Val Cys Ala
    290                 295                 300

Leu Gly Leu Thr Val Gly Ser Gly Gly Ala Ser Leu Leu Gly Xaa Ile
```

-continued

```
            305                 310                 315                 320
Leu His His Gln Xaa Ile Ala Gln Lys Gln Cys
                    325                 330
```